(12) United States Patent
Iyer et al.

(10) Patent No.: US 6,420,337 B1
(45) Date of Patent: Jul. 16, 2002

(54) HIGHLY PURIFIED CYTOKINE ACTIVATING FACTOR AND METHODS OF USE

(75) Inventors: Subramanian Iyer, Hockessin, DE (US); Tay N. Nguyen, Telford, PA (US); Dauh-Rurng Wu; Ruye Xing, both of Wilmington, DE (US)

(73) Assignee: Arkion Life Sciences LLC, Wilmington, DE (US)

( * ) Notice: Subject to any disclaimer, the term of this patent is extended or adjusted under 35 U.S.C. 154(b) by 0 days.

(21) Appl. No.: 09/620,093

(22) Filed: Jul. 20, 2000

Related U.S. Application Data
(60) Provisional application No. 60/145,317, filed on Jul. 23, 1999, and provisional application No. 60/197,619, filed on Apr. 14, 2000.

(51) Int. Cl.[7] ............................................... A01N 37/18
(52) U.S. Cl. .......................... 514/2; 424/581; 530/324; 530/412; 530/853
(58) Field of Search ............................... 514/2; 530/300

(56) References Cited

PUBLICATIONS

R.S. Stephens et al. Genome sequence of an obligate intracellular pathogen of humans: Chlamydia trachomatis. Oct. 1998. Science 282:754–759.*

Q. Zhou et al. Locus 042210, Jan. 1, 1998, Accessed Apr. 6, 2001 (see attached computer printout).*

R.J. Meis et al. Genetic and molecular biological characterization of a vaccinia virus gene which renders the virus dependent on isatin–beta–thiosemicarbazone (IBT). 1991. Virology, 182:442–454.*

* cited by examiner

Primary Examiner—Lorraine Spector
Assistant Examiner—Dong Jiang
(74) Attorney, Agent, or Firm—Sheridan Ross P.C.

(57) ABSTRACT

Disclosed is an isolated Cytokine Activating Factor (CAF) protein, an isolated nucleic acid molecule encoding a CAF protein, an antibody that selectively binds to a CAF protein, a composition comprising a Cytokine Activating Factor (CAF), and a method for modulating the immune system using the composition. Also disclosed is a method for treating cancer using such a composition.

33 Claims, 20 Drawing Sheets

Lane 1. Standard
Lane 2. PL-100 egg 3K permeate, 1996
Lane 5. PL-100 egg 3K permeate, 1998
Lane 6. Table egg 3K permeate, 1998
Lane 7. PL-100 whole egg, 1998
Lane 8. Table whole egg, 1998

| Lane 1. | Standard | |
| Lane 2. | Blank | 0 h |
| Lane 3. | Table egg | 0 h |
| Lane 4. | PL-100 egg | 0 h |
| Lane 5. | Blank | 1 h |
| Lane 6. | Table egg | 1 h |
| Lane 7. | PL-100 egg | 1 h |
| Lane 8. | Blank | 2 h |
| Lane 9. | Table egg | 2 h |
| Lane 10. | PL-100 egg | 2 h |
| Lane 11. | Blank | 4 h |
| Lane 12. | Table egg | 4 h |
| Lane 13. | PL-100 egg | 4 h |
| Lane 14. | Blank | 8 h |
| Lane 15. | Table egg | 8 h |
| Lane 16. | PL-100 egg | 8 h |

Lane 1.   Standard
Lane 2.   0.2 M NaCL fraction
Lane 3.   0.5 M NaCL fraction
Lane 4.   1.0 M NaCL fraction
Lane 5.   1.5 M NaCL fraction Lane 1. Standard
Lane 2. SPE fraction 5
Lane 3. SPE fraction 4
Lane 4  SPE fraction 3
Lane 5. SPE fraction 2
Lane 6. SPE fraction 1

STD. Standard
Lane 1. HPLC fraction 1
Lane 2. HPLC fraction 2
Lane 3. HPLC fraction 3
Lane 4. HPLC fraction 4
Lane 5. HPLC fraction 5

Chicken Vitellogenin II Precursor     (SEQ ID NO:5)

*ORIGIN*

```
   1 mrgiilalvl tlvgsqkfdi dpgfnsrrsy lynyegsmln glqdrslgka gvrlssklei
  61 sglpenayll kvrspqveey ngvwprdpft rsskitqvis scftrlfkfe yssgrigniy
 121 apedcpdlcv nivrgilnmf qmtikksqnv yelqeagigg icharyviqe drknsriyvt
 181 rtvdlnncqe kvqksigmay iypcpvdvmk erltkgttaf syklkqsdsg tlitdvssrq
 241 vyqispfnep tgvavmearq qltlvevrse rgsapdvpmq nygslryrfp avlpqmplql
 301 iktknpeqri vetlqhivln nqqdfhddvs yrflevvqlc rianadnles iwrqvsdkpr
 361 yrrwllsavs asgttetlkf lknrirnddl nyiqtllltvs ltlhllqade htlpiaadlm
 421 tssriqknpv lqqvaclgys svvnrycsqt sacpkealqp ihdladeais rgredkmkla
 481 lkcignmgep aslkrilkfl pissssaadi pvhiqidait alkkiawkdp ktvqgyliqi
 541 ladqslppev rmmacavife trpalalitt ianvamkesn mqvasfvysh mkslsksrlp
 601 fmynissacn lalkllspkl dsmsyryskv iradtyfdny rvgatgeifv vnsprtmfps
 661 aiisklmans agsvadlvep girvegladv imkrnipfae yptykqikel gkalqgwkel
 721 ptetplvsay lkilgqevaf ininkellqq vmktvvepad rnaaikrian qirnsiagqw
 781 tqpvwmgelr yvvpsclglp leygsyttal araavsvegk mtppltgdfr lsqllestmq
 841 irsdlkpsly vhtvatmgvn teyfqhavei qgevqtrmpm kfdakidvkl knlkietnpc
 901 reeteivvgr hkafavsrni gelgvekrts ilpedapldv teepfqtser asrehfamqg
 961 pdsmprkqsh ssredlrrst gkrahkrdic lkmhhigcql cfsrrsdas fiqntylhkl
1021 igeheakivl mpvhtdadid kiqleiqags raaariitev npeseeedes spyediqakl
1081 krilgidsmf kvanktrhpk nrpskkgntv laefgtepda ktssssssas statsssssss
1141 asspnrkkpm deeendqvkq arnkdassss rsskssnssk rssskssnss krsssssssss
1201 ssssrsssss sssssnskss sssskssssss srsrssskss sssssssssss sskssssrss
1261 ssssksshh shshsghln gssssssssr svshhshehh sghleddsss sssssvlski
1321 wgrheiyqyr frsahrqefp krklpgdrat srysstrssh dtsraaswpk flgdiktpvl
1381 aaflhgisnn kktgglqlvv yadtdsvrpr vqvfvtnltd sskwklcada svrnahkava
1441 yvkwgwdcrd ykvstelvtg rfaghpaaqv klewpkvpsn vrsvvewfye fvpgaafmlg
1501 fsermdknps rqarmvvalt sprtcdvvvk lpdiilyqka vrlplslpvg pripaselqp
1561 piwnvfaeap savlenlkar csvsynkikt fnevkfnysm pancyhilvq dcsselkflv
1621 mmksageatn lkainikigs heidmhpvng qvkllvdgae sptanislis agaslwihne
1681 nqgfalaapg hgidklyfdg ktitiqvplw magktcgicg kydaeceqey rmpngylakn
1741 avsfghswil eeapcrgack lhrsfvklek tvqlagvdsk cystepvlrc akgcsatktt
1801 pvtvgfhclp adsansltdk qmkydqksed mqdtvdahtt csceneecst
```

| From data: | AViENLKARX xVSXNx IxTFNqV x Fx YSMPA | (SEQ ID NO:4) |
|---|---|---|
| Vitell II Precursor: | AVLENLKARCSVSYNKIKTFNEVKFNYSMPA | (positions 1572-1602 of SEQ ID NO:5) |

FIG. 15

\* Cytokine active fractions.

1. SPE-Water Soluble Fraction   TNF-α Level
2. SPE-Water Soluble Fraction   IL-1β Level
3. SPE-Water Soluble Fraction   IL-6 Level
4. CAFb Fraction   TNF-α Level
5. CAFb Fraction   IL-1 β Level
6. CAFb Fraction   IL-6 Level
7. Control

HIGHLY PURIFIED CYTOKINE ACTIVATING FACTOR AND METHODS OF USE

CROSS-REFERENCE TO RELATED APPLICATIONS

This application claims the benefit of priority under 35 U.S.C. §119(e) from U.S. Provisional Application Serial No. 60/145,317, filed Jul. 23, 1999, entitled "Highly Purified Cytokine Activating Factor and Methods of Use" and from U.S. Provisional Application Serial No. 60/197,619, filed Apr. 14, 2000, entitled "Highly Purified Cytokine Activating Factor and Methods of Use". The entire disclosures of U.S. Provisional Application Serial Nos. 60/145,317 and 60/197,619 are incorporated herein by reference and are considered to be part of the present disclosure.

BACKGROUND OF THE INVENTION

Biological factors, such as coenzymes, cofactors, vitamins and others, play important roles in biological conversion processes. They are usually produced in small amounts in a whole cell ($1 \times 10^{-5}$–$1 \times 10^{-6}$). Isolation and purification of such biological factors from normal cells, however, is a difficult project.

Hyperimmunized eggs have been developed and have been shown to over-produce antibodies and certain biological factors. Because hyperimmunization is performed by injection of polyvalent bacterial antigens into the target animal, the amount of biological factors found in eggs from these hyperimmunized animals can not be increased more than one order of magnitude. Therefore, the small amount of biological factors in hyperimmunized egg makes purification of biological factors difficult, and, as such, there is a need for an efficient process for isolating, purifying or otherwise producing such biological factors.

The normal immune system is under a balance in which proinflammatory and anti-inflammatory cells and molecules are carefully regulated to promote normal host immune defense without the destruction of host's tissues. Once this careful regulatory balance is disturbed, nonspecific stimulation and activation can lead to increased amounts of potent destructive immunological and inflammatory molecules being produced and released. Thus, excess production of proinflammatory cytokines or production of cytokines in the wrong biological context, are associated with mortality and pathology in a wide range of diseases, such as malaria, sepsis, rheumatoid arthritis, inflammatory bowel disease, cancer and AIDS, among others.

Cytokines are pluripotent polypeptides that act in autocrine/paracrine fashions by binding to specific cellular receptors. Their secretion is important in determining the duration and intensity of an immune response. For example, in mice, distinct subsets of CD4+ T helper (Th) clones secrete what have classically been described as Th1 and Th2 cytokines. Th1 cells produce interleukin-2 (IL-2) and interferon-$\gamma$ (IFN-$\gamma$) and facilitate the cellular immune response. Th2 cells produce IL-4, IL-5, IL-6 and IL-10 and support the activation of immunoglobulin secreting cells. During the process of inflammation, cytokines such as IL-1$\beta$, IL-6 and tumor necrosis factor-$\alpha$ (TNF$\alpha$) are released at the site of inflammation. These cytokines have pleiotropic effects and mediate a wide range of symptoms associated with inflammation.

A key cytokine, TNF-$\alpha$, also known as cachectin, is a 17 kiloDalton protein composed of 157 amino acids and produced mainly by monocytes and activated macrophages. TNF-$\alpha$ has been shown to possess tumoricidal activity as well as a variety of physiological effects with most major organ systems. In the central nervous system, TNF-$\alpha$ is involved in fever, anorexia, and alterations in pituitary hormone release. In the cardiovascular system, TNF-$\alpha$ plays a role in shock, acute respiratory distress and capillary leakage syndrome (procoagulation). TNF-$\alpha$ is instrumental in the process of acute tubular necrosis and nephritis in the kidney and ischemia, colitis, and hepatic necrosis in the gastrointestinal system. It is also a key cytokine involved in the process of inflammation.

Various genera of the class Aves, such as chickens (gallus domesticus), turkeys, and ducks, produce antibodies in blood and eggs against immunogens that cause avian diseases, as well as against other immunogens. For example, LeBacq-Verheyden et al. (*Immunology* 27:683 (974)) and Leslie, G. A., et al. (*J. Med.* 130:1337 (1969)), have quantitatively analyzed immunoglobulins of the chicken. Polson et al. (*Immunological Communications* 9:495–514 (1980)) immunized hens against several proteins and natural mixtures of proteins, and detected IgY antibodies in the yolks of the eggs. Fertel et al. (*Biochemical and Biophysical Research Communications* 102:1028:1033 (1981)) immunized hens against prostaglandins and detected antibodies in the egg yolk. Jensenius et al. (*Journal of Immunological Methods* 46:63–68 (1981)) provide a method of isolating egg yolk IgG for use in immunodiagnostics. Polson et al. (Immunological Communications 9:475–493 (1980)) describe antibodies isolated from the yolk of hens that were immunized with a variety of plant viruses.

U.S. Pat. No. 4,357,272 discloses the isolation of antibodies from the yolks of eggs derived from hyperimmunized hens. The antibody response was elicited by repetitive injections of immunogens derived from plant viruses, human IgG, tetanus antitoxin, snake antivenins, and Serameba.

U.S. Pat. No. 4,550,019 discloses the isolation from egg yolks of antibodies raised in the hen by hyperimmunization with immunogens having a molecular or particle weight of at least 30,000. The immunogens used to hyperimmunize the chickens were selected from among plant viruses, human immunoglobulins, tetanus toxin, and snake venoms.

U.S. Pat. No. 4,748,018 discloses a method of passive immunization of a mammal that comprises parenterally administering purified antibody obtained from the eggs of an avian that has been immunized against the corresponding antigen, and wherein the mammal has acquired immunity to the eggs.

U.S. Pat. No. 5,772,999, assigned to DCV-Biologics, discloses a method of preventing, countering or reducing chronic gastrointestinal disorders or Non-Steroidal Anti-Inflammatory Drug-induced (NSAID-induced) gastrointestinal damage in a subject by administering hyperimmunized egg and/or milk or fractions thereof to the subject.

SUMMARY OF THE INVENTION

The present invention is based on the present inventors' discovery that there is specific immunoregulatory activity in egg, and particularly in egg obtained from hyperimmunized animals, which when administered to a subject animal, and particularly, to mammals, activates cytokine production in that subject animal.

More specifically, the present invention is directed to a highly purified Cytokine Activating Factor which can be obtained from the eggs of an avian. The Cytokine Activating Factor can be highly purified from fractions isolated from both egg yolk and egg white. The Cytokine Activating Factor can also be produced recombinantly or by chemical synthesis.

One embodiment of the present invention relates to an isolated Cytokine Activating Factor (CAF) protein. Such protein comprises an amino acid sequence selected from the group of: (a) an amino acid sequence selected from the group of SEQ ID NO:1 and SEQ ID NO:6; and, (b) an amino acid sequence comprising at least 9 consecutive amino acid residues of either of the amino acid sequences of (a). The isolated CAF protein of the present invention upregulates expression of tumor necrosis factor α (TNFα), interleukin-1β (IL-1β) and/or interleukin-6 (IL-6), and/or downregulates expression of transforming growth factor β (TGFβ). In a preferred embodiment, the isolated protein of the present invention comprises an amino acid sequence having at least about 15 consecutive amino acid residues of either of the amino acid sequences of (a), and more preferably, at least about 20 consecutive amino acid residues, and even more preferably, at least about 25 consecutive amino acid residues of either of the amino acid sequences of (a). In another embodiment, the isolated protein of the present invention comprises an amino acid sequence having at least about 50 consecutive amino acid residues of SEQ ID NO:6.

In one embodiment of the present invention, an isolated protein of the present invention comprises an amino acid sequence that is at least about 65% identical to an amino acid sequence of (a) over at least 15 amino acids of the amino acid sequence of (a). Preferably, the protein comprises an amino acid sequence that is at least about 75% identical to an amino acid sequence of (a) over at least 15 amino acids of the amino acid sequence of (a). In another embodiment, the protein comprises an amino acid sequence that is at least about 60% identical to SEQ ID NO:6 over 66 amino acids of SEQ ID NO:6. In yet another embodiment, the protein is encoded by a nucleic acid sequence that hybridizes under high stringency conditions to a nucleic acid sequence encoding an amino acid sequence selected from the group of SEQ ID NO:1 and SEQ ID NO:6. In a most preferred embodiment, the isolated CAF protein of the present invention comprises amino acid sequence selected from the group consisting of SEQ ID NO:1 and SEQ ID NO:6, and most preferably, SEQ ID NO:6.

In one embodiment, an isolated CAF protein of the present invention has one or more of the following biochemical characteristics: (a) has at least one biologically active subunit which passes through a 3000 MW cut-of f filter; (b) is stable at a temperature up to at least about 50° C.; (c) is stable at pH of from about 2 to about 10; (d) is water soluble; (e) is non-steroidal; (f) is negatively charged; (g) is substantially non-polar; and/or, (h) has a $\lambda_{max}$ at about 254 nm. An isolated protein of the present invention is biologically active when administered orally. An isolated protein of the present invention is naturally present in both the egg white and egg yolk of avian eggs. As discussed above, an isolated CAF protein of the present invention preferably upregulates expression of tumor necrosis factor α (TNFα), interleukin-1β (IL-1β) and/or interleukin-6 (IL-6). In one embodiment, an isolated protein of the present invention downregulates the expression of transforming growth factor β (TGFβ).

One embodiment of the present invention relates to an isolated antibody that selectively binds to the isolated CAF protein of the present invention.

Yet another embodiment of the present invention relates to a composition. Such composition includes a pharmaceutically acceptable carrier and a cytokine activating factor (CAF) protein of the present invention as described above. In one embodiment, the pharmaceutically acceptable carrier is a food product selected from the group of: (a) a hyperimmune egg product which is selected to be enriched for the CAF protein; and, (b) a food product produced with at least a fraction of a hyperimmune egg product, wherein the fraction comprises an enriched amount of the CAF protein as compared to the hyperimmune egg product. Preferably, the pharmaceutically acceptable carrier comprises a fraction of a hyperimmune egg product containing an enriched amount of the CAF protein as compared to the hyperimmune egg product. Suitable fractions of a hyperimmune egg product include, but are not limited to: liquid egg yolk, liquid egg white, powdered egg yolk, powdered egg white, and a water soluble fraction of the hyperimmune egg product.

In one embodiment, the composition of the present invention is in a form selected from the group of a liquid, an aerosol, a capsule, a tablet, a pill, a powder, a gel and a granule. In another embodiment, the pharmaceutically acceptable carrier comprises a controlled release formulation. In yet another embodiment, the pharmaceutically acceptable carrier is selected from the group of: water, phosphate buffered saline, Ringer's solution, dextrose solution, serum-containing solutions, Hank's solution, other aqueous physiologically balanced solutions, oils, esters, glycols, biocompatible polymers, polymeric matrices, capsules, microcapsules, microparticles, bolus preparations, osmotic pumps, diffusion devices, liposomes, lipospheres, cells, and cellular membranes.

Yet another embodiment of the present invention relates to a method to regulate an immune response in an animal. Such a method includes the step of administering to the animal a composition comprising a cytokine activating factor (CAF) protein of the present invention as set forth previously herein. Preferably, the composition includes a pharmaceutically acceptable carrier. In one aspect, the composition is administered at a dose of from about 1 nanogram to about 400 milligrams of the CAF protein per kilogram body weight of the animal. Preferred routes of administration include, but are not limited to: oral, intravenous administration, intraperitoneal administration, intramuscular administration, subcutaneous administration, transdermal delivery, intratracheal administration, inhalation, impregnation of a catheter, by suppository, and direct injection into a tissue. In one embodiment, the composition comprises a food product containing the CAF protein. In a preferred embodiment, the animal is a mammal.

Preferably, administration of the composition upregulates expression of tumor necrosis factor α (TNFα), interleukin-1β (IL-1β) and/or interleukin-6 (IL-6) by cells of the animal. In one aspect, administration of the composition downregulates expression of transforming growth factor β (TGFβ) by cells of the animal.

Another embodiment of the present invention relates to a method of treating cancer in an animal. Such a method includes the steps of administering to an animal that has or is at risk of developing cancer a composition comprising a cytokine activating factor (CAF) protein of the present invention as previously described herein. Preferably, the composition is administered at a dose of from about 1 nanogram to about 400 milligrams of the CAF protein per kilogram body weight of the animal. Preferred routes of administration include, but are not limited to: oral, intravenous administration, intraperitoneal administration, intramuscular administration, subcutaneous administration, transdermal delivery, intratracheal administration, inhalation, impregnation of a catheter, by suppository, and direct injection into a tissue at or adjacent to the cancer. In one embodiment, the composition comprises a food product containing the CAF protein.

Preferably, administration of the composition produces a result selected from the group of: reduction in symptoms of the cancer, reduction of a tumor associated with the cancer, elimination of a tumor associated with the cancer, prevention of metastatic cancer, prevention of the cancer and stimulation of effector cell immunity against the cancer.

Yet another embodiment of the present invention relates to an isolated nucleic acid molecule. Such a nucleic acid molecule comprises a nucleic acid sequence selected from the group of: (a) a nucleic acid sequence encoding a protein comprising an amino acid sequence selected from the group consisting of: (i) an amino acid sequence selected from the group consisting of SEQ ID NO:1 and SEQ ID NO:6; and, (ii) an amino acid sequence comprising at least 9 consecutive amino acid residues of an amino acid sequence of (i); and, (b) a nucleic acid sequence that is fully complementary to the nucleic acid sequence of (a). Preferably, the protein encoded by the nucleic acid sequence of (a) upregulates expression of tumor necrosis factor α (TNFα), interleukin-1β (IL-1β) and/or interleukin-6 (IL-6). In a preferred embodiment, the nucleic acid molecule comprises a nucleic acid sequence encoding an amino acid sequence selected from the group of SEQ ID NO:1 and SEQ ID NO:6.

One embodiment of the present invention relates to a recombinant nucleic acid molecule comprising an isolated nucleic acid molecule of the present invention as set forth previously herein. Yet another embodiment of the present invention relates to a recombinant cell comprising an isolated nucleic acid molecule of the present invention as set forth previously herein, wherein the cell expresses the nucleic acid molecule. Yet another embodiment of the present invention relates to an isolated nucleic acid molecule of the present invention as set forth previously herein.

BRIEF DESCRIPTION OF THE FIGURES

FIG. 15 shows the alignment and positioning of the SPE-GFII sequence with chicken vitellogenin II precursor.

DETAILED DESCRIPTION OF THE INVENTION

Figure 1:
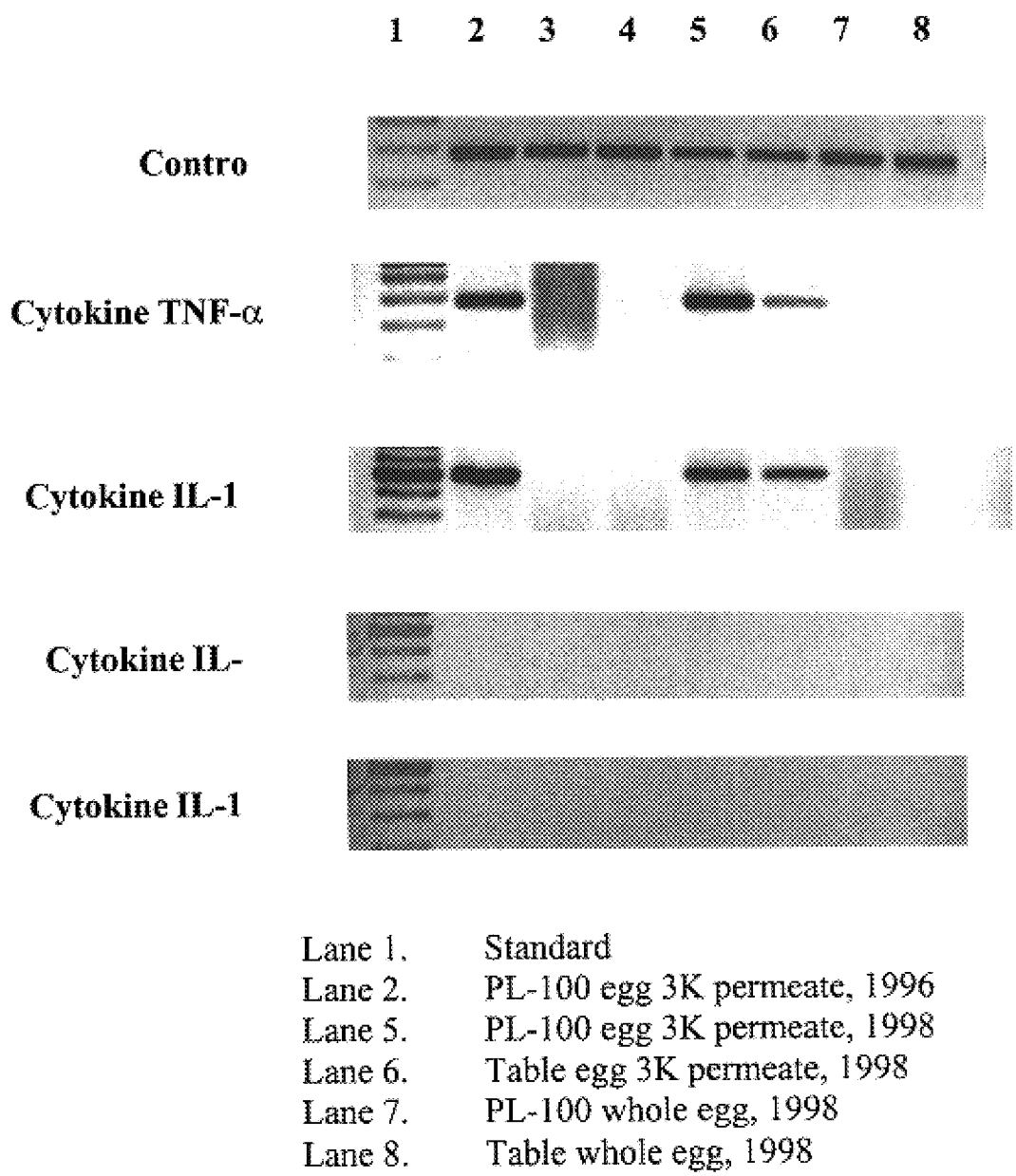
FIG. 1 is a digitized image showing the effect of 3,000 Dalton MW permeate on the induction of cytokines in an in vitro assay.

The present invention generally relates to a novel Cytokine Activating Factor (CAF), to a composition comprising a Cytokine Activating Factor (CAF), and to a method for modulating the immune system using the composition. The composition of the invention can include compositions comprising recombinantly produced CAF, synthetically (i.e., chemically) produced CAF, or purified CAF, and/or a composition of the invention can be a natural food product containing CAF, and preferably, includes a natural food product or fraction thereof which is enriched for the presence of CAF, such as by selection processes or by production of an enriched fraction. Such natural food products include hyperimmune egg products, including fractions of hyperimmune egg products which are enriched for CAF. The present inventors have discovered that the novel protein, CAF, upregulates the expression of tumor necrosis factor α (TNFα), interleukin-6 (IL-6) and interleukin-1β (IL-1β), and downregulates the expression of transforming growth factor β (TGFβ). Therefore, the CAF protein of the present invention can be used to modulate (i.e., regulate) the immune system in general by modulating the expression of these cytokines and the cells which produce or are affected by these cytokines. In addition, since TNFα, IL-1β and IL-6 are typically considered to be proinflammatory cytokines, and since TGFβ is typically considered to be an anti-inflammatory cytokine, the CAF protein of the present invention is useful for the treatment of conditions in which stimulation of an immune response and cells which respond to proinflammatory cytokines is desirable, including, but not limited to, bacterial infection, sepsis and cancer.

The CAF of the present invention was originally discovered by the present inventors to be a component that is produced in hyperimmunized egg products. The preferred immunogen mixture that is administered, preferably by injection, to the egg-producing animals to induce an immune response and to produce the hyperimmune egg product that contains Cytokine Activating Factor of the present invention is not required to contain specific immunogens that are known to modulate the immune system by activating particular cytokines or by inducing production of a factor that induces particular cytokines. Therefore, it is surprising to find such a Cytokine Activating Factor in a hyperimmune egg product obtained from animals immunized against a mixed antigen vaccine, which is expected to be effective in modulating the immune system when administered to a subject. Moreover, prior to the present invention, it was not known that hyperimmunization of egg-producing animals would result in the production of the novel cytokine activating factor of the present invention which would have the properties of being capable of regulating cytokine production and the differentiation of cells of the immune system in an animal. To the present inventors' knowledge, prior to the present invention, the Cytokine Activating Factor described herein had never been identified, purified, characterized, or sequenced.

The Cytokine Activating Factor of the present invention can be separated and highly purified from egg using ultrafiltration, Q Sepharose ion-exchange chromatography, solid phase extraction, partition extraction and reverse-phase $C_{18}$ HPLC technologies (See Example 1). Analytical HPLC, in vitro cytokine expression studies, and bio-assay data have all demonstrated the purification of a biologically active Cytokine Activating Factor. Moreover, as described herein, the Cytokine Activating Factor can be isolated, cloned, and produced recombinantly, or produced synthetically, using the sequence information provided herein.

Definitions

The following definitions apply throughout the application unless otherwise specified:

The term "hyperimmunization" means exposure to one or more immunogens (e.g., antigens) such that an immune response is elevated and maintained above the natural unexposed state.

The term "immunogen" means a substance that is able to induce a humoral antibody and/or a cell-mediated immune response rather than immunological tolerance. The term signifies the ability to stimulate an immune response as well as react with the products of it, e.g., antibody.

The term "combinatorial derived immunogens" refers to a process of generating molecular diversity among immunogens by way of combinatorial synthesis.

The term "bioengineered immunogens" refers to immunogens which are obtained through the process of gene cloning technologies and genetic manipulation or chemical synthesis.

The term "genetic vaccine" refers to a nucleic acid vaccine which is generally produced by recombinant technologies and which may elicit an immune response.

The terms "egg" or "egg product" each mean any whole egg (table, hyperimmunized or otherwise) or any product or fraction derived therefrom.

The terms "table egg" or "table egg product" each mean a whole egg, or any product or fraction derived therefrom, obtained from egg-producing animals which are not maintained in a hyperimmune state.

The terms "hyperimmune egg" or "hyperimmune egg product" each mean whole egg or any product or fraction derived therefrom, obtained from an egg producing animal maintained in a hyperimmune state.

The term "supranormal levels" means levels in excess of those found in eggs of egg-producing animals not maintained in a hyperimmune state.

The term "immunoregulatory egg" means egg or egg fractions containing the Cytokine Activating Factor disclosed herein.

The term "immune response" refers generally to a cell-mediated or cellular immune response (i.e., an immune response mediated by cells of the immune system including T lymphocytes, B lymphocytes and macrophages) and/or a humoral immune response (i.e., an immune response mediated by antibodies).

The term "animal" refers to any species of the kingdom, Animalia. Preferred animals to immunize according to the present invention include any animals of the Vertebrate class, Aves, including, without limitation, chickens, turkeys, and ducks. Preferred animals to treat according to the present invention include any animals of the Vertebrate classes, Aves and Mammalia, including, without limitation, primates, rodents, livestock and domestic pets. Livestock include mammals to be consumed or that produce useful products (e.g., sheep for wool production). Preferred mammals to protect from a disease or condition include humans, dogs, cats, nice, rats, sheep, cattle, horses and pigs, with humans being particularly preferred.

The term "target animal" refers to an animal which functions as an egg-producing animal.

The term "subject animal" refers to the animal which is administered a CAF-containing composition of the present invention, including compositions containing purified CAF, synthetically produced CAF, recombinantly produced CAF, or a CAF-enriched egg or egg product produced by the target animal. A subject animal can also be referenced as a patient.

The term "Cytokine Activating Factor" or "CAF" is used generally to refer to the factor of the present invention at any stage of purity (e.g., including as a component of egg, as a semi-purified protein, as a highly purified protein, as a recombinant protein or as a chemically synthesized protein) and having the biochemical, physical, structural and/or functional characteristics (e.g., biological activity) described herein for Cytokine Activating Factor. It is noted that highly purified CAF according to the present invention can also be referred to as "CAFb" (See Example 1).

The term "highly pure Cytokine Activating Factor" or "highly pure CAF" means a Cytokine Activating Factor of at least of the purity described in Example 1 for CAFb.

The term "Cytokine Activating Factor-enriched" or "CAF-enriched" product or composition refers to a product or composition which has been purified, processed and/or produced to contain a greater level of Cytokine Activating Factor in the enriched, or final product as compared to the level of Cytokine Activating Factor in the product or composition prior to the purification, processing and/or production step. Therefore, in one embodiment, the CAF is present in the initial product or composition, and the steps of purification, processing and/or producing increase the amount of CAF in the product or composition relative to the other components in the product or composition, typically by elimination or reduction in the amount of some of the components from the initial product. In another embodiment, the initial product or composition either does not contain CAF or contains an initial amount of CAF and the CAF-enriched product or composition is produced by adding purified, recombinant or synthetically produced CAF to the initial product or composition. Such CAF-enriched compositions are discussed in more detail below. Other ways of enriching a composition or product for CAF will be apparent to those of skill in the art.

The term "isolated" with regard to a compound (e.g., a protein or nucleic acid molecule of the present invention) refers to a compound that has been removed from its natural milieu (i.e., that has been subject to human manipulation). As such, "isolated" does not reflect the extent to which the compound has been purified.

The term "protein" can be used interchangeably with the term "polypeptide", although the latter term is typically used to refer to relatively small proteins having substantially linear secondary structure. The term "protein" or "polypeptide" includes full-length proteins, fusion proteins, or any homologue of such a protein.

The phrase "homologue of a CAF protein" (i.e., a "CAF homologue") includes CAF proteins in which at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). Preferably, a CAF homologue has CAF biological activity.

The phrase "biologically active" or "biological activity" with reference to a CAF protein of the present invention refers to any functional activity of a CAF protein, and typically, a functional activity of a naturally occurring CAF protein. In particular, reference to the biological activity of a CAF protein preferably refers to the ability of a CAF protein is to upregulate (induce, stimulate, enhance, increase) the expression of a cytokine which includes tumor necrosis factor α (TNFα), interleukin-1β (IL-1β), and/or interleukin-6 (IL-6). It is noted that naturally occurring CAF as described in detail herein can upregulate the expression of each of TNFα, IL-1β, and IL-6. CAF biological activity can also include an ability to downregulate (inhibit, decrease, suppress) the expression of transforming growth factor β (TGFβ). A biological activity of a CAF protein can also include, but is not limited to an ability of CAF to bind to a receptor or to another protein, DNA, a carbohydrate moiety or a lipid moiety, which results in or contributes to one of the above-identified biological activities.

A "biologically active subunit" of a protein is a portion (i.e., fragment, domain or monomer) of the protein which has biological activity of the full-length protein or multimer.

The term "mimetic" is used to refer to any peptide or non-peptide compound that is able to mimic the biological action of a naturally occurring peptide, of ten because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example.

The term "stable" with regard to a protein of the present invention, refers to the ability of a protein to be resistant to degradation caused by increases or decreases in temperature, by increases or decreases in pH, by increases or decreases in salt concentrations, by oxidation and/or reduction, by deamidation, and/or resistant to other forms of chemical degradation and to proteolytic degradation. More specifically, a protein is determined to be stable under any given condition by detection of any measurable level of biological activity of the protein, preferably by detection of the ability of the protein to affect any measurable increase in TNFα, IL-1β or IL-6 expression by a cell. Preferably, a protein that is considered to be stable maintains at least 10% of its biological activity after exposure to a given condition, and more preferably, at least 25%, and more preferably at least 50%, as compared to its biological activity prior to exposure to the condition (e.g., its biological activity under normal conditions). Stability of a protein can refer to the ability of protein to be stable, as described above, either during storage or during use.

The phrase "nucleic acid molecule" primarily refers to the physical nucleic acid molecule and the phrase "nucleic acid sequence" primarily refers to the sequence of nucleotides on the nucleic acid molecule. However, the two phrases can be used interchangeably, especially with respect to a nucleic acid molecule, or a nucleic acid sequence, being capable of encoding a protein.

The phrase "recombinant molecule" or "recombinant nucleic acid molecule" primarily refers to a nucleic acid molecule operatively linked to a transcription control sequence.

The phrase "operatively linked" refers to linking a nucleic acid molecule to a transcription control sequence in a manner such that the molecule is able to be expressed when transfected (i.e., transformed, transduced, transfected, conjugated or conduced) into a host cell.

The phrase "transcription control sequence" refers to any sequences which control the initiation, elongation, and termination of transcription. Particularly important transcription control sequences are those which control transcription initiation, such as promoter, enhancer, operator and repressor sequences.

The term "transfection" is used to refer to any method by which an exogenous nucleic acid molecule (i.e., a recombinant nucleic acid molecule) can be inserted into the cell. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection". However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass both transfection of animal cells and transformation of microbial cells, to the extent that the terms pertain to the introduction of exogenous nucleic acids into a cell. Therefore, transfection techniques include, but are not limited to, transformation, electroporation, microinjection, lipofection, adsorption, infection and protoplast fusion.

The term "contiguous" or "consecutive", with regard to nucleic acid or amino acid sequences described herein, are use interchangeably and refer to being connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

Reference to a percent (%) identity, unless otherwise specified, refers to an evaluation of homology between two or more amino acid or nucleic acid sequences which is performed using: (1) a BLAST 2.0 Basic BLAST homology search (http://www.ncbi.nlm.nih.gov/BLAST), using blastp for amino acid searches and blastn for nucleic acid searches with standard default parameters, wherein the query sequence is filtered for low complexity regions by default (described in Altschul, S. F., Madden, T. L., Schäaffer, A. A., Zhang, J., Zhang, Z., Miller, W. & Lipman, D. J. (1997) "Gapped BLAST and PSI-BLAST: anew generation of protein database search programs." Nucleic Acids Res.

25:3389–3402, incorporated herein by reference in its entirety); (2) a BLAST 2 alignment (using the parameters described below) (http://www.ncbi.nlm.nih.gov/BLAST); or (3) both BLAST 2.0 and BLAST 2. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. Therefore, it is to be understood that percent identity can be determined by using either one or both of these programs, but preferably, using BLAST 2.0 Basic BLAST. Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174:247–250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows:

For blastn, using 0 BLOSUM62 matrix:
Reward for match=1
Penalty for mismatch=−2
Open gap (5) and extension gap (2) penalties
gap x_dropoff (50) expect (10) word size (11) filter (on)

For blastp, using 0 BLOSUM62 matrix:
Open gap (11) and extension gap (1) penalties
gap x_dropoff (50) expect (10) word size (3) filter (on).

Reference to "hybridization conditions" refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety. One of skill in the art can use the formulae in Meinkoth et al., ibid. to calculate the appropriate hybridization and wash conditions to achieve particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. By way of example, in particular embodiments, stringent hybridization conditions for DNA:DNA hybrids include hybridization at an ionic strength of 6× SSC (0.9 M Na⁺) at a temperature of between about 20° C. and about 35° C. (e.g., less stringent conditions), more preferably, between about 28° C. and about 40° C. (e.g., more stringent conditions), and even more preferably, between about 35° C. and about 45° C. (even more stringent conditions). In particular embodiments, stringent hybridization conditions for DNA:RNA hybrids include hybridization at an ionic strength of 6×SSC (0.9 M Na⁺) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62.

Reference to "low stringency hybridization" (and washing conditions) refers to conditions which permit isolation of nucleic acid molecules having at least about 40% nucleic acid sequence identity with the nucleic acid molecule being used to probe in the hybridization reaction (i.e., conditions permitting about 60% or less mismatch of nucleotides as determined using formulae in Meinkoth et al., ibid.).

Reference to "moderate stringency hybridization" (and washing conditions) refer to conditions which permit isolation of nucleic acid molecules having at least about 60% nucleic acid sequence identity with the nucleic acid molecule being used to probe in the hybridization reaction (i.e., conditions permitting about 40% or less mismatch of nucleotides as determined using formulae in Meinkoth et al., ibid.).

Reference to "high stringency hybridization" (and washing conditions) refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides as determined using formulae in Meinkoth et al., ibid.).

Reference to "very high stringency hybridization" (and washing conditions) refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides as determined using formulae in Meinkoth et al., ibid.).

The term "modulate" or derivatives of such term, means to change, regulate or vary from one state to another, and includes a measurable or observable increase or decrease in any measurable characteristic and/or a change from one characteristic to another, different characteristic.

The phrase "pharmaceutically acceptable carrier" refers to pharmaceutically acceptable excipients, formulations and/or pharmaceutically acceptable delivery vehicles, which are suitable for use in administration of a composition of the present invention to a suitable in vitro, ex vivo or in vivo site. Pharmaceutically acceptable carriers can enable compositions of the present invention to be produced/provided in any suitable form for use, including, but not limited to, a liquid, an aerosol, a capsule, a tablet, a pill, a powder, a gel and a granule. Some pharmaceutically acceptable carriers include cells, membranes, lipid formulations (including liquids that, upon administration to a patient, form a solid or a gel in situ), antibody formulations, food products (e.g., any edible product or preparation) and recombinant viruses. Preferred carriers are also biodegradable (i.e., bioerodible).

A "pharmaceutically acceptable excipient" includes excipients or formulations that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, or o-cresol, formalin and benzol alcohol.

A "controlled release vehicle" is a type of pharmaceutically acceptable carrier that is capable of releasing a composition or protein of the present invention in a controlled manner into a patient or culture. A controlled release formulation comprises a compound of the present invention (e.g., a CAF protein (including homologues), an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphere, and transdermal delivery systems.

A "pharmaceutically acceptable delivery vehicle" is a pharmaceutically acceptable carrier which is capable of delivering a composition or protein of the present invention to a target site. Preferably, pharmaceutically acceptable delivery vehicle is capable of targeting (i.e., directing, selectively delivering) the composition to the target site. A "target site" refers to a site in a patient to which one desires to deliver a composition. For example, a target site can be any cell or tissue which is targeted by direct injection or delivery using artificial and natural lipid-containing delivery vehicles (e.g., liposomes), antibodies, viral vectors or other delivery vehicles, including ribozymes. Natural lipid-containing delivery vehicles include cells and cellular membranes. Artificial lipid-containing delivery vehicles include liposomes and micelles. When the compound is a protein (e.g., a CAF protein), suitable delivery vehicles include, but are not limited to, antibodies, liposomes and cells (e.g., a recombinant cell expressing the protein). When the compound is a recombinant nucleic acid molecule, suitable delivery vehicles include, but are not limited to liposomes, viral vectors, gold particles, poly-L-lysine/DNA-molecular conjugates, artificial chromosomes or other delivery vehicles, including ribozymes.

The term "liposome" refers to a delivery vehicle comprising a lipid composition that is capable of delivering a nucleic acid molecule or protein to a particular, or selected, site in a patient. A liposome comprises a lipid composition that is capable of fusing with the plasma membrane of the targeted cell to deliver a nucleic acid molecule into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule of the present invention can be achieved using methods standard in the art.

The term "viral vector" refers to an isolated nucleic acid molecule useful in the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

The term "administer" means any method of providing a subject with a substance (e.g., introducing a substance into a subject), including by in vivo or ex vivo administration. Methods of in vivo administration include, but are not limited to, intravenous administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, intraocular, pulmonary administration, impregnation of a catheter, by suppository and direct injection into a tissue. Ex vivo refers to performing part of the regulatory step outside of the patient, such as by transfecting a population of cells removed from a patient with a recombinant molecule comprising a nucleic acid sequence encoding a CAF protein according to the present invention under conditions such that the recombinant molecule is subsequently expressed by the transfected cell, and returning the transfected cells to the patient. Methods to achieve such transfection include, but are not limited to, transfection, viral infection, electroporation, lipofection, bacterial transfer, spheroplast fusion, and adsorption. Ex vivo methods are particularly suitable when the target cell can easily be removed from and returned to the patient.

The term "therapeutic benefit" does not necessarily refer to a cure for a particular disease or condition, but rather, preferably encompasses a result which can include alleviation of the disease or condition, elimination of the disease or condition, reduction of a symptom associated with the disease or condition, prevention or alleviation of a secondary disease or condition resulting from the occurrence of a primary disease or condition (e.g., metastatic cancer resulting from primary cancer), and/or prevention of the disease or condition.

The term "protection" with reference to a disease or condition refers to reducing the symptoms of the disease; reducing the occurrence of the disease, and/or reducing the severity of the disease. Protecting a patient or subject can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment).

The term "prevention" means that the progression of the disease is reduced and/or eliminated, or that the onset of the disease is eliminated (prophylactic treatment).

The term "treatment" means that the onset of the symptoms (including pain) of the disorder and/or pathogenic origin of the disorder be delayed, reduced, or completely prevented, or, if present, the symptoms be ameliorated or completely eliminated. For example, the CAF composition treats cancer not only by suppressing the symptoms of the disorder in humans and other mammals, but also by acting as a prophylactic agent to counteract the presence of the disorder in the recipient.

The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

The term "a" or "an" entity refers to one or more of that entity. As such, the terms "a" (or "an"), "one or more" and "at least one" can be used interchangeably herein.

The terms "comprising", "including", and "having" can be used interchangeably.

DESCRIPTION OF THE INVENTION

One embodiment of the present invention relates to an isolated Cytokine Activating Factor (CAF) protein. Reference to an isolated CAF protein includes full-length proteins, truncated proteins (i.e., fragments of a full-length proteins), fusion proteins, or any homologue of such a protein. CAF homologues have been defined above. Preferably, a CAF homologue has CAF biological activity, also defined above. Specifically, a CAF protein of the present invention preferably has a biological activity which includes an ability to upregulate (increase, stimulate, induce, enhance) expression of tumor necrosis factor α (TNFα), interleukin-1β (IL-1β) and/or interleukin-6 (IL-6) and/or an ability to downregulate (decrease, inhibit, prevent, reduce) expression of transforming growth factor β (TGFβ). Such biological activity can be measured by any suitable method of measuring cytokine activity in the art, including, but not limited to, immunoassays (including enzyme linked immunosorbent assays, or ELISA), radioimmunoassays, and RNA assays (See Examples). A biological activity of a CAF protein can also include, but is not limited to: an ability of CAF to bind to a receptor or to another protein, DNA, a carbohydrate moiety or a lipid moiety, which results in or contributes to one of the above-identified biological activities. Methods of measuring the ability of a protein to bind to another moiety are well within the ability of one of skill in the art. Moreover, using the guidance provided herein, it is within the ability of one of skill in the art to make modifications in the nucleic acid and/or amino acid sequence of wild-type CAF (e.g., amino acid SEQ ID NOs:1 or 6) and to test homologues having such modifications for one or more biological activities of CAF. For example, methods for determining the ability of CAF to induce or inhibit cytokine expression are described in the Examples section.

Reference to an isolated CAF protein can include a CAF protein which has been substantially purified from a natural source (e.g., a hyperimmune egg according to the present invention), recombinantly produced CAF and/or synthetically produced CAF. A particularly preferred CAF protein of the present invention comprises an amino acid sequence selected from SEQ ID NO:1 and/or SEQ ID NO:6. SEQ ID NO:1 spans from amino acids 1–30 of SEQ ID NO:6 and is an N-terminal fragment of SEQ ID NO:6. SEQ ID NO:6 is believed to be the full-length amino acid sequence of a CAF protein of the present invention which was purified from hyperimmune egg.

In one embodiment, a CAF protein includes proteins having an amino acid sequence comprising at least 9 contiguous amino acid residues of SEQ ID NO:1 or SEQ ID NO:6, (i.e., 9 contiguous amino acid residues having 100% identity with 9 contiguous amino acids of SEQ ID NO:1 or SEQ ID NO:6). Such a protein can be referred to as a homologue of a protein comprising SEQ ID NO:1 and/or SEQ ID NO:6 (e.g., a CAF homologue), but also includes proteins comprising SEQ ID NO:1 and/or SEQ ID NO:6 (e.g., naturally occurring CAF proteins). In a preferred embodiment, a homologue of a CAF protein comprises an amino acid sequence comprising at least 12, and more preferably at least about 15, and more preferably at least about 20, and more preferably at least about 25 contiguous amino acid residues of SEQ ID NO:1 and/or SEQ ID NO:6. In another preferred embodiment, a CAF homologue comprises an amino acid sequence comprising at least about 30, and more preferably at least about 35, and more preferably at least about 40, and even more preferably, at least about 45, and more preferably at least about 50, and more preferably at least about 55, and more preferably at least about 60 and more preferably at least about 65, contiguous amino acid residues of SEQ ID NO:6.

A CAF protein homologue can include proteins encoded by a nucleic acid sequence comprising at least 27, and preferably at least 36, and more preferably at least 45, and more preferably at least 60, and more preferably at least 75, contiguous nucleotides of a nucleic acid sequence encoding SEQ ID NO:1 and/or SEQ ID NO:6. In another embodiment, a CAF protein homologue can include proteins encoded by a nucleic acid sequence comprising at least 90, and more preferably at least 105, and more preferably at least 120, and more preferably at least 135, and more preferably at least 150, and more preferably at least 165, and more preferably at least 180 and more preferably at least 195, contiguous nucleotides of a nucleic acid sequence encoding SEQ ID NO:6.

As discussed above, a CAF protein homologue preferably has measurable CAF biological activity (i.e., has biological activity). However, in some embodiments, a CAF protein, including a CAF homologue, or the nucleic acid encoding such protein or homologue, is used for the preparation of antibodies or the development of oligonucleotides, respectively, useful for identifying CAF and CAF-related proteins and nucleic acid sequences (e.g., for the purpose of screening/selecting hyperimmune egg products for CAF-enriched fractions in the case of antibodies or oligonucleotides), for cloning the nucleic acid sequence encoding CAF (in the case of oligonucleotides), and/or for identifying proteins or nucleic acids which bind to CAF or its nucleic acid sequence, respectively. In these embodiments, whether the CAF protein has biological activity is not particularly relevant, other than to the extent that a CAF protein useful for such methods intrinsically has CAF biological activity.

In one embodiment, a CAF protein (e.g., a CAF protein homologue) comprises an amino acid sequence that is at least about 65% identical to SEQ ID NO:1 and/or SEQ ID NO:6 over at least about 15 contiguous amino acids, and more preferably over at least about 20 amino acids, and more preferably over at least about 25 amino acids of SEQ ID NO:1 and/or SEQ ID NO:6, respectively. Preferably, a CAF protein comprises an amino acid sequence that is at least about 70%, and more preferably, at least about 75%, and more preferably, at least about 80%, and more preferably at least about 85%, and more preferably at least about 90%, and even more preferably at least about 95% identical to SEQ ID NO:1 and/or SEQ ID NO:6 over at least about 15 amino acids, and more preferably over at least about 20 amino acids, and more preferably over at least about 25 amino acids of SEQ ID NO:1 and/or SEQ ID NO:6, respectively. In another embodiment, a CAF protein comprises an amino acid sequence that is at least about 65%, and more preferably at least about 70%, and more preferably, at least about 75%, and more preferably, at least about 80%, and more preferably at least about 85%, and more preferably at least about 90%, and even more preferably at least about 95% identical to SEQ ID NO:6 over at least about 30 amino acids, and more preferably over at least about 35 amino acids and more preferably over at least about 40 amino acids, and more preferably over at least about 45 amino acids and more preferably over at least about 50 amino acids and more preferably over at least about 55 amino acids, and even more preferably over at least about 60 amino acids of SEQ ID NO:6.

In another embodiment, a CAF protein comprises an amino acid sequence that is at least about 60% identical to SEQ ID NO:6 over at least 66 amino acids, and more preferably over at least about 67 amino acids, and more preferably over at least about 68 amino acids, and more preferably over at least about 69 amino acids of SEQ ID NO:6. Preferably, a CAF protein comprises an amino acid sequence that is at least about 65%, and more preferably at least about 70%, and more preferably at least about 75%, and more preferably, at least about 80%, and more preferably at least about 85%, and more preferably at least about 90%, and even more preferably at least about 95% identical to SEQ ID NO:6 over at least 66 amino acids, and more preferably over at least about 67 amino acids, and more preferably over at least about 68 amino acids, and more preferably over at least about 69 amino acids of SEQ ID NO:6. Methods to determine percent identity are described above.

In another embodiment, a CAF protein, including a CAF protein homologue, includes a protein having an amino acid sequence that is sufficiently similar to a natural CAF amino acid sequence that a nucleic acid sequence encoding the homologue is capable of hybridizing under moderate, high or very high stringency conditions (described above) to (i.e., with) a nucleic acid molecule encoding the natural CAF protein (i.e., to the complement of the nucleic acid strand encoding the natural CAF amino acid sequence). Such conditions are defined above. Preferably, a homologue of a CAF protein is encoded by a nucleic acid molecule comprising a nucleic acid sequence that hybridizes under moderate, high or very high stringency conditions to the complement of a nucleic acid sequence that encodes a protein comprising an amino acid sequence represented by SEQ ID NO:1 or SEQ ID NO:6. A nucleic acid sequence complement of nucleic acid sequence encoding a CAF protein of the present invention refers to the nucleic acid sequence of the nucleic acid strand that is complementary to the strand which encodes CAF. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes the amino acid sequence SEQ ID NO:1 and/or SEQ ID NO:6, and/or with the complement of the nucleic acid sequence that encodes an amino acid sequence SEQ ID NO:1 and/or SEQ ID NO:6. Methods to deduce a complementary sequence are known to those skilled in the art. It should be noted that since amino acid sequencing and nucleic acid sequencing technologies are not entirely error-free, the sequences presented herein, at best, represent apparent sequences of a CAF protein of the present invention.

CAF protein homologues can be the result of natural allelic variation or natural mutation. CAF protein homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding CAF is a gene that occurs at essentially the same locus (or loci) in the genome as the gene which encodes an amino acid sequence SEQ ID NO:1 and/or SEQ ID NO:6, but which, due to natural variations caused by, for example, mutation or recombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art and would be expected to be found within a given bacterial species since the genome is haploid and/or among a group of two or more bacterial species.

CAF proteins also include expression products of gene fusions (for example, used to overexpress soluble, active forms of the recombinant protein), of mutagenized genes (such as genes having codon modifications to enhance gene transcription and translation), and of truncated genes (such as genes having domains removed to generate biologically active fragments or subunits of full-length protein). It is noted that CAF proteins and protein homologues of the present invention include proteins which do not have CAF activity. Such proteins are useful, for example, for the production of antibodies.

An isolated CAF protein of the present invention, including full-length proteins, truncated proteins, other homologues, and fusion proteins, can be identified in a straight-forward manner: (1) by the protein's ability to upregulate expression of TNFα, IL-1β and/or IL-6, and/or to downregulate TGFβ, such as is illustrated in the Examples; (2) by the biochemical and structural properties of the protein (e.g., molecular weight, primary structure, stability characteristics); (3) by the protein's selective binding to an antibody against a CAF protein; and/or (4) by homology of the protein with other CAF amino acid and nucleic acid sequences such as to CAF amino acid and nucleic acid sequence from other sources than a hyperimmune egg. The minimum size of a protein and/or homologue of the present invention is a size sufficient to have CAF biological activity or, when the protein is not required to have such activity, sufficient to be useful for another purpose associated with a CAF protein of the present invention, such as for the production of antibodies that bind to a naturally occurring CAF protein. As such, the minimum size of a CAF protein or homologue of the present invention is a size suitable to form at least one epitope that can be recognized by an antibody, and is typically at least 8 to 30 amino acids in length (including any length in between 8 and 30 in increments of one amino acid), with preferred sizes depending on whether full-length, multivalent (i.e., fusion protein having more than one domain each of which has a function), or functional portions of such proteins are desired. There is no limit, other than a practical limit, on the maximum size of such a protein in that the protein can include a portion of a CAF protein (including CAF homologues) or a full-length CAF.

The present invention also includes a fusion protein that includes a CAF-containing domain (including a homologue of a CAF protein) attached to one or more fusion segments. Suitable fusion segments for use with the present invention include, but are not limited to, segments that can: enhance a protein's stability; provide other desirable biological activity (e.g., a cytokine); and/or assist with the purification of a CAF protein (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the CAF-containing domain of the protein and can be susceptible to cleavage in order to enable straight-forward recovery of a CAF protein. Fusion proteins are preferably produced by culturing a recombinant cell transfected with a fusion nucleic acid molecule that encodes a protein including the fusion segment attached to either the carboxyl and/or amino terminal end of a CAF-containing domain.

The present invention also includes a mimetic of a CAF protein. As used herein, the term "mimetic" is used to refer to any peptide or non-peptide compound that is able to mimic the biological action of a naturally occurring peptide, of ten because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example.

Such mimetics can be designed, selected and/or otherwise identified using a variety of methods known in the art. Various methods of drug design, useful to design mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety. A CAF mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

According to the present invention, CAF proteins can be derived from any animal, and particularly, from any animal in the Vertebrate classes, Mammalia or Aves. Preferably, CAF proteins are derived from an egg-producing animal from the Vertebrate class, Aves. Preferred CAF proteins include isolated CAF proteins from hyperimmunized chickens, turkeys, or ducks. A particularly preferred isolated CAF protein is a CAF protein derived from hyperimmunized chicken eggs.

As discussed above, a CAF protein of the present invention may be produced by any method suitable for the production of proteins or polypeptides. A particularly preferred method for production of a CAF protein of the present invention is by chemical synthesis methods. For example, such methods include well known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, *Methods Enzymol.* 289:3–13; Wade et al., 1993, *Australas Biotechnol.* 3(6):332–336; Wong et al., 1991, *Experientia* 47(11–12):1123–1129; Carey et al., 1991, *Ciba Found Symp.* 158:187–203; Plaue et al., 1990, *Biologicals* 18(3): 147–157; Bodanszky, 1985, *Int. J. Pept. Protein Res.* 25(5):449–474; or H. Dugas and C. Penney, BIOORGANIC CHEMISTRY, (1981) at pages 54–92, all of which are incorporated herein by reference in their entirety. For example, peptides may be synthesized by solid-phase methodology utilizing a commercially available peptide synthesizer and synthesis cycles supplied by the manufacturer. One skilled in the art recognizes that the solid phase synthesis could also be accomplished using the FMOC strategy and a TFA/scavenger cleavage mixture.

If larger quantities of a CAF protein are desired, the protein can be produced using recombinant DNA technology, although for proteins of this smaller size (i.e., peptides), peptide synthesis may be generally preferred. A protein can be produced recombinantly by culturing a cell capable of expressing the protein (i.e., by expressing a recombinant nucleic acid molecule encoding the protein, described in detail below) under conditions effective to produce the protein, and recovering the protein. Effective culture conditions include, but are not limited to, effective media, bioreactor, temperature, pH and oxygen conditions that permit protein production. An effective medium refers to any medium in which a cell is cultured to produce a CAF protein of the present invention. Such medium typically comprises an aqueous medium having assimilable carbon, nitrogen and phosphate sources, and appropriate salts, minerals, metals and other nutrients, such as vitamins. Recombinant cells (i.e., cells expressing a nucleic acid molecule encoding a CAF protein) can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Such techniques are well known in the art and are described, for example, in Sambrook et al., 1988, Molecular Cloning: A Laboratory Manual, Cold Spring Harbor Press, Cold Spring Harbor Laboratory, Cold Spring Harbor, N.Y. or Current Protocols in Molecular Biology (1989) and supplements.

Depending on the vector and host system used for production, resultant recombinant CAF proteins of the present invention may either remain within the recombinant cell; be secreted into the culture medium; be secreted into a space between two cellular membranes, such as the periplasmic space in *E. coli*; or be retained on the outer surface of a cell or viral membrane. The phrase "recovering the protein" refers to collecting the whole culture medium containing the protein and need not imply additional steps of separation or purification. CAF proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a biocatalyst, other reagent, or for administration to a subject. For example, a water-soluble fraction comprising CAF as described in Example 1 is considered to be substantially pure and is suitable for administration to a patient.

In yet another embodiment, a CAF protein of the present invention can be highly purified from a suitable source, including, but not limited to, the egg of an avian that has been hyperimmunized with one or more immunogens, and, in particular, bacterial antigens or their synthetic equivalents. The present inventors have discovered that the Cytokine Activating Factor of the present invention is present in hyperimmune eggs at supranormal levels. The highly purified egg Cytokine Activating Factor can be isolated from whole egg, egg yolk and egg white. The CAF highly purified from egg yolk shows higher immunoregulatory activity than CAF highly purified from egg white.

The large-scale purification process of the CAF from egg typically employs 40 kg of hyperimmune egg yolk (e.g., PL-100 or S-100 egg yolk described in U.S. Pat. No. 5,772,999) as a starting point. The CAF is highly purified by using the technologies of ultrafiltration, Q Sepharose ion-exchange chromatography, solid phase extraction, and additional methods as described briefly below and in detail in the Examples section.

The Cytokine Activating Factor can be highly purified from whole egg, egg yolk or egg white. An example of a preferred high purification process is as follows:

1. Egg yolk delipidation;
2. Egg yolk 3000 Dalton MW permeate preparation;
3. Separation of fractions by ion or anion exchange chromatography;
4. Solid phase extraction;
5. Partition extraction of solid phase extraction fraction;
6. HPLC separation; and
7. Bioassay for cytokine induction activity.

The following is a more detailed description of this process:

Step 1

The Cytokine Activating Factor can be highly purified from whole egg, egg yolk or egg white. In a preferred embodiment, the composition is purified from egg yolk. The lipid portion is removed from the whole egg or egg yolk by methods well-known to those having skill in the art. For example, in the case of spray-dried egg yolk powder, defatting can be accomplished with solvents (propane, butane or hexane or with binary solvents), supercritical $CO_2$, enzymes and the like, and in the case of liquid egg yolk, defatting can be accomplished by the caprylic acid separation method (CAPS) disclosed by Lee (U.S. Pat. No. 5,367,054). No fat removal is necessary for egg white, and thus the liquid or powdered form of the egg white can be either heated or dissolved directly by conventional methods and as described in the examples listed below. The whole egg, egg yolk or egg white is then preferably processed into either liquid or powder form, and is further processed to obtain water soluble fractions. (See Examples)

Step 2

The resulting water soluble fractions, from whole egg, egg yolk or egg white, are subjected to ultrafiltration using ultrafiltration systems equipped with a 3,000 Dalton molecular weight cut-off membrane. The ultrafiltration process separates molecules having a molecular weight of more than approximately 3,000 Dalton from those having a molecular weight of less than approximately 3000 Dalton. It is noted that the 3000 Dalton cut-off is approximate, since significantly larger proteins can pass through the filter if the secondary structure is permitting (i.e., substantially linear polypeptides/proteins). Once filtered, the resulting ultrafiltrates contain molecules of less than approximately 3,000 Dalton molecular weight (or larger, substantially linear polypeptides), which are then lyophilized, weighed, and prepared for bioassay testing and further separation.

Steps 3–7

These steps are set forth in detail in Example 1 and the figures and will not be repeated here.

The highly pure Cytokine Activating Factor of the present invention has the following physical/chemical characteristics (i.e., identifying characteristics):

a. has at least one biologically active subunit which passes through a 3000 Dalton molecular weight cut-off ultrafiltration filter;

b. is stable (i.e., has measurable biological activity) at a temperature up to at least about 50° C.;

c. is stable (i.e., has measurable biological activity) at a pH of from about 2 to about 10;

d. is water soluble;

e. is non-steroidal;

f. is negatively charged;

g. is substantially non-polar; and, h. has a $\lambda_{max}$ at about 254 nm.

In addition, the highly pure Cytokine Activating Factor of the present invention has the following biochemical/functional characteristics:

a. has immunoregulatory activity in a subject animal;

b. is present in both the egg white and egg yolk of avian eggs;

c. when isolated from egg yolk, typically has greater immunoregulatory activity than when isolated from egg white;

d. induces cytokine expression in vitro, and particularly, induces tumor necrosis factor α (TNFα), interleukin-1β (IL-1β) and/or interleukin-6 (IL-6) expression in vitro; and/or e. downregulates expression of transforming growth factor β (TGFβ).

Additionally, the CAF protein of the present invention may have the ability to induce differentiation of cells of the macrophage and/or monocyte lineage.

The 3,000 Dalton molecular weight is deduced from the isolation and purification of the composition wherein the isolation and purification process uses an ultra-filtration membrane that does not allow the passage of molecular species greater than 3,000 Dalton therethrough. The highly purified Cytokine Activating Factor was initially suspected to be non-proteinaceous and non-steroidal because it is small in size and is not degraded by enzymes which degrade proteins (based on in vivo assay wherein the protein exhibited biological activity after being administered orally, and thus exposed to digestive enzymes). Moreover, the composition is orally active. Without being bound by theory, the present inventors believe that the small stable form of the highly purified Cytokine Activating Factor (as differentiated from most proteins which are much larger) facilitates its absorption from the digestive tract. Finally, the highly purified Cytokine Activating Factor is heat-stable, a characteristic not typically found in most proteins. However, it is now known that the highly purified Cytokine Activating Factor is indeed a protein which has the above-identified stability characteristics. Such a discovery was surprising and further demonstrates the advantages of the Cytokine Activating Factor of the present invention as being highly suitable for inclusion in formulations, processed foods, and vaccines, including oral vaccines and formulations.

Further embodiments of the present invention include nucleic acid molecules that encode a CAF protein. A nucleic acid molecule of the present invention includes a nucleic acid molecule comprising a nucleic acid sequence encoding any of the isolated CAF proteins, including a CAF homologue, described above. A preferred CAF nucleic acid molecule of the present invention comprises a nucleic acid sequence encoding a protein comprising an amino acid sequence comprising at least 9, and more preferably at least 12, and more preferably at least about 15, and more preferably at least about 20, and more preferably at least about 25 contiguous amino acid residues of SEQ ID NO:1 and/or SEQ ID NO:6. In another embodiment, a preferred CAF nucleic acid molecule comprises a nucleic acid sequence encoding a protein comprising an amino acid sequence comprising at least about 30, and more preferably at least about 35, and more preferably at least about 40, and even more preferably, at least about 45, and more preferably at least about 50, and more preferably at least about 55, and more preferably at least about 60 and more preferably at least about 65, contiguous amino acid residues of SEQ ID NO:6.

In one embodiment, such nucleic acid molecules include isolated nucleic acid molecules that hybridize under moderate stringency conditions, and more preferably under high stringency conditions, and even more preferably under very high stringency conditions, with the complement of a nucleic acid sequence encoding a naturally occurring CAF (i.e., including naturally occurring allelic variants encoding a CAF). Preferably, an isolated nucleic acid molecule encoding a CAF protein of the present invention comprises a nucleic acid sequence that hybridizes under moderate, high or very high stringency conditions to the complement of a nucleic acid sequence that encodes a protein comprising an amino acid sequence represented by SEQ ID NO:1 and/or SEQ ID NO:6.

In one embodiment of the present invention, a nucleic acid molecule encoding a CAF protein of the present invention comprises a nucleic acid sequence that encodes an amino acid sequence that is at least about 65% identical to SEQ ID NO:1 and/or SEQ ID NO:6 over at least about 15 contiguous amino acids, and more preferably over at least about 20 amino acids, and more preferably over at least about 25 amino acids of SEQ ID NO:1 and/or SEQ ID NO:6, respectively. Preferably, a nucleic acid molecule encoding a CAF protein of the present invention comprises a nucleic acid sequence that encodes an amino acid sequence that is at least about 70%, and more preferably, at least about 75%, and more preferably, at least about 80%, and more preferably at least about 85%, and more preferably at least about 90%, and even more preferably at least about 95% identical to SEQ ID NO:1 and/or SEQ ID NO:6 over at least about 15 amino acids, and more preferably over at least about 20 amino acids, and more preferably over at least about 25 amino acids of SEQ ID NO:1 and/or SEQ ID NO:6, respectively. In one embodiment, a nucleic acid molecule encoding a CAF protein of the present invention comprises a nucleic acid sequence that encodes an amino acid sequence that is at least about 65%, and more preferably at least about 70%, and more preferably, at least about 75%, and more preferably, at least about 80%, and more preferably at least about 85%, and more preferably at least about 90%, and even more preferably at least about 95% identical to SEQ ID NO:6 over at least about 30 amino acids, and more preferably over at least about 35 amino acids and more preferably over at least about 40 amino acids, and more preferably over at least about 45 amino acids and more preferably over at least about 50 amino acids and more preferably over at least about 55 amino acids and even more preferably over at least about 60 amino acids of SEQ ID NO:6.

In another embodiment, a nucleic acid molecule encoding a CAF protein of the present invention comprises a nucleic acid sequence that encodes an amino acid sequence that is at least about 60% identical to SEQ ID NO:6 over at least 66 amino acids, and more preferably over at least about 67 amino acids, and more preferably over at least about 68 amino acids, and more preferably over at least about 69 amino acids of SEQ ID NO:6. Preferably, a nucleic acid molecule encoding a CAF protein of the present invention comprises a nucleic acid sequence that encodes an amino acid sequence that is at least about 65%, and more preferably at least about 70%, and more preferably at least about 75%, and more preferably, at least about 80%, and more preferably at least about 85%, and more preferably at least about 90%, and even more preferably at least about 95% identical to SEQ ID NO:6 over at least 66 amino acids, and more preferably over at least about 67 amino acids, and more preferably over at least about 68 amino acids, and more preferably over at least about 69 amino acids of SEQ ID NO:6. Methods to determine percent identity are described above.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. Isolated CAF nucleic acid molecules can include, for example, CAF genes, natural allelic variants of CAF genes, CAF coding regions or portions thereof, and CAF coding and/or regulatory regions modified by nucleotide insertions, deletions, substitutions, and/or inversions in a manner such that the modifications do not substantially interfere with the nucleic acid molecule's ability to encode a CAF protein of the present invention or to form stable hybrids under stringent conditions with natural gene isolates. An isolated nucleic acid molecule of the present invention does not include naturally occurring molecules larger than a CAF gene. Therefore, chromosomes and molecules containing a CAF gene plus additional flanking sequences are not encompassed by the present invention. The minimum size of a nucleic acid molecule of the present invention is a size sufficient to encode a protein having CAF biological activity, sufficient to encode a CAF protein comprising at least one epitope which binds to an antibody, or sufficient to form a probe or oligonucleotide primer that is capable of forming a stable hybrid with the complementary sequence of a nucleic acid molecule encoding a natural CAF protein (e.g., under low, moderate or high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich.

An isolated CAF nucleic acid molecule can include degeneracies. As used herein, nucleotide degeneracies refers to the phenomenon that one amino acid can be encoded by different nucleotide codons. Thus, the nucleic acid sequence of a nucleic acid molecule that encodes a CAF protein of the present invention can vary due to degeneracies. It is noted that an isolated CAF nucleic acid molecule of the present invention is not necessarily required to encode a protein having CAF activity. A CAF nucleic acid molecule can encode a truncated, mutated or inactive protein, for example. Such nucleic acid molecules and the proteins encoded by such nucleic acid molecules are useful in cloning other CAF-encoding nucleic acid molecules, in detecting the presence of CAF in a sample, for example, or for other purposes such as antibody production.

According to the present invention, reference to a CAF gene includes all nucleic acid sequences related to a natural (i.e. wild-type) CAF gene, such as regulatory regions that control production of the CAF protein encoded by that gene (such as, but not limited to, transcription, translation or post-translation control regions) as well as the coding region itself. In another embodiment, an CAF gene can be a naturally occurring allelic variant that includes a similar but not identical sequence to the nucleic acid sequence encoding a given CAF protein.

An isolated CAF nucleic acid molecule of the present invention can be isolated from its natural source or produced using recombinant DNA technology (e.g., polymerase chain reaction (PCR) amplification, cloning) or chemical synthesis. Methods for producing synthetic nucleic acid molecules are well known in the art. For example, since the CAF proteins are relatively small proteins, the DNA sequence encoding the desired protein may be generated using conventional, commercially available DNA synthesizing apparatus. Alternatively, DNA encoding the desired protein may also be created by using polymerase chain reaction (PCR) techniques or other cloning techniques from genomic DNA of many species, and particularly, from the eggs of egg-producing animals. Such methodologies are well known in the art (Sambrook et al., supra).

A CAF nucleic acid molecule homologue (i.e., encoding a CAF protein homologue) can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof . Another method for modifying a recombinant nucleic acid molecule encoding a CAF protein is gene shuffling (i.e., molecular breeding) (See, for example, U.S. Pat. No. 5,605,793 to Stemmer; Minshull and Stemmer; 1999, *Curr. Opin. Chem. Biol.* 3:284–290; Stemmer, 1994, *P.N.A.S. USA* 91:10747–10751, all of which are incorporated herein by reference in their entirety). This technique can be used to efficiently introduce multiple simultaneous positive changes in the CAF protein action. Nucleic acid molecule homologues can be selected by hybridization with a CAF gene or by screening the function of a protein encoded by a nucleic acid molecule (e.g., ability to increase B cell proliferation).

Preferably, a nucleic acid molecule is part of a recombinant nucleic acid molecule. Such a recombinant nucleic acid molecule comprises an expression vector operatively linked to the nucleic acid molecule. Recombinant nucleic acid molecules are described in detail below. In this embodiment, the CAF protein encoded by the nucleic acid molecule preferably has CAF biological activity. Such a nucleic acid molecule can include a nucleic acid sequence encoding a CAF protein homologue, and can therefore be referred to as a homologue of a nucleic acid sequence encoding a naturally occurring CAF (i.e., a nucleic acid sequence homologue).

Therefore, one embodiment of the present invention includes a recombinant nucleic acid molecule, which includes at least one isolated nucleic acid molecule of the present invention inserted into any nucleic acid vector (e.g., a recombinant vector) which is suitable for cloning, sequencing, and/or otherwise manipulating the nucleic acid molecule, such as expressing and/or delivering the nucleic acid molecule into a host cell to form a recombinant cell. Such a vector contains heterologous nucleic acid sequences, that is, nucleic acid sequences that are not naturally found adjacent to nucleic acid molecules of the present invention, although the vector can also contain regulatory nucleic acid sequences (e.g., promoters, untranslated regions) which are naturally found adjacent to nucleic acid molecules of the present invention (discussed in detail below). The vector can be either RNA or DNA, either prokaryotic or eukaryotic, and typically is a virus or a plasmid. The vector can be maintained as an extrachromosomal element (e.g., a plasmid) or it can be integrated into the chromosome. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome of the host cell.

Typically, a recombinant molecule includes a nucleic acid molecule of the present invention operatively linked to one or more transcription control sequences. Such terms have been defined above. As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. Suitable transcription control sequences include any transcription control sequence that can function in at least one of the recombinant cells useful for expressing a CAF protein of the present invention. A variety of such transcription control sequences are known to those skilled in the art. Preferred transcription control sequences include those which function in bacterial, fungal (e.g., yeast), insect, plant or animal cells.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed CAF protein to be secreted from the cell that produces the protein. Suitable signal segments include a signal segment that is naturally associated with a CAF protein of the present invention or any heterologous signal segment capable of directing the secretion of a CAF protein according to the present invention. In another embodiment, a recombinant molecule of the present invention comprises a leader sequence to enable an expressed CAF protein to be delivered to and inserted into the membrane of a host cell. Suitable leader sequences include a leader sequence that is naturally associated with a CAF protein of the present invention, or any heterologous leader sequence capable of directing the delivery and insertion of a CAF protein to the membrane of a cell.

One type of recombinant molecule, referred to herein as a recombinant virus, includes a recombinant nucleic acid molecule of the present invention that is packaged in a viral coat and that can be expressed in a cell after delivery of the virus to the cell. A number of recombinant virus particles can be used, including, but not limited to, those based on alphaviruses, baculoviruses, poxviruses, adenoviruses, herpesviruses, and retroviruses.

One or more recombinant molecules of the present invention can be used to produce an encoded product (e.g., a CAF protein) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one nucleic acid molecule.

The present invention also includes isolated (i.e., removed from their natural milieu) antibodies capable of selectively binding to a CAF protein of the present invention (including CAF homologues) or a mimetic thereof (e.g., CAF antibodies). As used herein, the term "selectively binds to" refers to the ability of antibodies of the present invention to preferentially bind to specified proteins and mimetics thereof of the present invention. Binding can be measured using a variety of methods standard in the art including enzyme immunoassays (e.g., ELISA), immunoblot assays, etc.; see, for example, Sambrook et al., ibid. In one embodiment, a CAF antibody preferably selectively binds to a CAF protein in such a way as to reduce the activity of that protein, such as by blocking the ability of the protein to bind to a receptor (i.e., a CAF receptor), to another protein or to a nucleic acid molecule, or by otherwise disrupting its mechanism of action.

Isolated antibodies of the present invention can include serum containing such antibodies, or antibodies that have been purified to varying degrees. Antibodies of the present invention can be polyclonal or monoclonal, functional equivalents such as antibody fragments and genetically-engineered antibodies, including single chain antibodies or chimeric antibodies, including bi-specific antibodies that can bind to more than one epitope.

A preferred method to produce antibodies of the present invention includes (a) administering to an animal an effective amount of a protein, peptide or mimetic thereof of the present invention to produce the antibodies and (b) recovering the antibodies. In another method, antibodies of the present invention are produced recombinantly using techniques as heretofore disclosed to produce CAF proteins of the present invention. Antibodies raised against defined proteins or mimetics can be advantageous because such antibodies are not substantially contaminated with antibodies against other substances that might otherwise cause interference in a diagnostic assay, a screening assay, or side effects if used in a therapeutic composition.

Another embodiment of the present invention relates to a composition comprising a Cytokine Activating Factor of the present invention. Preferably, a composition also includes a pharmaceutically acceptable carrier, which has been defined above. According to the present invention, a "composition" includes any composition (formulation, product) comprising a Cytokine Activating Factor of the present invention, wherein CAF is present in the composition in a purified, recombinantly produced, chemically produced, substantially purified (i.e., any hyperimmune egg which has been purified to any degree to increase the amount CAF as compared to other components of the egg product), or any other CAF-enriched form, particularly as compared to hyperimmune egg products in the absence of any CAF selection or screening process (e.g., as described in U.S. Pat. No. 5,772,999). Therefore, hyperimmune egg products, in the absence of selection or screening for enriched amounts of CAF as compared to the average amount of CAF in hyperimmune egg products, or in the absence of any other means of enriching for CAF content in the egg product, are not encompassed by a composition of the present invention. As such, a composition which includes a hyperimmune egg product containing CAF according to the present invention must be selected, screened, or produced to be enriched, such as by: screening the immunization process to select hyperimmunized animals and/or hyperimmune egg products which contain statistically significantly higher amounts of CAF than the average hyperimmune egg product; by screening the hyperimmunized products for statistically significantly higher CAF content as compared to average amounts of CAF in hyperimmune egg products; or by enriching the hyperimmune egg product (e.g., by fractionation, purification, or supplementation with exogenous CAF) for CAF.

Therefore, in one embodiment, the composition of the invention is directed particularly to the production of compositions comprising hyperimmune egg and any products produced therefrom (i.e., food products or non-food products), which are enriched for the Cytokine Activating Factor of the present invention, which are useful in the modulation of the immune system. Being natural, these food products can be used to modulate the immune system without the fear of side effects, except, of course, for allergic reactions suffered by those intolerant to eggs. Preferably, the hyperimmune egg is obtained from an egg producing animal, and more preferably, an avian, which has been hyperimmunized with at least one immunogen. The hyperimmune egg product can be selected, screened or produced to have a statistically significantly higher CAF content (e.g., p>0.05) than an average content for hyperimmunized eggs from the same stock of egg-producing animal immunized by the same or different immunogens. The hyperimmune egg product is preferably further separated into CAF-enriched fractions, such as those described in Example 1.

By way of example, several batches of hyperimmune egg product can be screened to select those hyperimmune egg products with the highest level of Cytokine Activating Factor per dry weight of the egg product. Alternatively, the hyperimmunization process can be monitored (e.g., by sampling egg products during the immunization process) so that maximum production of the Cytokine Activating Factor is attained. Methods of detecting the Cytokine Activating Factor include, but are not limited to, purification and quantitation of the factor in the product, such as by any suitable protein purification and quantitation method (See the Examples section for an exemplary purification method). In one embodiment, the amount of Cytokine Activating Factor in a hyperimmune egg product is detected using an antibody of the present invention that selectively binds to the protein in the egg sample.

In addition, the egg product can be fractionated and/or purified to enrich for the presence of the Cytokine Activating Factor of the present invention relative to the other components in the egg product or to increase the amount (e.g., by weight) of CAF in the final product as compared to the amount of CAF in the initial egg product. Preferably, the amount of Cytokine Activating Factor in a fraction or purified product is enriched by at least about 5%, and more preferably by at least about 10%, and more preferably by at least about 25%, more preferably by at least about 50%, and more preferably by at least about 75%, and more preferably by at least about 100%, as compared to the amount of Cytokine Activating Factor present in unpurified hyperimmunized food product. Even more preferably, the amount of Cytokine Activating Factor in a fraction or purified product is enriched as compared to an amount of Cytokine Activating Factor in the initial product by at least about 2-fold, and more preferably by at least about 3-fold, and more preferably by at least about 5-fold, and more preferably by at least about 10-fold, and more preferably by at least about 50-fold, and more preferably by at least about 100-fold, and even more preferably by at least about 500-fold. In one embodiment, the Cytokine Activating Factor of the present invention is purified to substantially 100% purity, so that it can be added as a substantially pure factor to any of the compositions described herein. In another embodiment, the Cytokine Activating Factor of the present invention is produced recombinantly or synthetically, as discussed elsewhere herein.

The process for hyperimmunization of an egg-producing animal is described briefly as follows. The hyperimmune egg or egg product can be produced by any egg-producing animal. It is preferred that the egg-producing animal be a member of the class Aves or, in other words, an avian. Within the class Aves, domesticated fowl are preferred, but other members of this class, such as turkeys, ducks, and geese, are a suitable source of hyperimmune egg product.

When such egg-producing animals are brought to a specific state of immunization by means of, for example, periodic booster administrations of immunogens, the animals will produce eggs that, when consumed by a subject, will have beneficial properties, including supranormal levels of the Cytokine Activating Factor, which are effective in the modulation of the immune system in that subject.

The induction of immune sensitivity alone in the egg-producing animal is insufficient to cause the appearance of supranormal levels of the Cytokine Activating Factor in eggs, as is shown by the fact that table eggs do not contain such supranormal levels, even though the avians have been sensitized against various immunogens during normal immunization against avian diseases and during normal exposure to environmental factors. It is the inventors' finding that it is only in the specific hyperimmune states that the eggs have the desired supranormal levels of the Cytokine Activating Factor.

This special state of hyperimmunization, in which the egg will contain high levels of the Cytokine Activating Factor, is preferably achieved by administering an initial immunization, followed by periodic boosters with sufficiently high doses of specific immunogens or mixtures of immunogens. The preferred dosage of booster should be equal to or greater than 50% of the dosage necessary to produce primary immunization of the avian. Thus, there is a threshold booster dosage below which the properties are not produced in the avian's egg, even though the avian is in what normally would be called an immune state. Having knowledge of the requirement for developing and maintaining a hyperimmune state, it is within the skill of the art to vary the amount of immunogen administered, depending on the egg-producing animal genera and strain employed, in order to maintain the animal in the hyperimmune state. Furthermore, with the knowledge of CAF provided by the present invention, the immunization process can be additionally modified, such as by increasing the number or dosage of boosters, or by selecting specific immunogens, which result in increased production of CAF as compared to the average hyperimmune egg which is not exposed to such selection/screening processes.

The hyperimmune state is preferably produced by any immunogen or combination of immunogens. Hyperimmunization is preferably achieved by multiple exposures to multiple immunogens, multiple exposure to single immunogens, or single exposures to libraries of immunogens. Nearly any immunogen can be used to induce the hyperimmune state, including, but not limited to, bacterial, viral, protozoan, allergen, fungal or cellular substances.

In addition to immunizations with naturally occurring immunogens, immunization may also be accomplished using immunogens which are synthetically derived by combinatorial chemistries. The basic strategy is to assemble multiple combinations of chemical building blocks for producing a population of molecules with diversity. Several methods have recently been developed for solid and solution phase combinatorial synthesis of libraries of oligomers (Fodor, S. et al., Science 251:767 (1991); Houghton, R. et al., Nature 354:82 (1991)) as well as small organic molecules (Bunin, B. & Ellman, J., J. Am. Chem. Soc. 114:10997 (1992)). Rapid multiple peptide and oligomer synthesis can serve as a source for combinatorial derived immunogens. Furthermore, an alternative strategy would allow the addition of organic building blocks in combinatorial fashion to a backbone molecule for improved immunogenicity.

Alternative modes of hyperimmunizing egg producing animals can be used in place of immunogenic vaccines and include the use of genetic vaccines. In particular, any DNA construct (generally consisting of a promoter region and an antigen encoding sequence) will trigger an immune response. Genetic vaccines consist of antigen-coding vectors, fragments of naked DNA, plasmid DNA, DNA-RNA antigens, DNA-protein conjugates, DNA-liposome conjugates, DNA expression libraries, and viral and bacterial DNA delivered to produce an immune response. Methods of DNA delivery include particle bombardment, direct injection, viral vectors, liposomes and jet injection, among others. When applying these delivery methods, much smaller quantities may be necessary and generally result in more persistent immunogen production. When using such genetic processes, the preferred method for introducing DNA into avians is through intramuscular injection of the DNA into the breast muscle.

Methods of DNA delivery include, but are not limited to, particle bombardment, direct injection, liposomes, jet injection (Fynan, E. F. et al., Proc. Natl. Acad. Sci. USA 90:11478–11482 (1993)). The nucleic acids that code for known or unknown immunogens, promoter regions (notably CMV cauliflower mosaic virus) and SV40 bacterial origin can be replicated in bacteria to produce plasmid DNA for use in DNA injections. Although several routes of parenteral administration of the DNA are effective in chickens, the preferred method is intramuscular injection to the breast muscle. Vaccine trials are carried out in egg laying avians, preferably chickens. Repeated immunizations are given at one to two week intervals for up to six months.

It is preferred that the amounts of DNA used are generally in the order of 50–300 μg of DNA in saline for direct injection. For particle bombardment, 4–100 mg of DNA co-precipitated onto gold beads by the addition of 2.5 M $CaCl_2$ are preferred. Repeated immunizations can be given intradermally by this method of accelerating DNA coated particles into the live animal.

A detailed description of a preferred procedure used to bring an egg-producing animal to a heightened state of immunity from which the resultant hyperimmune egg or egg product can be administered to a subject is disclosed in U.S. Pat. No. 5,772,999, incorporated herein by reference in its entirety. Briefly, the following is an example of the procedure used to bring an egg-producing animal to a heightened state of immunity for use in purification of CAF or for production of a CAF-enriched food product for administration to a subject. It is to be understood that such a procedure can be modified as discussed above to select or screen for enhanced CAF production. In general, the hyperimmunization process includes the steps of:

1. Selecting one or more antigens.
2. Eliciting an immune response in the egg-producing animal by primary immunization.
3. Administering booster vaccines of antigens of appropriate dosage to induce and maintain the hyperimmune state.
4. Collecting and processing the eggs to produce a hyperimmune egg product from the egg-producing animal maintained in the hyperimmune state.

Step 1 Any antigen or combination of antigens may be employed. The antigens can be bacterial, viral, protozoan, fungal, cellular, or any other substances to which the immune system of an egg-producing animal will respond. The critical point in this step is that the antigen(s) must be capable of inducing immune and hyperimmune states in the egg-producing animal. One preferred vaccine is a mixture of polyvalent bacterial antigens, referred to as Series 100 (S-100) vaccine (also referred to as PL-100). The bacteria included in the S-100 vaccine (PL-100) are listed in U.S. Pat. No. 5,772,999 (Table 1). This vaccine has been previously described in U.S. Pat. Nos. 5,106,618 and 5,215,746, incorporated herein by reference in their entireties. Another preferred vaccine for use is the EB-100E vaccine, the details of which are also described in Example 1 of U.S. Pat. No. 5,772,999.

Step 2 The vaccine can be either a killed or live-attenuated vaccine and can be administered by any method that elicits an immune response. It is preferred that immunization be accomplished by administering the antigens through intramuscular injection. The preferred muscle for injection in an avian is the breast muscle. Dosage is preferably 0.5–5 milligrams of the antigen(s) vaccine. Other methods of administration that can be used include intravenous injection, intraperitoneal injection, rectal suppository, or oral administration. When DNA techniques are used for the hyperimmunization process, much smaller quantities are required, generally 1–100 micrograms. It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. In general, the appearance of egg antibodies after immunization with the vaccine is indicative of an immune response. The minimum dosage of antigen necessary to induce an immune response depends on the vaccination procedure used, including the type of antigen(s) used as well as the type of egg-producing animal used as the host.

Step 3 The hyperimmune state is preferably induced and maintained by repeated booster administrations of an appropriate dosage at fixed time intervals. The time intervals are preferably two-week intervals over a period of six months. However, it is essential that the booster administrations do not lead to immune tolerance. It is possible to use other hyperimmunization maintenance procedures or combination of procedures, such as, for example, intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means. Several combinations of primary and hyperimmunization are known to those skilled in the art.

Step 4 The hyperimmune eggs can be processed for administration to the subject or for purification in a variety of ways. These include preparation of a composition comprising the hyperimmune egg product substantially by itself (e.g., in capsules) and incorporation of the hyperimmune egg product into foods for administration to a subject, or following the purification protocol for Cytokine Activating Factor as described elsewhere herein.

In other embodiments, the composition of the present invention can include CAF in purified, recombinant, chemically synthesized, substantially purified, or any other enriched form, in combination with any suitable pharmaceutically acceptable carrier. Suitable pharmaceutically acceptable carriers according to the present invention include pharmaceutically acceptable excipients, controlled release vehicles, and pharmaceutically acceptable delivery vehicles as described above. The composition can be in any form suitable for delivery, including, but not limited to, a liquid, an aerosol, a capsule, a tablet, a pill, a powder, a gel and a granule. Preparations of the CAF that are particularly suitable for parenteral administration include sterile aqueous or nonaqueous solutions, suspensions or emulsions. Examples of nonaqueous solvents or vehicles are propylene glycol, polyethylene glycol, vegetable oils such as olive oil and injectable organic esters such as ethyl oleate.

In solid dosage forms, the CAF protein can be admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents, pH-sensitive polymers, or any other slow-releasing encapsulants (i.e., controlled release vehicles) which are typically used as encapsulating compositions in the food and drug industry or any other controlled release formulations. Tablets and pills can additionally be prepared with an enteric coating.

Liquid dosage forms of the Cytokine Activating Factor for oral administration include pharmaceutically acceptable emulsions, solutions, suspensions, syrups and elixirs, containing inert diluents commonly used in the pharmaceutical art. Besides inert diluents, compositions can also include wetting agents, emulsifying, and suspending, and sweetening agents.

In one embodiment, the composition is in the form of a food product. In this embodiment, in one aspect, the CAF-enriched egg, any CAF-enriched fraction thereof, the highly purified CAF, recombinant CAF, and/or chemically synthesized CAF is integrated into a nutritional supplement. One preferred method for preparing the egg, or any fraction thereof, to be incorporated into a nutritional supplement involves drying the egg into a powder. Although various methods are known for drying eggs, spray drying is a preferred method. The process of spray drying eggs is well known in the art. Such a dried egg powder can be incorporated into drinks in the form of, for example, protein powders, power building drinks, protein supplements and any other nutritional, athlete-associated products. In addition, the egg powder can be used in bake mixes, power bars, candies, cookies, etc. Other examples of egg processing include making an omelet, soft or hard-boiling the egg, baking the egg, or, if desired, the egg can be eaten raw or processed as liquid egg. Preferred fractions of a CAF-enriched egg product of the present invention include, but are not limited to: liquid egg yolk, liquid egg white, powdered egg yolk, powdered egg white, and/or a water soluble fraction of said hyperimmunized egg product.

In one embodiment of the present invention, a composition can include a recombinant nucleic acid molecule comprising a nucleic acid sequence encoding a CAF protein (including a homologue of CAF) as described previously herein, and/or an antibody that selectively binds to a CAF protein.

A composition of the present invention can be delivered (i.e., administered) to a cell culture (such as in a cytokine assay) or patient by any suitable method. Selection of such a method will vary with the type of compound being administered or delivered (i.e., protein, nucleic acid, mimetic), the mode of delivery (i.e., in vitro, in vivo, ex vivo) and the goal to be achieved by administration/delivery of the compound or composition. According to the present invention, an effective administration protocol (i.e., administering a composition in an effective manner) comprises suitable dose parameters and modes of administration that result in delivery of a composition to a desired site (i.e., to a desired cell) and/or in regulation of an immune response in a subject. Preferably, the composition of the present invention is administered to a subject animal by any means that modulates the immune system in the subject animal.

Administration routes include in vivo, in vitro and ex vivo routes. In vivo routes include, but are not limited to, oral, nasal, intratracheal injection, inhaled, transdermal, rectal, impregnation of a catheter, by suppository, direct injection into a tissue, and parenteral routes. Preferred parenteral routes can include, but are not limited to, subcutaneous, intradermal, intravenous, intramuscular and intraperitoneal routes. In one embodiment of the present invention, a composition containing a CAF protein, antibody, mimetic, or nucleic acid molecule of the present invention is administered by a parenteral route. Intravenous, intraperitoneal, intradermal, subcutaneous and intramuscular administrations can be performed using methods standard in the art. Aerosol (inhalation) delivery can also be performed using methods standard in the art (see, for example, Stribling et al., *Proc. Natl. Acad. Sci. USA* 189:11277–11281, 1992, which is incorporated herein by reference in its entirety). In another embodiment, a composition comprising a CAF protein of the present invention is administered orally. Oral delivery can be performed by complexing a therapeutic composition of the present invention to a carrier capable of withstanding degradation by digestive enzymes in the gut of an animal. It is noted that a CAF protein of the present invention is particularly resistant to digestive enzymes, and therefore, such a carrier may not be critical. Examples of such carriers, include plastic capsules or tablets, such as those known in the art. Such routes can include the use of pharmaceutically acceptable carriers as described above. Ex vivo refers to performing part of the regulatory step outside of the patient, such as by transfecting a population of cells removed from a patient with a recombinant molecule comprising a nucleic acid sequence encoding a protein according to the present invention under conditions such that the recombinant molecule is subsequently expressed by the transfected cell, and returning the transfected cells to the patient. In vitro and ex vivo routes of administration of a composition to a culture of host cells can be accomplished by a method including, but not limited to, transfection, transformation, electroporation, microinjection, lipofection, adsorption, protoplast fusion, use of protein carrying agents, use of ion carrying agents, use of detergents for cell permeabilization, and simply mixing (e.g., combining) a compound in culture with a target cell.

In one embodiment, hyperimmune eggs or fractions thereof which are enriched for the Cytokine Activating Factor of the present invention and collected from hyperimmunized animals are processed to produce a hyperimmune egg product which can subsequently be administered to a subject animal. In one embodiment, administration occurs by directly feeding the egg, or any derivative thereof to the subject animal. It is important to note that egg is a natural food ingredient which is non-toxic and safe. Similarly, in another embodiment, it is preferred that the substantially purified, recombinantly produced or synthetically produced Cytokine Activating Factor be prepared (e.g., formulated) in a manner which can subsequently be administered to an animal.

When it comes to modulation of the immune system, the composition of the present invention is preferably administered to the subject in an amount that is immunologically effective in achieving cytokine (i.e., TNF$\alpha$, IL-1$\beta$, and/or IL-6) expression and preferably, cytokine activation and immune modulation. Duration and intensity of the treatment will depend upon the particular subject and condition, of the subject and whether it is present, and, if so, the advancement of the condition in the subject. The composition is also provided in any amount that treats and/or prevents the condition and the symptoms of the condition.

For example, in the case of administration of CAF-enriched hyperimmune eggs or products produced therefrom, daily amounts ranging from less than one to several whole, hyperimmune eggs (or hyperimmune egg products containing the equivalent of less than one to several whole, hyperimmune eggs) can be administered to the subject depending on the particular circumstance of the condition. More potent fractions can be separated and concentrated by methods described herein as well as other known methods in the art. With regard to administration to a subject of the CAF-enriched hyperimmune egg or egg product, it has been determined that the preferred dose range of hyperimmune egg or egg product to be given to a subject is between 100 milligrams to 10 grams per kilogram of subject weight.

With regard to the isolated Cytokine Activating Factor of the present invention, including highly purified CAF, recombinant CAF and/or chemically synthesized CAF, it has been determined that the preferred dose range of the highly purified composition is between 1 nanogram and 400 milligrams per kilogram of the subject weight. In a preferred embodiment, the preferred dose range is between about 0.01 microgram and about 100 milligrams per kilogram of the subject weight. In another embodiment, a protein or antibody is administered in an amount that is between about 0.1 μg and about 10 mg per kg body weight of the patient, and more preferably, between about 0.1 μg and about 100 μg per kg body weight of the patient.

When the compound to be delivered is a nucleic acid molecule, an appropriate single dose results in at least about 1 pg of protein expressed per mg of total tissue protein per μg of nucleic acid delivered. More preferably, an appropriate single dose is a dose which results in at least about 10 pg of protein expressed per mg of total tissue protein per μg of nucleic acid delivered; and even more preferably, at least about 50 pg of protein expressed per mg of total tissue protein per μg of nucleic acid delivered; and most preferably, at least about 100 pg of protein expressed per mg of total tissue protein per μg of nucleic acid delivered. A preferred single dose of a naked nucleic acid vaccine ranges from about 1 nanogram (ng) to about 100 μg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 μm in diameter) and are propelled into skin cells or muscle with a "gene gun." It will be obvious to one of skill in the art that the number of doses administered to a patient is dependent upon the goal of the administration (e.g., the extent of the disease and the response of an individual patient to the treatment). Therefore, it is within the scope of the present invention that a suitable number of doses includes any number required to regulate an immune response in an animal, or to regulate a disease or condition which is expected to be treated or prevented by upregulation of proinflammatory cytokines (TNFα, IL-1β, IL-6) and/or by downregulation of TGFβ. Effective in vivo dose parameters can be determined using methods standard in the art. Such methods include, for example, determination of survival rates, side effects (i.e., toxicity), determination of cellular and humoral immune response effects, and/or effects on conditions related to such immune response effects.

It is one embodiment of the present invention to provide a method for modulating an immune response in an animal. This embodiment includes the steps of administering to an animal a composition as previously described herein, comprising a cytokine activating factor (CAF) protein of the present invention. In a preferred embodiment, the composition comprises a pharmaceutically acceptable carrier, also previously described herein. In this embodiment, the composition of the present invention can be used as a local or systemic stimulator of the immune system. It could also prevent and/or treat localized and systemic bacterial infection and could be employed as a general anticancer agent. It could also be tagged with specific delivery reagents like tissue specific antibodies, so as to deliver through the intravenous route to the specific site of bacterial infection or tumor formation. It could also be mixed with specific liposomes or delivery vehicles that are available commercially, so as to deliver it through the cytoplasmic and nuclear membrane of the cell and thereby facilitating the regulation of TNF-α, IL-1β, and/or IL-6 expression at the RNA level. Suitable modes of administration, including preferred routes and doses, are described above. Preferably, an animal is administered a composition of the present invention in a dose and by a route suitable to regulate an immune response by increasing the expression of TNF-α, IL-1β, and/or IL-6 and/or by decreasing the expression of TGF-β.

One embodiment of the present invention relates to a method of treating cancer in an animal, comprising administering to an animal that has or is at risk of developing cancer a composition comprising a cytokine activating factor (CAF) protein of the present invention. The methods of administration and details of the composition are as described in detail above. Preferably, administration of the composition produces a result selected from the group of: reduction in symptoms of the cancer, reduction of a tumor associated with the cancer, elimination of a tumor associated with the cancer, prevention of metastatic cancer, prevention of the cancer and stimulation of effector cell immunity against the cancer.

Yet another embodiment of the present invention relates to a method to treat or prevent sepsis and/or septic shock in an animal. Such a method includes the step of administering to an animal that has or is at risk of developing sepsis or septic shock a composition comprising a cytokine activating factor (CAF) protein of the present invention. The methods of administration and details of the composition are as described in detail above. Preferably, administration of the composition produces a result selected from the group of: reduction in symptoms of the sepsis or septic shock, prevention of the sepsis or septic shock and stimulation of effector cell immunity against the bacterial antigens associated with sepsis or septic shock.

The advantageous properties of this invention can be observed by reference to the following examples which illustrate the invention. These examples are provided for the purposes of illustration and are not intended to limit the scope of the present invention.

EXAMPLES

Example 1

The following example demonstrates the purification, isolation and sequencing of the Cytokine Activating Factor (CAF) of the present invention.

Purification of Cytokine Activating Factor

Overall Summary of CAF Purification

Figure 16:
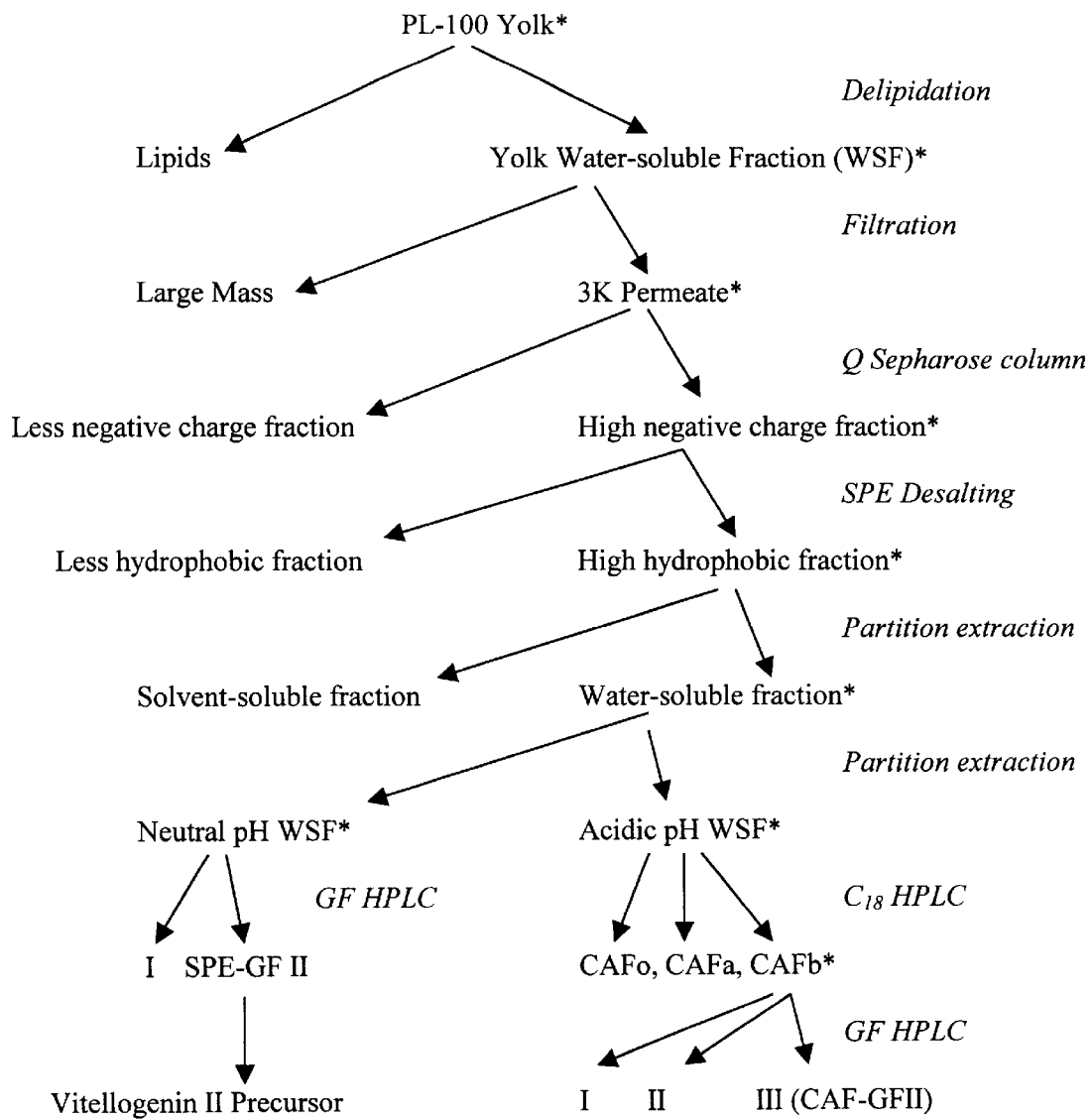
FIG. 16 is a schematic drawing illustrating the purification steps for CAF.

CAF was initially purified 600,000-fold from PL-100 whole egg by seven steps (FIG. 16), and it was shown to be a homogeneous component on HPLC chromatogram. The purification of the CAF throughout the process was tracked by assay of fractions for CAF in vitro biological activity via cytokine assays (described below). Whole egg was fractionated to egg yolk in the first step. After delipidation of the egg yolk, CAF was concentrated as a 3,000 Dalton (or less) permeate fraction using ultrafiltration technology. It is noted that the 3000 Dalton cut-off is approximate, since significantly larger proteins can pass through the filter if the secondary structure is permitting (i.e., substantially linear polypeptides/proteins). The permeate that passed through the 3,000 MW cut-off filter was applied to Q Sepharose chromatography for further separation. CAF appeared to be a strong negative charge molecule, which binds to the Q Sepharose column tightly and can be eluted by 0.3 M NaCl. In the next step, Solid Phase Extraction was used to remove the large amount of NaCl. This step also increased CAF purification by the removal of other more polar components. The CAF active fraction of SPE contains a water-insoluble component which was extracted by ethyl acetate and ethanol, leaving CAF in the water-soluble fraction. Finally, CAF was separated to a homogeneous component by reverse-phase $C_{18}$ HPLC and Gel Filtration HPLC. The overall yield of CAF purification was estimated to be about 20%. The amount of CAF in whole egg is calculated as 3–5 ppm (Table 1).

TABLE 1

CAF Purification Table

| Steps | Mechanism | Purification (fold) | Yield (g) |
| --- | --- | --- | --- |
| Whole egg | | 1 | 100,000 |
| Egg yolk | fractionation | 2 | 50,000 |
| 3K Filtration | size | 40 | 1,000 |
| Q Sepharose | charge | 30 | 30 |
| Solid Phase Extraction | desalting | 8 | 2 |
| Partition Extraction | fractionation | 2 | 0.8 |
| $C_{18}$ HPLC | polarity | 3 | 0.2 |
| Gel Filtration | size | 5 | 0.02 |
| Total | | ~600,000 | |

The individual steps of the purification process are more particularly described as follows.

Egg Yolk Delipidation

Spray-dried PL-100 egg yolk contains lipids, proteins, carbohydrates, ashes, and many biological factors, including CAF. To remove lipids and water-insoluble proteins, egg yolk was treated by caprylic acid phase-extraction followed by centrifugation. CAF and other water-soluble components were obtained in water phase.

Delipidation buffer for PL-100 egg yolk was prepared by dissolving 3.0 ml glacial acetic acid and 100 ml caprylic acid in 9 liters ultrapure water. The pH of the buffer is approximately 5.0. Egg yolk materials (1.0 kg spray-dried egg or 2.0 liters shell egg yolk) was added to the buffer and the mixture was further homogenized by blending at 24,000 rpm at room temperature for 5 min. Forms were removed and 20 ml of additional caprylic acid was added into the mixture to supplement the caprylic acid. The egg mixture was held at room temperature for over 2 hours to allow phase-separation. Flocculate was removed, and the aqueous phase of the egg mixture was centrifuged at room temperature for 20 minutes at 2,190×g. The supernatant of egg yolk was filtered through Whatman filter paper (113V, 40 μm). The pH of the supernatant was adjusted to 7.5 with 2.0 M NaOH.

Egg Yolk 3,000 Dalton MW Permeate Preparation

Figure 2:
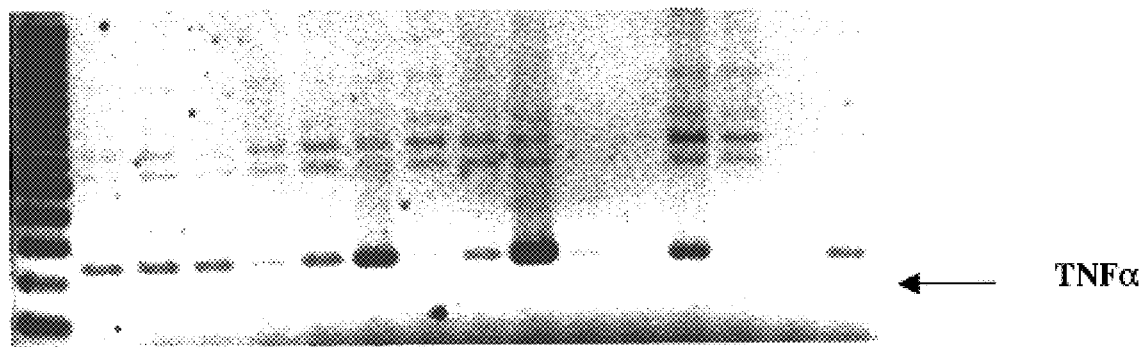
FIG. 2 is a digitized image showing the effect of 3,000 Dalton MW permeate on the induction of TNFα in an in vitro assay.
Figure 3:
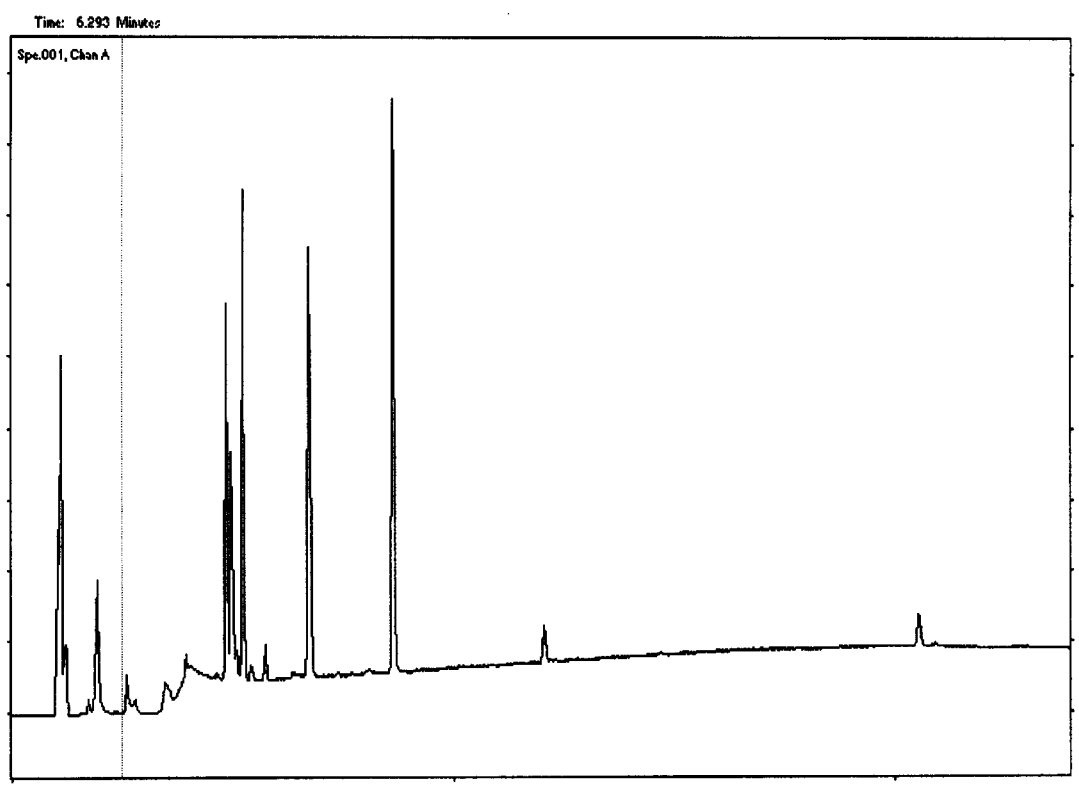
FIG. 3 is an HPLC chromatogram of PL-100 3,000 Dalton MW permeate.

Delipidated egg yolk supernatant contains water-soluble proteins and CAF. CAF can be separated from large molecular weight components by an ultra-filtration method. In this preparation, egg yolk supernatant fluid was pooled into a 22 L container which was attached to a filtration unit (3K MWCO, Amicon Model CH2 pump case and Spiral Cartridge Adapter kit). The pump pressure was maintained at approximately 30 psi in both the inlet and the outlet of filtration. Components having an apparent molecular weight of approximately less than 3,000 Daltons (based on their ability to pass through the 3000 Da cut-off filter) were collected as a permeate and lyophilized to dryness for storage, or frozen for further CAF purification. Approximately 2% of a whole egg yolk is obtained as a 3,000 Dalton permeate (also referred to herein as the "3K permeate"). CAF activities against TNFα and IL-1β in vitro assays were determined to track the presence of the CAF protein (FIGS. 1 and 2). The 3,000 Dalton MW permeate of egg yolk was also tested with Collagen II Induced Arthritis and Air pouch animal assays (data not shown). The 3K permeate was analyzed by Reverse-phase $C_{18}$ HPLC for purity determination (FIG. 3).

Q Sepharose Ion-Exchange Chromatography

Figure 4:
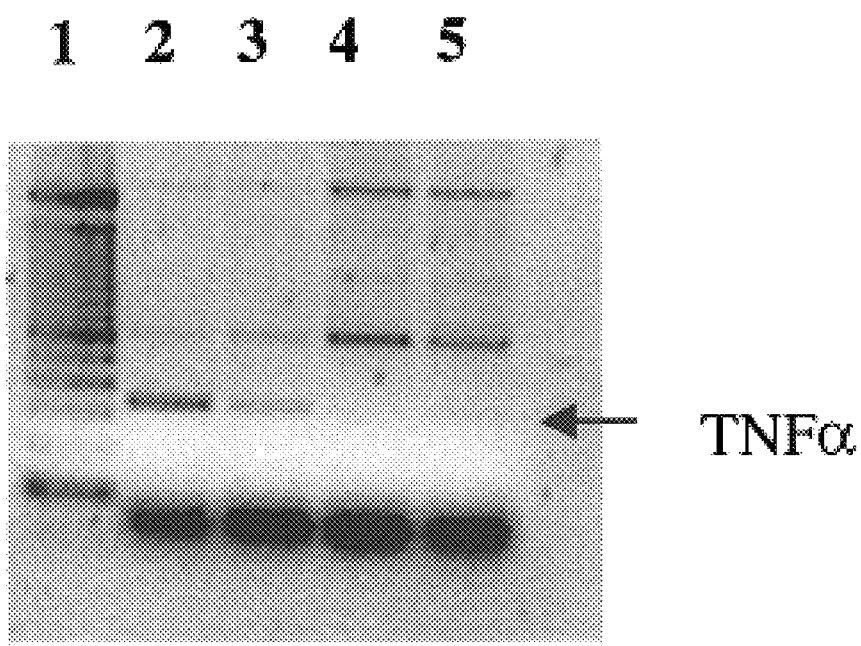
FIG. 4 is a digitized image showing the effect of Q Sepharose fractions of the 3000 Da MW permeate on TNFα induction in THP-1 cells.
Figure 5:
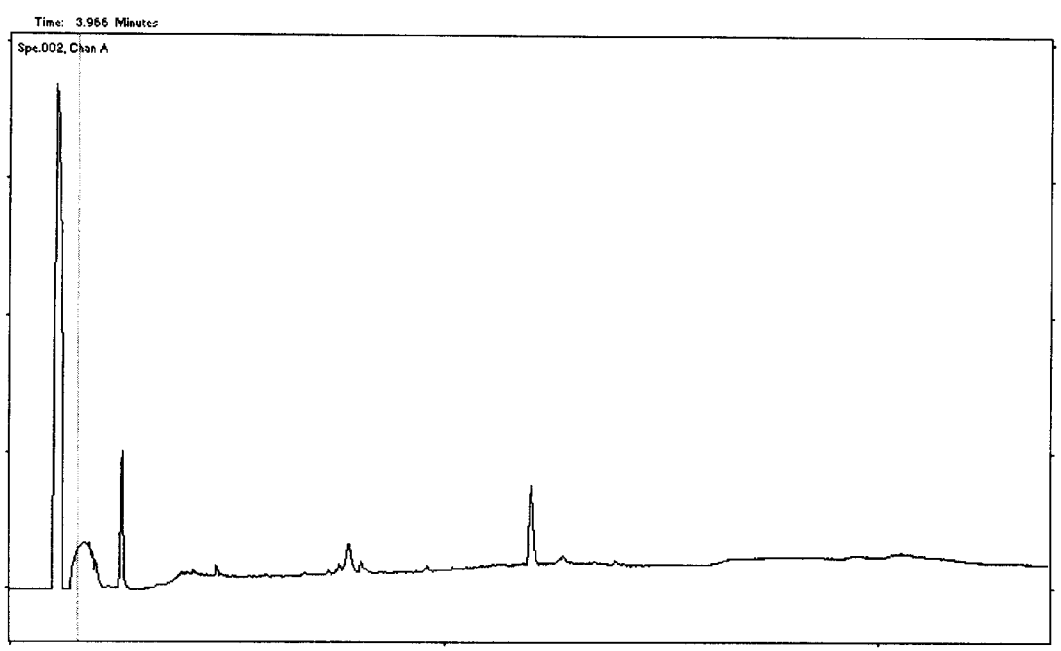
FIG. 5 is an HPLC chromatogram of the CAF active fraction on a Q Sepharose column.

The CAF in the 3000 Dalton permeate was further purified by anion exchange Q Sepharose chromatography. Most components of the 3,000 Dalton permeate were molecules with positive charges and they did not bind to Q Sepharose. However, CAF, in this example, bound on Q Sepharose and was found to be a molecule with a strong negative charge. The purification of CAF by Q Sepharose was a very efficient method. To set the Q Sepharose column, 2,000 ml Q Sepharose was diluted with 1,000 ml $dH_2O$ and loaded onto a glass column (8×40 cm). The ratio of I.D. to length was 1:5. The chromatography procedure was performed at room temperature. The column was equilibrated with 4,000 ml water and 8,000 ml of 20 mM ammonium acetate, pH 7.5, at a flow rate of 2,500 ml/h. 20–30 L of the 3,000 Dalton permeate was applied onto the Q Sepharose column with a flow rate of 1,500 ml/h. Q Sepharose was washed with the following buffers at a flow rate of 2,000 ml/h by stepwise elution: (1) 4,000 ml 20 mM ammonium acetate, pH 7.5, for washing column and eluting any unbound molecules; (2) 4,000 ml of 300 mM ammonium acetate, pH 6.5, for eluting some weakly bound molecules; (3) 4,000 ml 0.3 M NaCl for eluting CAF and other molecules; (4) 4,000 ml of 1.5 M NaCl for eluting the most tightly bound molecules and for regenerating the Q Sepharose column. A fraction of 0.3 M NaCl was collected in a flask after 1,200 ml elutant. For further CAF purification, the 0.3 M NaCl fraction was applied to Solid Phase Extraction. CAF activities against TNFα and IL-1β in vitro assay were determined (FIG. 4). The 3,000 Dalton MW permeate was also analyzed by reverse-phase $C_{18}$ HPLC (FIG. 5).

Solid Phase Extraction (SPE)

Figure 6:
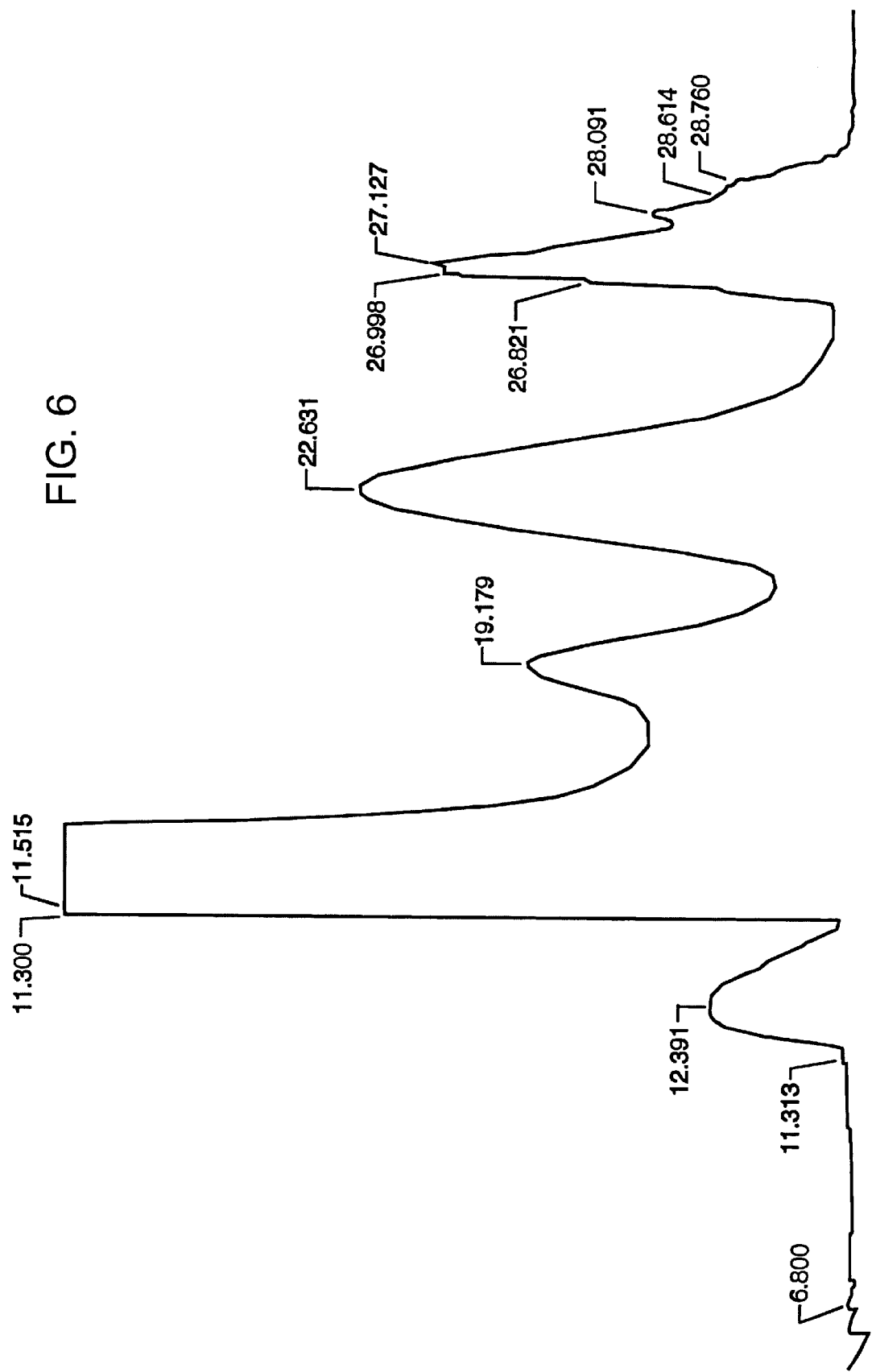
FIG. 6 is a Solid Phase Extraction chromatogram of CAF1 active fraction from Q Sepharose column.
Figure 7:
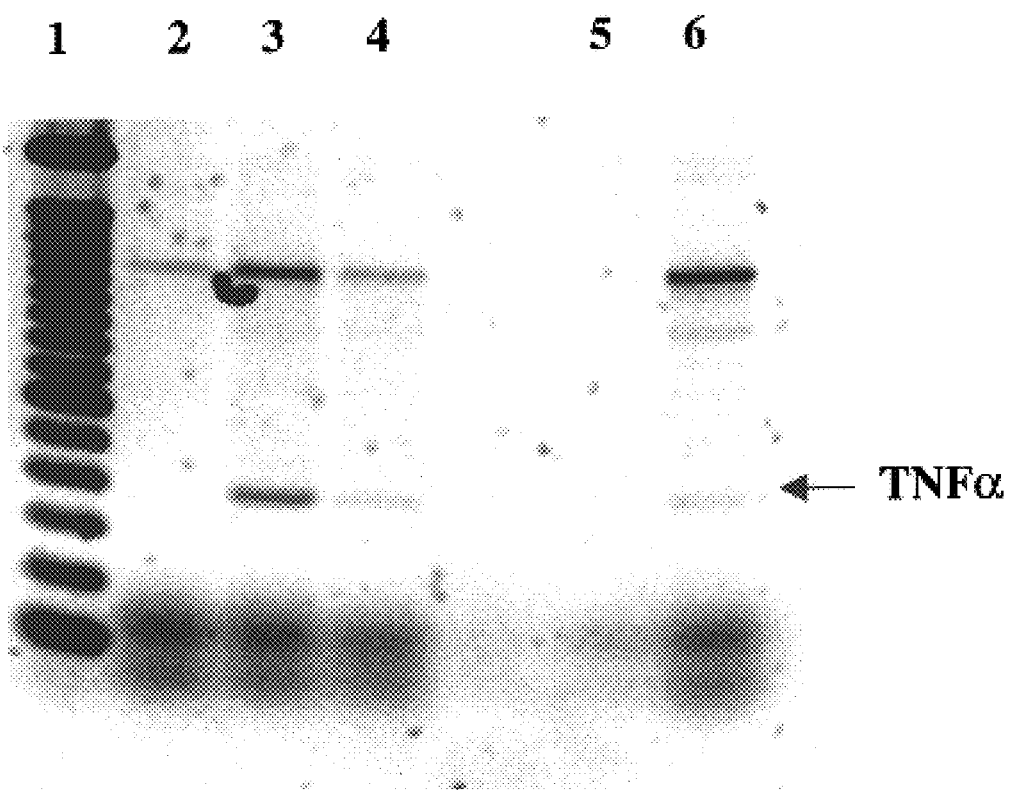
FIG. 7 is a digitized image showing the effect of Solid Phase Extraction fractions on TNFα induction in an in vitro assay.
Figure 8:
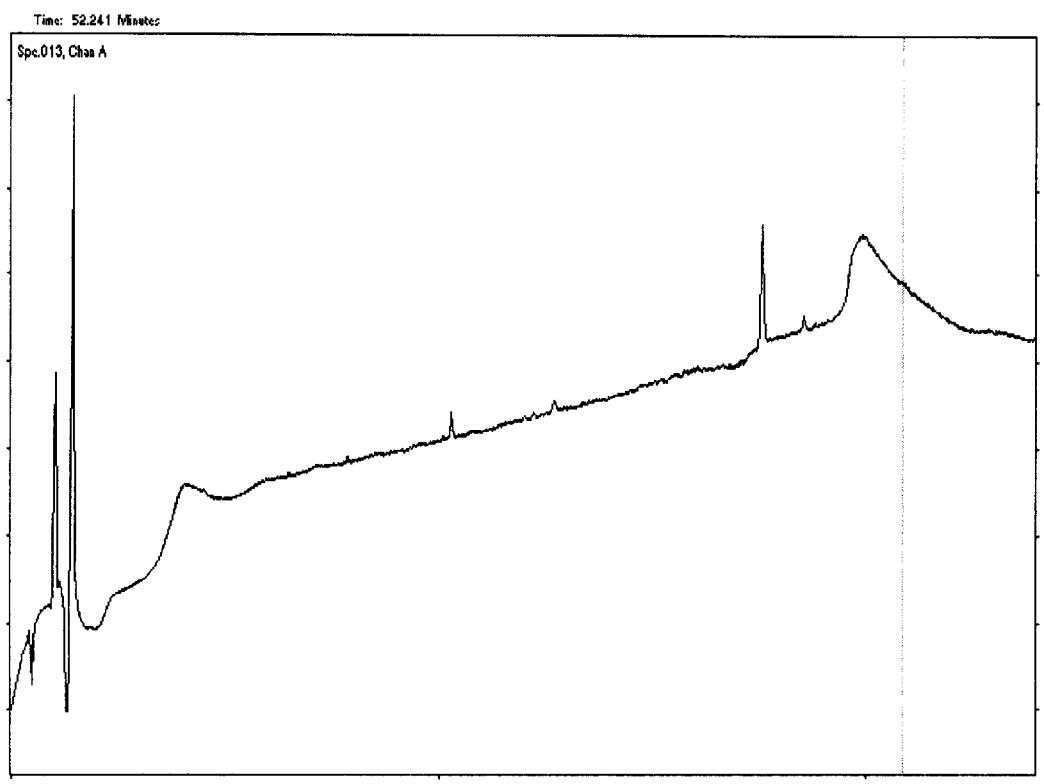
FIG. 8 is an HPLC chromatogram of the CAF active fraction of solid Phase Extraction.

The 0.3 M NaCl fraction from the Q Sepharose contains CAF and enormous quantities of salts. The Solid Phase Extraction (SPE) method is introduced to remove the salts and to increase CAF purity. Solid Phase Extraction is a convenient, inexpensive, and timesaving alternative to liquid/liquid extraction. This method is usually used for cleaning and concentrating compounds for analytical or isolation purposes. To increase the binding of CAF on SPE, the Q Sepharose fraction was adjusted to pH 2.0 with trifluoroacetic acid. The acidic fraction is applied to reverse phase $C_{18}$ resin in a column (5×22 cm) with an interaction condition. The Q Sepharose fraction was loaded onto the SPE column at room temperature with a flow rate of 40 ml/min. Chromatography was monitored at a wavelength of 254 nm. CAF and other components were retained on the pack material and most of the contaminants passed through the column. The column was washed with 800 ml of water, pH 2.0 and 1,200 ml 15% acetonitrile in water, pH 2.0. CAF and other components retained on the packing column were selectively washed out by 100% acetonitrile, pH 2.0 (FIG. 6). The CAF fraction (also referred to as the SPE fraction) was collected in a small volume. Highly purified CAF was lyophilized to dryness and it was ready for further purification. CAF activities against TNFα and IL-1β in vitro assay were determined (FIG. 7). The SPE fraction was also analyzed by reverse-phase $C_{18}$ HPLC (FIG. 8).

Partition Extraction of Solid Phase Extraction Fraction

First Partition Extraction step (FIG. 16): The solid phase extraction fraction of the Q Sepharose column was shown to contain a water-insoluble component (i.e., a solvent soluble fraction). This component was extracted by ethyl acetate and ethanol, leaving CAF in the water-soluble fraction (i.e., the SPE water soluble fraction). Briefly, 100 mg of the Solid Phase Extraction fraction was added to 10 ml of ethyl acetate and held at room temperature for 20 min. The mixture was transferred to a glass centrifuge tube and spun at 2,190×g for 20 min. A white pellet (SPE water-soluble fraction) was obtained after centrifugation. Ethyl acetate was removed and 10 ml of second ethyl acetate was added to repeat the step once again. Thereafter, 5.0 ml of ethanol was mixed with the pellet and centrifuged at 2,190×g for 20 min.

The SPE water-soluble fraction showed inhibition of inflammation in animal arthritis model. In an in vitro assay, the SPE water-soluble fraction (white pellet after spin) was shown to stimulate TNFα and IL-1β in THP1 cells. In contrast, the SPE water-insoluble fraction did not show such activities in an in vitro assay.

Figure 9:
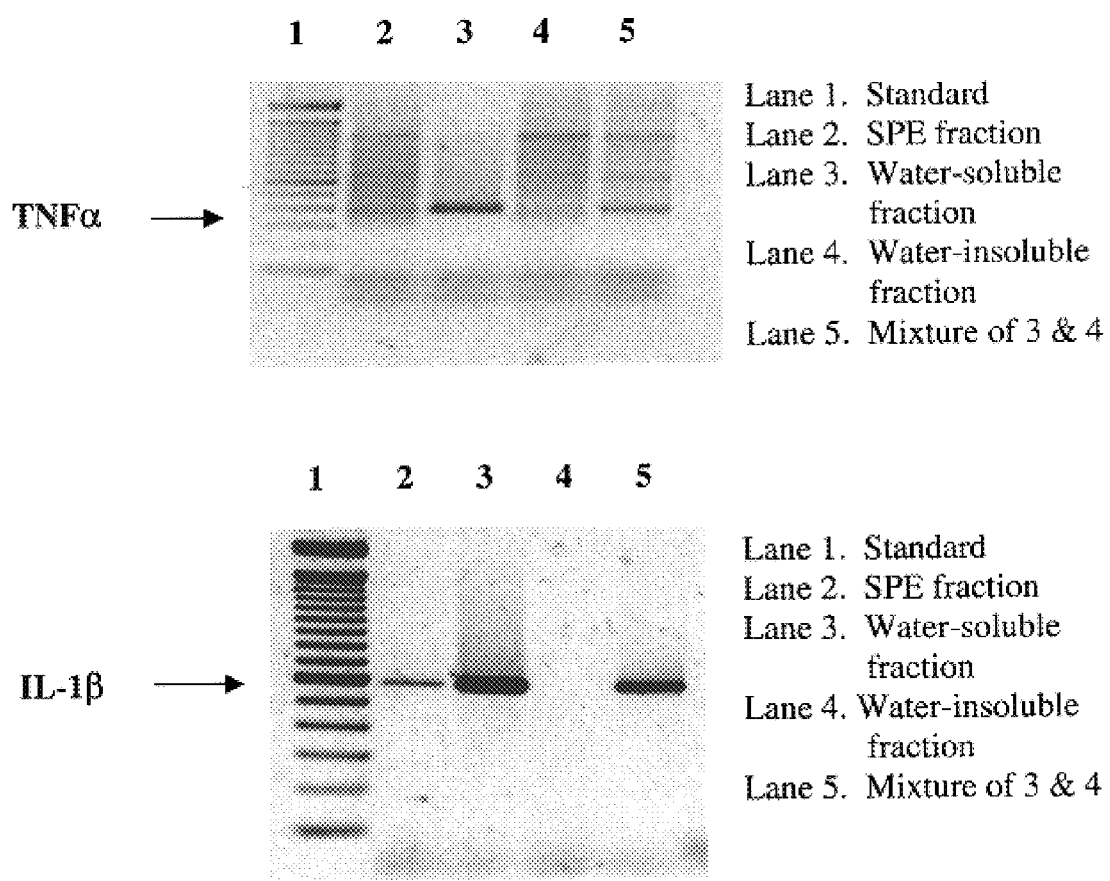
FIG. 9 is a digitized image showing the effect of Partition Extraction fractions on TNFα induction in an in vitro assay.
Figure 10:
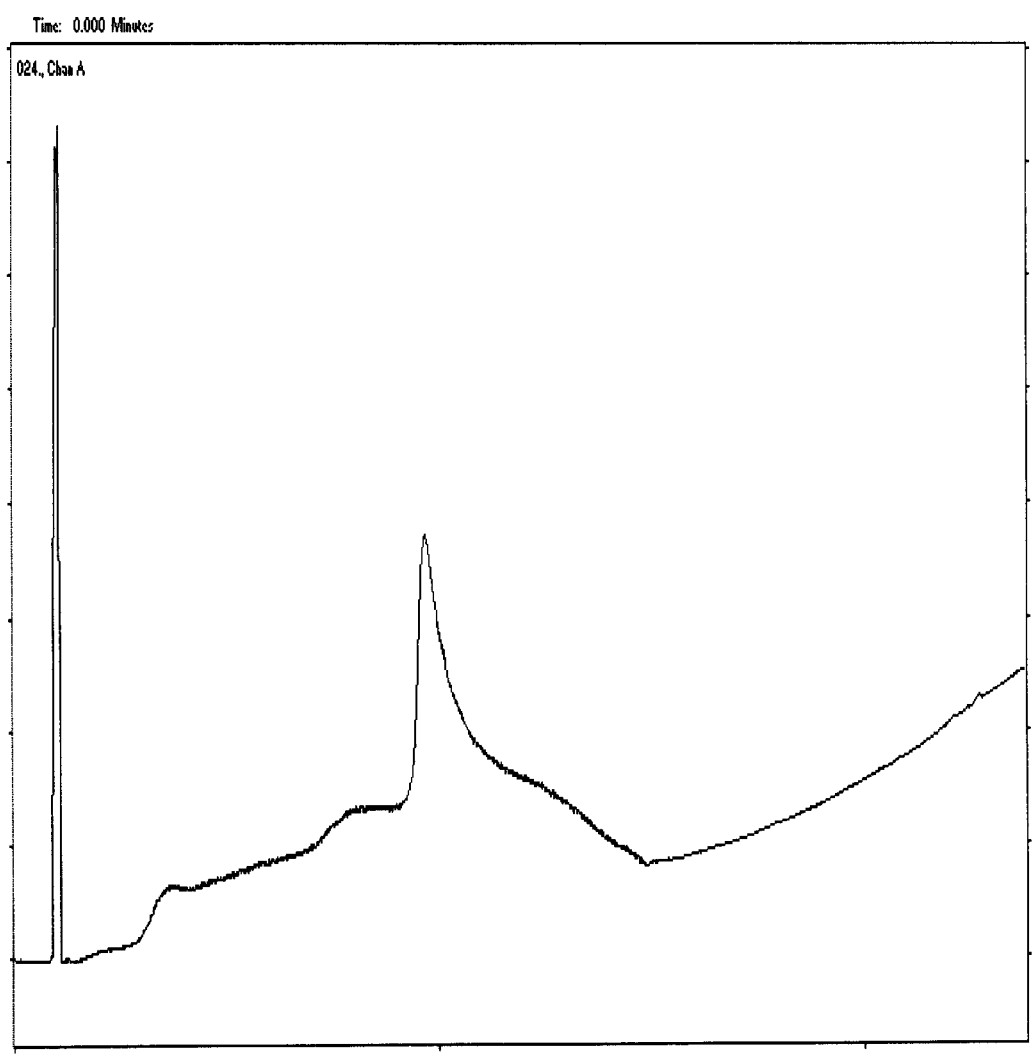
FIG. 10 is an HPLC chromatogram of water-soluble fraction by Partition Extraction.

Second Partition Extraction Step (FIG. 16): The SPE water-soluble fraction was further washed with 5.0 ml of 20 mM $NH_4OAc$ in water containing 20% acetonitrile, pH 7.0, and spun at 2,190×g for 20 min. At neutral pH, there is a water soluble fraction (FIG. 16, Neutral pH WSF) and a water insoluble fraction. The water insoluble fraction (at neutral pH) was lyophilized to dryness for CAF purification in preparative HPLC as described below. Although this neutral pH-water-insoluble fraction is practically insoluble in water at neutral pH, the present inventors found that it was soluble in water with low pH, and is therefore referred to as the Acidic pH water soluble fraction. CAF activities against TNFα and IL-1β in an in vitro assay (FIG. 9) were confirmed in the Acidic pH WSF and this CAF-active fraction (i.e., FIG. 16, Acidic pH WSF) was further analyzed by reverse phase $C_{18}$ HPLC (FIG. 10). Since the SPE water-soluble fraction (pellet after spin) is soluble in water with 0.1% TFA, pH 2.0 or in water with high pH 12.0, but has poor solubility in water with pH 7.0 (1.0 mg/ml), this suggested that the SPE water-soluble fraction possessed both an amine group and a carboxylic acid group, which are present commonly in peptides.

$C_{18}$ HPLC Separation

Figure 11:
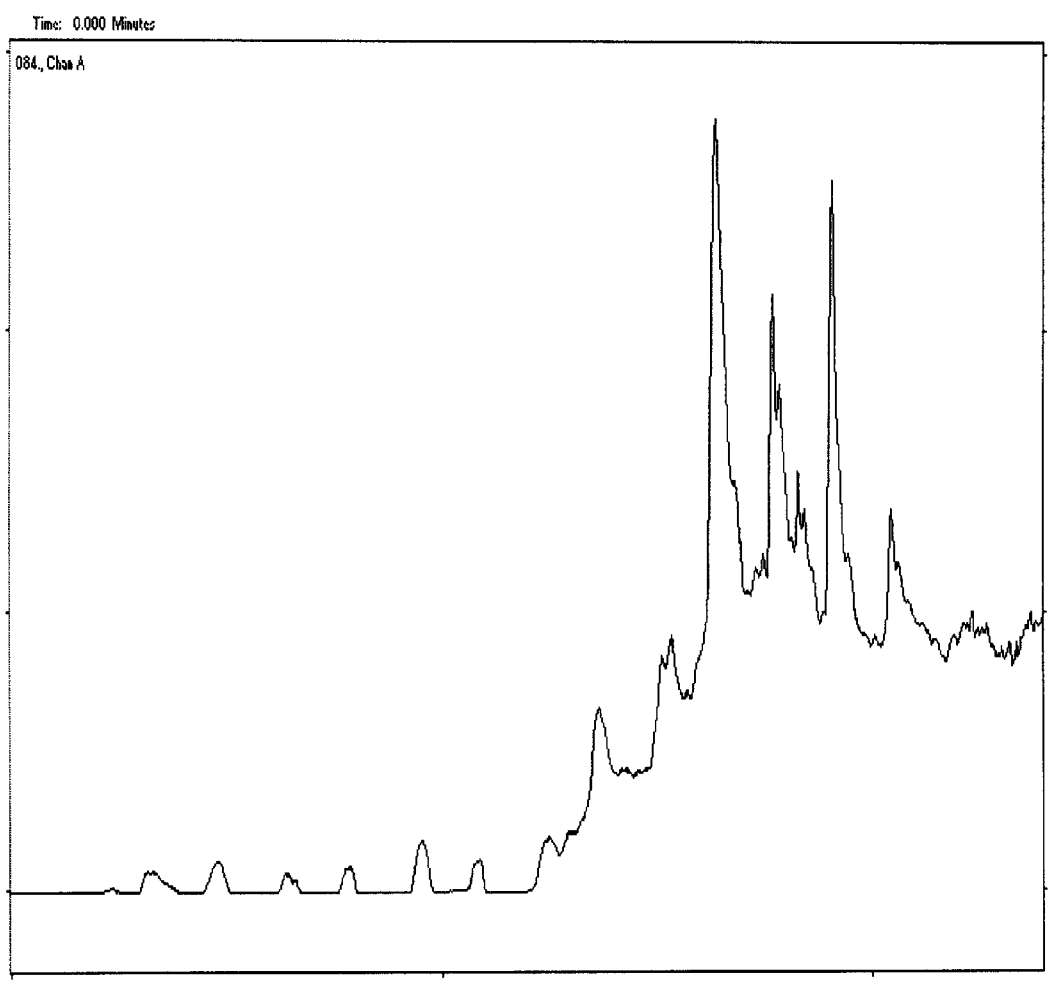
FIG. 11 is an HPLC chromatogram of $C_{18}$ HPLC separation of water-soluble fraction.
Figure 12:
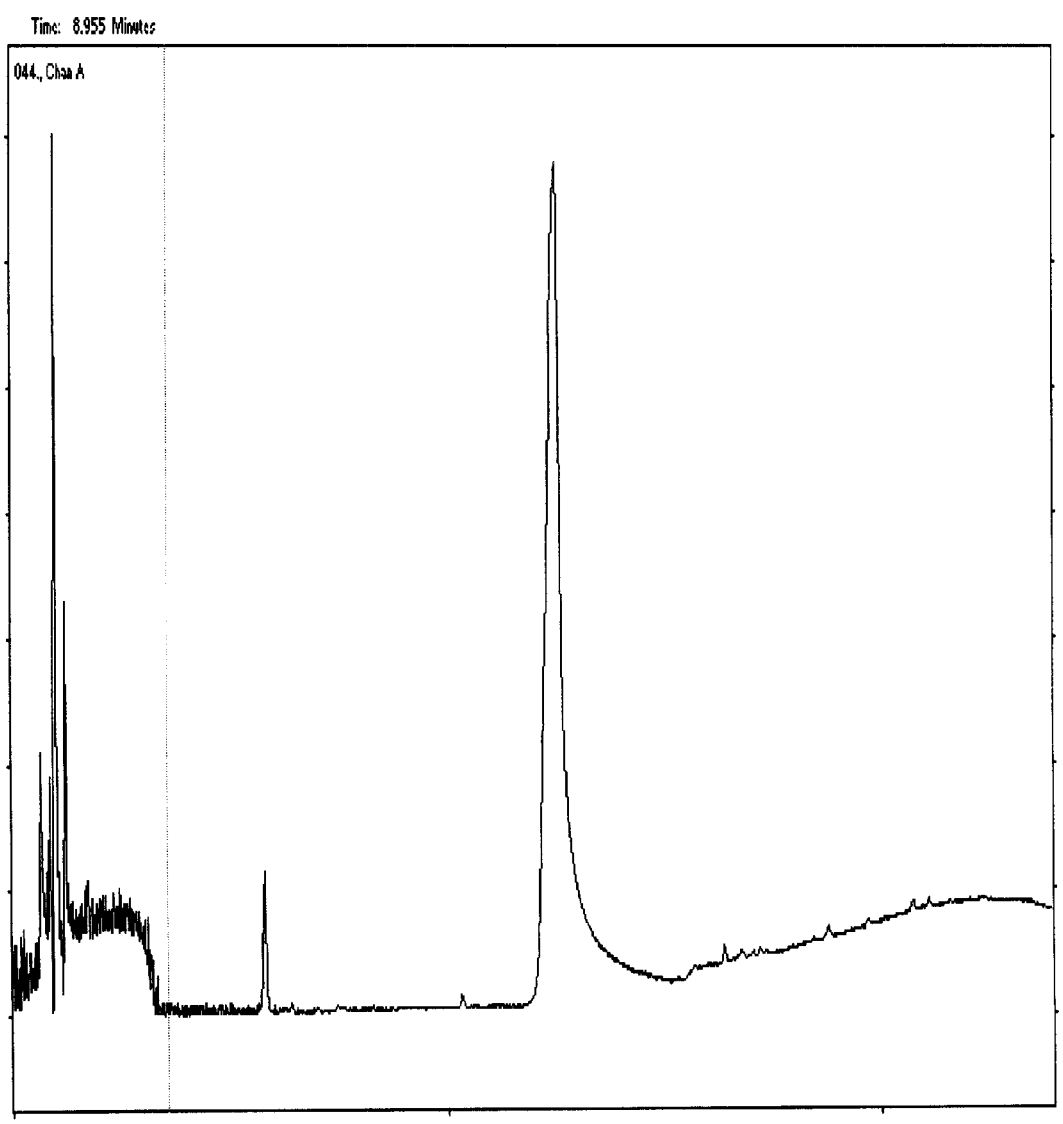
FIG. 12 is an HPLC chromatogram of purified CAF.
Figure 13:
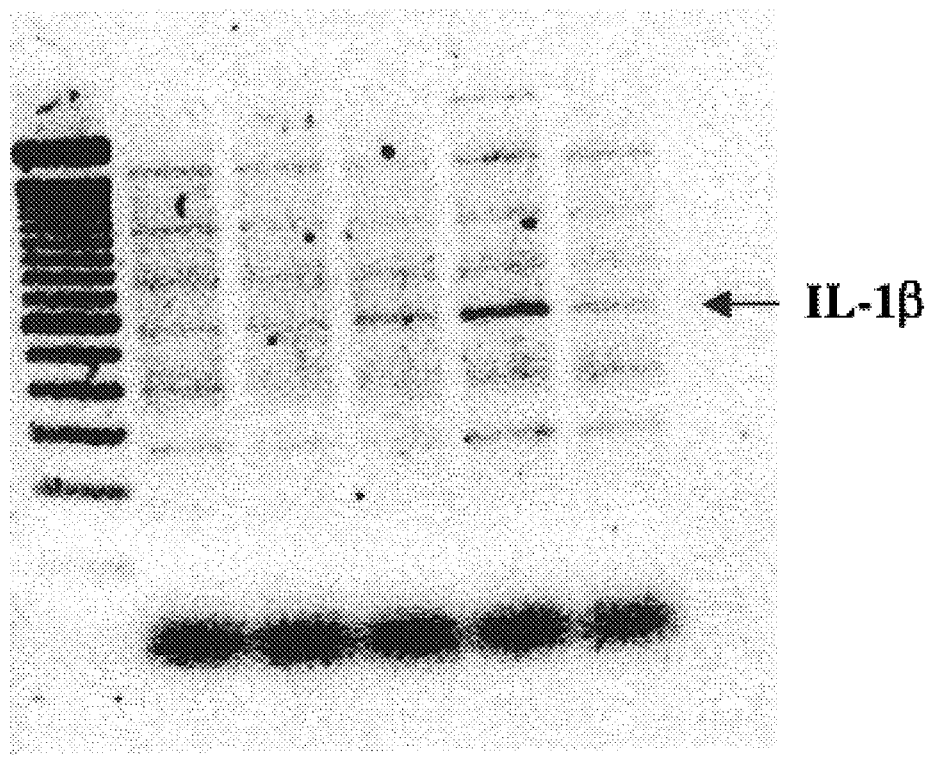
FIG. 13 is a digitized image showing the effect of CAF on IL-1β induction in an in vitro assay.

The Acidic pH water-soluble fraction of the Solid Phase Extraction appeared to contain a single component, which is shown on an HPLC chromatogram (FIG. 11). This single peak was identified as having CAF activity in a cytokine induction study as previously described. This CAF-enriched fraction was further separated into three components by reverse phase $C_{18}$ HPLC. In this separation, a Shimadzu HPLC Unit was employed. It is equipped with SPD-M10A VP Diode array detector, LC-6AD liquid chromatography, SCL-10A VP Degassor, LPM-600 Low-pressure mixing, and CTO-10A VP Column oven. The Acidic pH water-soluble fraction was prepared as 1.0 mg/ml in pure water with 0.1% TFA. 3.0 ml of the sample was applied onto a BTR IMPAQ $C_{18}$ column (10 μm, 22×250 mm) at 29° and with a flow rate of 12.0 ml/min. A linear gradient of 20%–100% methanol in $dH_2O$ that contained 0.1% trifluoroacetic acid (TFA) was used as the mobile phase. The three fractions referenced directly above were collected for CAF isolation. They were named: CAFo, CAFa, and CAFb. Acetonitrile in the fractions was removed by rotary evaporation and water was lyophilized out. It was determined that fraction CAFb (47 min–49.5 min) contained a single peak which was identified on the HPLC chromatogram (FIG. 12). This fraction also showed TNFα and IL-1β activities in an in vitro assay, indicating that the CAF had been purified to a homogeneous component as CAFb (FIG. 13).

Gel Filtration HPLC Separation

Further purification of various fractions from the SPE and $C_{18}$ HPLC steps above was performed by using Gel Filtration HPLC in the Shimadzu HPLC equipments as described above. Briefly, a sample was loaded on a gel filtration HPLC column (250×9.4 mm, Zorbox GF-250 Bio series) under a running condition (Buffer: 50 mM $NH_4OAc$, pH 8.0. Flow rate: 1.0 ml/min, 20° C., 20 min). The sample was dissolved in the running buffer at less than 1.0 mg/ml and injected in 30 μl for each run time.

SPE-water soluble fraction: The SPE water-soluble fraction was partially dissolved in 50 mM $NH_4OAc$ buffer, pH 8.0 at less than 1.0 mg/ml. Briefly, 1.0 mg of SPE water-soluble fraction was mixed with the buffer. After spinning at 10,000 rpm for 5 min, the supernatant was collected. The pellet was then mixed with the buffer again. The first supernatants were applied on GF250 HPLC column for determining molecule masses. There are three major fractions on GF250 column separation. They are 530,000 Da, 122,000 Da, and 1,240 Da. The three fractions were collected and lyophilized to dryness for cytokine assay. The MW of 530,000 Da and 122,000 Da were dissolved well in the first dissolving buffer, and they were not found in the second dissolving. The 1,240 Da peak, however, was better dissolved in the second dissolving, indicating that 530,000 Da and 122,000 Da molecules could be mostly removed by dissolving 1.0 mg of SPE water-soluble fraction in the buffer. The remaining non-dissolved pellet (i.e., SPE-GFII) is actually a quite pure compound with MW of 1,240 Da.

CAFb fraction: The CAFb fraction from the $C_{18}$ HPLC separation was also applied to a Gel Filtration HPLC column (GF 250) to test its molecular weight. It was found that there are three major fractions on the GF 250 column, 530,000 Da, 122,000 Da, and 40,000 Da, respectively. The 530,000 Da and 122,000 Da molecules can be reduced to a large molecule of 700,000 Da by 2-mercaptoethanol and boiling, indicating that aggregation could be occurring by changing the oxidation-reduction condition.

CAFo, CAFa, CAFb: To compare the molecular weights of the all of the cytokine-positive CAF fractions from the Acidic pH WSF on the GF250 HPLC column, CAFo, CAFa and CAFb were analyzed. CAFo has a single peak at 8.621 min (MW of 122,000 Da). CFAa has two peaks at 7.27 min (MW 530,000 Da) and 8.391 min (MW 122,000 Da). As discussed above, CAFb has an additional peak at 9.483 min (40,000 Da). The molecules of MW 530,000 Da and 122,000 Da can be reduced to a 700,000 Da molecule, which is similar to that seen in the SPE water-soluble fraction. The unique 40,000 Da fraction of CAFb, however, is stable under the reduction conditions (Table 2). Without being bound by theory, it is suggested that the MW 40,000 Da molecule of CAFb may still possess the active site of CAF, which could be aggregated from a smaller molecule of active CAF. The isolated CAFb fraction III (FIG. 16) (MW 40,000 Da) from GF-250 HPLC was named as CAFb-GFII).

TABLE 2

Comparison of CAF fractions from HPLC $C_{18}$ column

| | Cytokine assay | | HPLC CF250 peaks | | |
|---|---|---|---|---|---|
| CAF | TNFα | IL-1β | (min) | | |
| CAFo | − | − | | 8.621* | |
| CAFa | − | − | 7.270* | 8.391* | |
| CAFb | + | + | 7.040* | 8.621* | 9.483** |

*This peak can be reduced to a large molecule (~7.000 min).
**This compound is stable in reduction condition.

SPE-GF II: The supernatant of the SPE water-extraction was also analyzed on GF-250 HPLC. Two major peaks we found on HPLC chromatography (8.40 min and 12.22 min). The MW of the two peaks were about 120,000 Da and 2,000 Da, respectively. The 2,000 Da molecule was not found in CAFo, CAFa and CAFb, indicating it is a different compound. It was named as SPE-GFII.

Biological Activity of the Fractions

As described above, throughout the purification process, cytokine activity in vitro (measurement of induction of TNFα and/or IL-1β) was used to monitor the purification process and select the active fractions. In most experiments, the SPE water-soluble fraction was determined to have strong CAF cytokine-activating activity. Surprisingly, highly purified CAFb did not show as strong or better activity than the SPE water-soluble fraction. Without being bound by theory, it is suggested that CAFb has been changed in its form by the subsequent purification process, and its activity to cytokines decreases following the process of aggregation.

Characterization of CAF Fractions

Analytical $C_{18}$ HPLC

Fractions containing CAF were analyzed with reverse-phase High Performance Liquid Chromatography (HPLC) (Shimadzu Unit, SPD-M10A VP Diode array detection, LC-6AD liquid chromatography, SCL-10A VP Degassor, LPM-600 Low-pressure mixing, and CTO-10A VP Column oven). All of the fractions were prepared as 5.0 mg/ml in pure water and filtered through 0.2 μm filter unit. 20 μl of each sample was applied on a Water Symmetry $C_{18}$ column (3.9×150 mm) at 29° C. and with a flow rate of 1.0 ml/min. A linear gradient of 0%–60% acetonitrile in dH20 that contained 0.1 % trifluoroacetic acid (TFA) was used as the mobile phase.

FIG. 3 shows a Max plot chromatography of the separation of 3,000 Dalton MW permeate from delipidated PL-100 egg yolk. By using the same analytic conditions, subsequent fractions of the purification steps described above were also obtained (FIGS. 5, 8, 10, and 12).

CAF Structure Analysis

Protein Polyacrylamide Gel Electrophoresis (PAGE).

The molecular weight of CAFb was determined using SDS PAGE. The results showed that CAFb is a small peptide with a MW of about 6,670 Da. Due to the variability of SDS PAGE, however, the molecular weight of CAFb using SDS PAGE is not considered to be an accurate number, but rather an estimate of the molecular weight.

Mass Spectrometry (MS)

The SPE water-soluble fraction was dissolved in acidic water (Acidic pH WSF) and applied to reverse-phase $C_{18}$ preparative column for CAF separation. Three factions were collected. They are CAFo, CAFa, and CAFb. The active CAFb fraction stimulated TNFα and IL-1β activities in an in vitro assay. CAFb was studied on Mass Spectrometry for molecular weight determination. Results of ESI-MS showed that CAFb is a protein with MW of 15,500 Da. The large MW molecules of the CAFb fraction may result from aggregation of natural molecule during the purification process which could occur as a result of desalting.

Infrared Spectrometry (IR)

Figure 14:
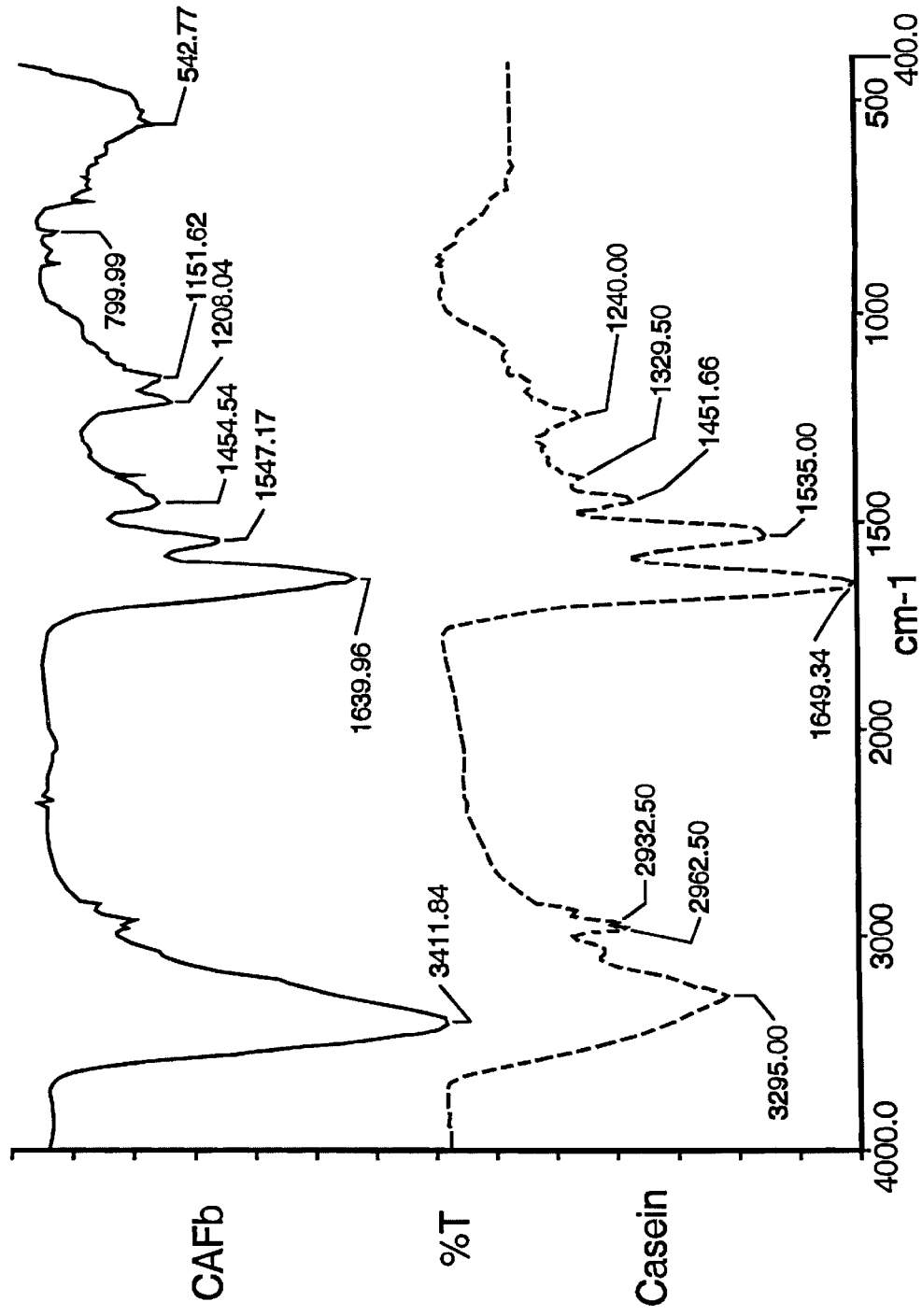
FIG. 14 is a chromatogram showing Infrared Spectrometry of CAF.

Infrared Spectrometry results showed that CAFb is a polypeptide with similar pattern as milk protein, casein (FIG. 14). IR results also demonstrated that CAFb is a pure compound.

N-terminal Amino Acid Sequence

N-terminal amino acid sequencing was performed using Enhanced Hewlett-Packard G1005A N-terminal Sequencers equipped HP G1314A variable wavelength detectors. The employed technology performs efficiently with samples ranging from sub-picomolar to nanomolar levels. The N-terminal amino acid sequences of CAFb-GFII and SPE-GFII were determined.

CAFb

Briefly, CAFb was dissolved with 50 μl of water plus 50 μl of 8 M GuHCl. Approximately 50 μl of sample was loaded onto a reverse-phase sample column using the Hewlett-Packard loading protocol. The sample cartridge was washed with 1 ml of 2% TFA. In the initial sequencing, the major N-terminal sequence was a very significant sequence of 30 amino acids, and is represented herein as SEQ ID NO:1. Two minor sequences were also determined in CAFb-GFII, and they were identical to the major sequence, except for the loss of one and two N-terminal residues (denoted SEQ ID NO:2 and SEQ ID NO:3, respectively). The initial sequence data is shown below:

CAFb-GFII 900 pmol $H_2N$—AGSSHEVVPSLLQTLLEGSIEQLYAGPISR (SEQ ID NO:1)

90pmol $H_2N$—s•hev•psl•qt••egsi•qly(a)gpI(s)r•n (SEQ ID NO:2)

90pmol $H_2N$—•••hev•psl••t••••s••q•••p (SEQ ID NO:3)

Subsequently, additional sequence was obtained, and a 70 amino acid polypeptide was determined, represented herein as SEQ ID NO:6, which is believed to represent the full-length CAFb protein:

CAFb-GFII 900 pmol $H_2N$—AGSSHEVVPSLLQTLLEGSIEQLYAG-PISRYNVDEMTSAALAELKKCIDELP-PXHLKALVNLXKQIRTEA (SEQ ID NO:6)

CAFb appears to be a polypeptide with 70 amino acids, and the molecule weight of CAFb is calculated as 8,839 Da, as shown in Table 3. Due to uncertainties at sequence positions 54 and 63, the major sequence (SEQ ID NO:6) is not assigned confidently at these positions. This polypeptide may be a dimer and form up to a 15,000 Da protein as found in the mass spectrophotometry (MS) study. The sequence data also suggested that the initial CAFb may be proteolyzed to small active peptide during immunization in cellular metablization process. The small CAFb present in yolk could be aggregated to large molecule during the process of purification.

It will be appreciated that one of ordinary skill in the art will be able to deduce nucleic acid sequences that encode SEQ ID NO:6, using the genetic code and accounting for the degeneracy therein. All nucleic acid sequences encoding SEQ ID NO:6 are contemplated and encompassed by the present invention. It will also be understood that, now that the amino acid sequence of the CAF protein is known, one of skill in the art will readily be capable of identifying, cloning and sequencing the nucleic acid molecule encoding the CAF protein using techniques that are well known in the art. For example, one of ordinary skill in the art can make degenerate primers based on the CAF amino acid sequence and amplify all or a portion of the nucleic acid sequence from an appropriate library or other suitable source by polymerase chain reaction. Additional cloning of the nucleic acid molecule can be performed by preparing a probe and screening a cDNA library, for example, for the full-length molecule, if necessary. Nucleic acid sequencing techniques are well known to those of skill in the art.

TABLE 3

Calculation of CAFb molecule weight

| Position | Letter | Amino acid | M.W.(Da) | R group |
|---|---|---|---|---|
| 1 | A | Alanine | 89 | NP |
| 2 | G | Glycine | 75 | P |

TABLE 3-continued

Calculation of CAFb molecule weight

| Position | Letter | Amino acid | M.W.(Da) | R group |
|---|---|---|---|---|
| 3 | S | Serine | 105 | P |
| 4 | S | Serine | 105 | P |
| 5 | H | Histidine | 155 | PC |
| 6 | E | Glutamic acid | 147 | NC |
| 7 | V | Valine | 117 | NP |
| 8 | V | Valine | 117 | NP |
| 9 | P | Proline | 115 | NP |
| 10 | S | Serine | 105 | P |
| 11 | L | Leucine | 131 | NP |
| 12 | L | Leucine | 131 | NP |
| 13 | Q | Glutamine | 146 | P |
| 14 | T | Threonine | 119 | P |
| 15 | L | Leucine | 131 | NP |
| 16 | L | Leucine | 131 | NP |
| 17 | E | Glutamic acid | 147 | NC |
| 18 | G | Glycine | 75 | P |
| 19 | S | Serine | 105 | P |
| 20 | I | Isoleucine | 131 | NP |
| 21 | E | Glutamic acid | 147 | NC |
| 22 | Q | Glutamine | 146 | P |
| 23 | L | Leucine | 131 | NP |
| 24 | Y | Tyrosine | 181 | P |
| 25 | A | Alanine | 89 | NP |
| 26 | G | Glycine | 75 | P |
| 27 | P | Proline | 115 | NP |
| 28 | I | Isoleucine | 131 | NP |
| 29 | S | Serine | 105 | P |
| 30 | R | Arginine | 174 | PC |
| 31 | Y | Tyrosine | 181 | P |
| 32 | N | Asparagine | 132 | P |
| 33 | V | Valine | 117 | NP |
| 34 | D | Aspartic acid | 133 | NC |
| 35 | E | Glutamic acid | 147 | NC |
| 36 | M | Methionine | 149 | NP |
| 37 | T | Threonine | 119 | P |
| 38 | S | Serine | 105 | P |
| 39 | A | Alanine | 89 | NP |
| 40 | A | Alanine | 89 | NP |
| 41 | L | Leucine | 131 | NP |
| 42 | A | Alanine | 89 | NP |
| 43 | E | Glutamic acid | 147 | NC |
| 44 | L | Leucine | 131 | NP |
| 45 | K | Lysine | 146 | PC |
| 46 | K | Lysine | 146 | PC |
| 47 | C | Cysteine | 121 | P |
| 48 | I | isoleucine | 131 | NP |
| 49 | D | Aspartic acid | 133 | NC |
| 50 | E | Glutamic acid | 147 | NC |
| 51 | L | Leucine | 131 | NP |
| 52 | P | Proline | 115 | NP |
| 53 | P | Proline | 115 | NP |
| 54 | X | Silent residue | 120 | |
| 55 | H | Histidine | 155 | PC |
| 56 | L | Leucine | 131 | NP |
| 57 | K | Lysine | 146 | PC |
| 58 | A | Alanine | 89 | NP |
| 59 | L | Leucine | 131 | NP |
| 60 | V | Valine | 117 | NP |
| 61 | N | Asparagine | 132 | P |
| 62 | L | Leucine | 131 | NP |
| 63 | X | Silent residue | 120 | |
| 64 | K | Lysine | 146 | PC |
| 65 | Q | Glutamine | 146 | P |
| 66 | I | Isoleucine | 131 | NP |
| 67 | R | Arginine | 174 | PC |
| 68 | T | Threonine | 119 | P |
| 69 | E | Glutamic acid | 147 | NC |
| 70 | A | Alanine | 89 | NP |
| | | | 8839 | |

P = Polar but uncharged
NP = Nonpolar
PC = Positive charged
NC = Negative charged
Calculated M.W of CAFb is close to 8,839 Da.

SPE-GFII

SPE-GFII was also sequenced from the N-terminus. It was clear from looking at the data from cycle 10 onward that there were two major sequences in this sample. One sequence, represented herein as SEQ ID NO:4, was identified as being a fragment of a known chicken vitellogenin II precursor. The x's indicated that some glycosylation occurred in the positions.

SPE-GFII H$_2$N-AViENLKARXxVSxNxIxTFNqVxFxYSMPA (SEQ ID NO:4)

The peptide sequence were compared with other known sequences in the BLAST database provided by NIH (Advanced BLAST, BLASTp, nr, Expect 10, Filtered).

Homology Search in Database

In the similarity search for the 70 amino acid CAFb-GFII (SEQ ID NO:6), 518,313 protein sequences and 162,653, 948 letters were compared. Results showed that this portion of CAFb-GFII is a unique sequence, and that there is no one identical sequence with any significant homology to it. The protein having the nearest identity to CAF is an amino acid sequence of a probable ligand-binding protein RYD5, which was isolated from Norway rat (Accession No. S17449). This 94 amino acid protein was 51% identical to SEQ ID NO:6 over amino acid residues 1–66 of SEQ ID NO:6. The longest consecutive stretch of amino acids shared by the two sequences was five. The function of the probable ligand-binding protein RYD5 appears to be a ligand binding protein in the subregions of the olfactory mucosa of the Norway rat. Therefore, it is believed that the CAF of the present invention and the RYD5 protein are not related by structure or by function.

SPE-GFII was also searched in the BLAST database. It was confirmed to be a modified fragment of chicken vitellogenin II precursor (SEQ ID NO:5) at position of 1572 to 1602 (FIG. 15). By the same phenomenon as hypothesized for CAF, the size of SPE-GFII may be varied due to the processes of degradation and aggregation. Vitellogenin II precursor is an important protein for regulating many proteins in the process of differentiation, including cytokines. The modified vitellogen II precursor fragment may also play a role in the function of anti-inflammation.

Example 2

The following example demonstrates the effect of Cytokine Activating Factor (CAF) on cytokine profiles and activation.

Cytokine assays were performed as follows.

Stimulation of Cells

Human THP-1 cells (Macrophage/Monocyte origin) cells are washed and plated at a density of 1×10$^6$ cells in 10 ml of serum free RPMI medium containing different egg fractions in a 25 ml flask. The cells are allowed to grow in a humidified CO$_2$ incubator for 4 hours, after which they are scraped and collected in a 50 ml centrifuge tube. The cells are pelleted by centrifugation at 400×g for 10 minutes and lysed in 750 μl of TRIzol reagent (Gibco BRL) and used for the extraction of total RNA as described below.

Extraction of RNA from Treated Cells

Extraction of total RNA from the PBL cell pellets was carried out according to the TRIzol reagent protocol (Gibco BRL). The total RNA extracted was quantified by ultraviolet spectrophotometry and the quality of the preparation was determined by analyzing the 28s and 18s bands on a 1.0% agarose gel in TBE buffer.

Synthesis of cDNA from the Total RNA

The first strand cDNA was synthesized from 5 μg of total RNA from each sample, using the cDNA Cycle® Kit for RT-PCR ( In Vitrogen, Carlsbad, Calif.). For comparative purposes, the ubiquitous GAPDH mRNA will be used to semi-quantitate each cDNA preparation.

Figure 17:
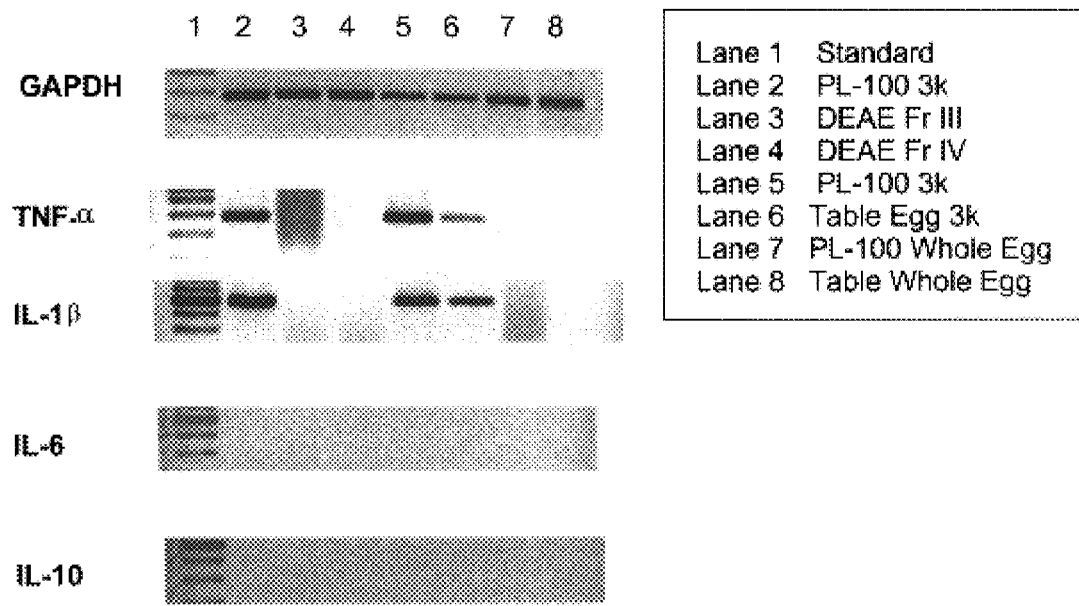
FIG. 17 is a digitized image showing cytokine RNA levels in THP-1 cells treated with different fractions of egg.

FIG. 17 depicts the cytokine profiles of THP-1 cells treated with partially purified fractions of various eggs. The tumor necrosis factor-α (TNF-α) expression levels were higher in cells treated with 3 k fraction (2 mg/ml) of PL-100 egg as compared to the 3k fraction of table eggs. Also, the interleukin-1β (IL-1β) levels were higher, but to a lesser extent in the PL-100 as compared to the table eggs. In this assay using the 3k fraction, there was no detectable induction of interleukin-6 (IL-6) or interleukin-10 (IL-10) in these cells. It is noted that in subsequent assays using highly purified CAFb, induction of IL-6 was clearly detected. The levels of TNF-α in the PL-100 whole egg (10 mg/ml) was slightly higher than that in the table egg but at concentrations much higher than that of the 3k fractions.

Kinetics of the TNF-α Activation by 3k Fraction of Hyperimmune Egg

Figure 18:
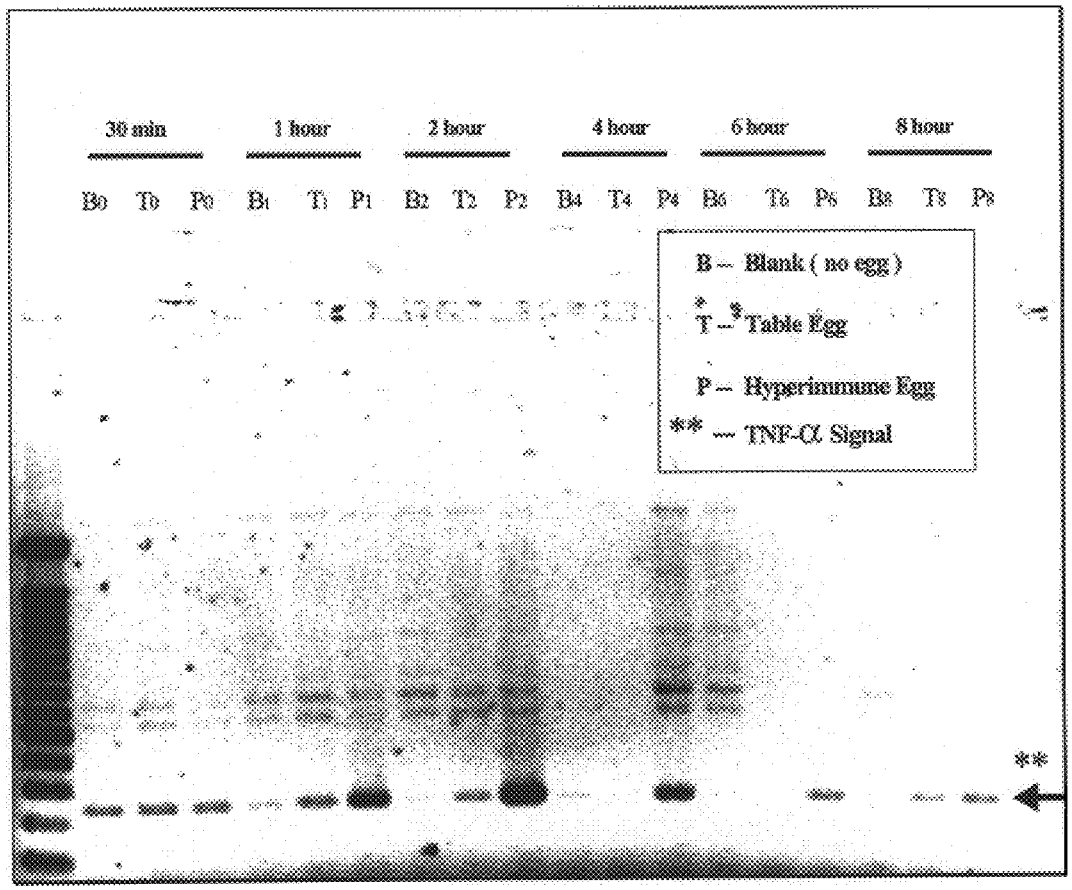
FIG. 18 is a digitized image showing the kinetics of TNFα activation by the 3000 Da permeate fraction of egg.

FIG. 18 depicts the kinetics of TNF-α activation in THP-1 cells by the 3k fraction of PL-100 egg yolk. The induction of TNF-α by PL-100 3k fraction began after 30 minutes and peaked at 2 hours after which it dropped off and attained baseline levels after 8 hours. The induction of TNF-α by Table egg 3k fraction was equal to or slightly higher than normal levels found in the cell.

Induction of Differentiation in THP-1 Cells by a Purified Fraction of the Hyperimmune Egg The THP-1 cells, which are transformed human cells of the monocytic/macrophage origin, undergo differentiation when treated with the 3k fraction derived from hyperimmune egg yolk. Normally, these cells grow in suspension as clusters and do not attach to plastic surfaces. However, when grown in a serum free media containing the 3k fraction (1 mg/ml) from hyperimmune egg (hereafter referred to as PL-100), they differentiated into fibroblast like cells and attached to the plastic surface. The 3k fraction, when further purified on an ion exchange column (Q-Sepharose) and eluted with 200 mM Sodium chloride, caused the THP-1 cells to differentiate at much lower concentration (0.01 mg/ml). There are several reports in literature which suggest that the production of TNF-α, IL-1α and IL-1β is associated with anti proliferation and differentiation of cells of the monocyte/macrophage origin.

Induction of Cytokine Expression by CAFb

Figure 19:
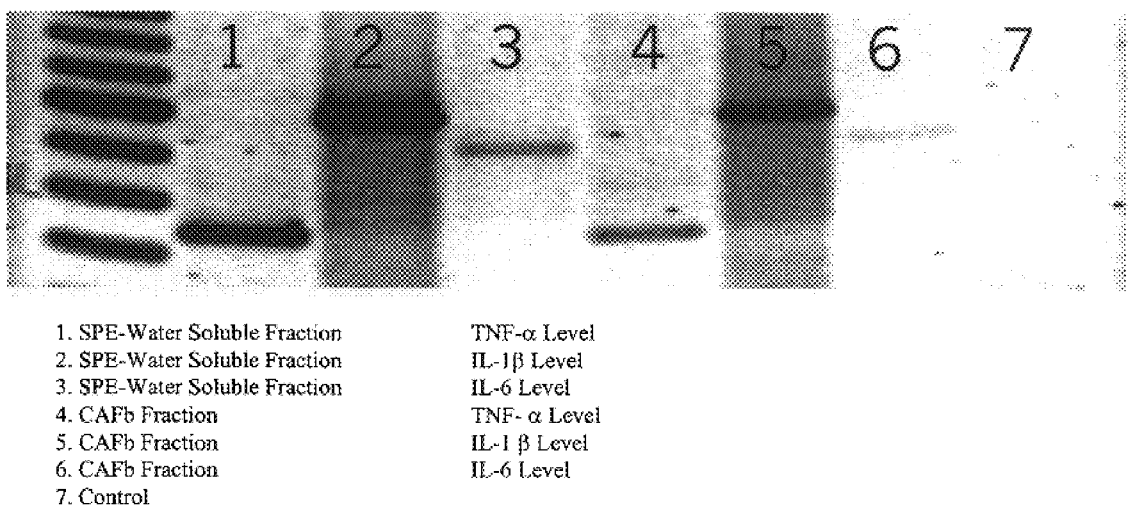
FIG. 19 is a digitized image showing the induction of three cytokines by CAFb.

Cytokine assays were performed as described above using the SPE water soluble fraction and the highly purified CAFb fraction as described in Example 1. FIG. 19 demonstrates that both the SPE water soluble fraction and the CAFb preparation induce the expression of TNFα, IL-1β and IL-6.

Inhibition of TGFβ by CAFb

Figure 20:
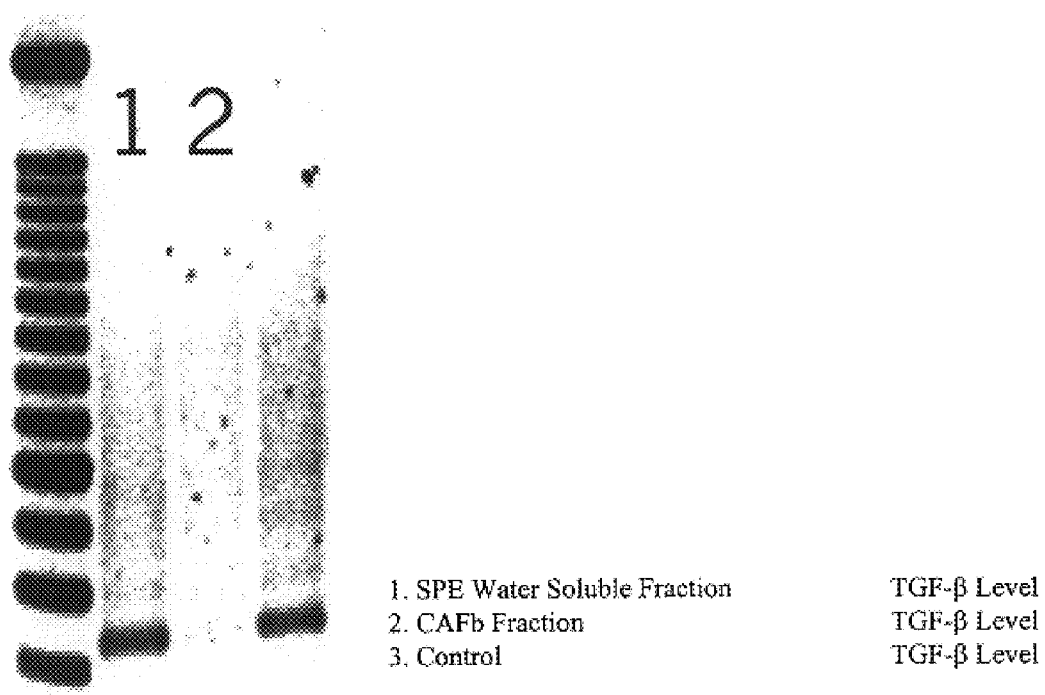
FIG. 20 is a digitized image showing the inhibition of transforming growth factor β by CAFb.

Cytokine assays were performed as described above using the SPE water soluble fraction and the highly purified CAFb fraction as described in Example 1. FIG. 20 demonstrates that CAFb, but not the SPE water soluble fraction, inhibits the induction of transforming growth factor β (TGFβ).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated protein, wherein said protein comprises the following identifying characteristics:

a. has a molecular weight of between about 6,670 Da and about 8,839 Da;
 b. is naturally present in both the egg white and egg yolk of avian eggs;
 c. upregulates expression of tumor necrosis factor α (TNFα), interleukin-1β (IL-1β) or interleukin-6 (IL-6), or downregulates expression of transforming growth factor β (TGFβ);
 d. contains more non-polar amino acid residues than polar amino acid residues; and,
 e. has a $\lambda_{max}$ at about 254 nm.

2. An isolated protein comprising an amino acid sequence selected from the group consisting of:
   a. an amino acid sequence selected from the group consisting of SEQ ID NO:1 and SEQ ID NO:6;
   b. A biologically active fragment of said amino acid sequence of (a); and,
   c. an amino acid sequence that is at least about 90% identical to said amino acid sequence of (a);
wherein said isolated protein upregulates expression of tumor necrosis factor α (TNFα), interleukin-1β (IL-1β) or interleukin-6 (IL-6), or downregulates expression of transforming growth factor β (TGFβ).

3. The isolated protein of claim 2, wherein said protein comprises an amino acid sequence that is at least about 95% identical to said amino acid sequence of (a).

4. The isolated protein of claim 2, wherein said protein comprises an amino acid sequence having at least about 15 consecutive amino acid residues of an amino acid sequence of (a).

5. The isolated protein of claim 2, wherein said protein comprises an amino acid sequence having at least about 20 consecutive amino acid residues of an amino acid sequence of (a).

6. The isolated protein of claim 2, wherein said protein comprises an amino acid sequence having at least about 25 consecutive amino acid residues of an amino acid sequence of (a).

7. The isolated protein of claim 2, wherein said protein comprises an amino acid sequence having at least about 50 consecutive amino acid residues of SEQ ID NO:6.

8. The isolated protein of claim 2, wherein said protein comprises amino acid sequence selected from the group consisting of SEQ ID NO:1 and SEQ ID NO:6.

9. The isolated protein of claim 2, wherein said protein comprises amino acid sequence SEQ ID NO:6.

10. The isolated protein of claim 2, wherein said protein has at least one biologically active subunit which passes through a 3000 Dalton molecular weight cut-off ultrafiltration filter.

11. The isolated protein of claim 2, wherein said protein is stable at a temperature up to at least about 50° C.

12. The isolated protein of claim 2, wherein said protein is stable at pH of from about 2 to about 10.

13. The isolated protein of claim 2, wherein said protein is biologically active before and after being administered orally.

14. The isolated protein of claim 2, wherein said protein is naturally present in both the egg white and egg yolk of hyperimmune avian eggs.

15. The isolated protein of claim 2, wherein said protein is naturally present in both the egg white and egg yolk of avian eggs.

16. A method to regulate an immune response in an animal, comprising administering to said animal a composition comprising the isolated protein of claim 2.

17. The method of claim 16, wherein said composition comprises a pharmaceutically acceptable carrier.

18. The method of claim 16, wherein said composition is administered at a dose of from about 1 nanogram to about 400 milligrams of said CAF protein per kilogram body weight of said animal.

19. The method of claim 16, wherein said composition is administered by a route selected from the group consisting of oral, intravenous administration, intraperitoneal administration, intramuscular administration, subcutaneous administration, transdermal delivery, intratracheal administration, inhalation, impregnation of a catheter, by suppository, and direct injection into a tissue.

20. The method of claim 16, wherein said composition comprises a food product containing said CAF protein.

21. The method of claim 16, wherein administration of said composition upregulates expression of tumor necrosis factor α (TNFα), interleukin-1β (IL-1β) or interleukin-6 (IL-6) by cells of said animal.

22. The method of claim 16, wherein administration of said composition downregulates expression of transforming growth factor β (TGFβ) by cells of said animal.

23. The method of claim 16, wherein animal is a mammal.

24. A composition comprising a pharmaceutically acceptable carrier and a cytokine activating factor (CAF) protein comprising an amino acid sequence selected from the group consisting of:
   a. an amino acid sequence selected from the group consisting of SEQ ID NO:1 and SEQ ID NO:6;
   b. a biologically active fragment of said amino acid sequence of (a); and,
   c. an amino acid sequence that is at least about 90% identical to said amino acid sequence of (a);
wherein said CAF protein upregulates expression of tumor necrosis factor α (TNFα), interleukin-1β (IL-1β) or interleukin-6 (IL-6), or downregulates expression of transforming growth factor β (TGFβ).

25. The composition of claim 24, wherein said protein comprises an amino acid sequence that is at least about 95% identical to said amino acid sequence of (a).

26. The composition of claim 24, wherein said protein comprises amino acid sequence selected from the group consisting of SEQ ID NO:1 and SEQ ID NO:6.

27. The composition of claim 24, wherein said protein comprises amino acid sequences SEQ ID NO:6.

28. The composition of claim 24, wherein said pharmaceutically acceptable carrier is a food product selected from the group consisting of:
   a. a hyperimmune egg product which is selected to be enriched for said CAF protein; and,
   b. a food product produced with at least a fraction of a hyperimmune egg product, wherein said fraction comprises an enriched amount of said CAF protein as compared to said hyperimmune egg product.

29. The composition of claim 24, wherein said pharmaceutically acceptable carrier comprises a fraction of a hyperimmune egg product containing an enriched amount of said CAF protein as compared to said hyperimmune egg product.

30. The composition of claim 29, wherein said fraction is selected from the group consisting of: liquid egg yolk, liquid egg white, powdered egg yolk, powdered egg white, and a water soluble fraction of said hyperimmune egg product.

31. The composition of claim 24, wherein said composition is in a form selected from the group consisting of a liquid, an aerosol, a capsule, a tablet, a pill, a powder, a gel and a granule.

32. The composition of claim 24, wherein said pharmaceutically acceptable carrier comprises a controlled release formulation.

33. The composition of claim 24, wherein said pharmaceutically acceptable carrier is selected from the group consisting of: water, phosphate buffered saline, Ringer's solution, dextrose solution, serum-containing solutions, Hank's solution, other aqueous physiologically balanced solutions, oils, esters, glycols, biocompatible polymers, polymeric matrices, capsules, microcapsules, microparticles, bolus preparations, osmotic pumps, diffusion devices, liposomes, lipospheres, cells, and cellular membranes.

* * * * *

SEQUENCE LISTING

<160> NUMBER OF SEQ ID NOS: 6

<210> SEQ ID NO 1
<211> LENGTH: 30
<212> TYPE: PRT
<213> ORGANISM: Gallus gallus

<400> SEQUENCE: 1

Ala Gly Ser Ser His Glu Val Val Pro Ser Leu Leu Gln Thr Leu Leu
 1               5                  10                  15

Glu Gly Ser Ile Glu Gln Leu Tyr Ala Gly Pro Ile Ser Arg
            20                  25                  30

<210> SEQ ID NO 2
<211> LENGTH: 30
<212> TYPE: PRT
<213> ORGANISM: Gallus gallus
<220> FEATURE:
<221> NAME/KEY: UNSURE
<222> LOCATION: (2)
<223> OTHER INFORMATION: Xaa = any residue
<221> NAME/KEY: UNSURE
<222> LOCATION: (6)
<223> OTHER INFORMATION: Xaa = any residue
<221> NAME/KEY: UNSURE
<222> LOCATION: (10)
<223> OTHER INFORMATION: Xaa = any residue
<221> NAME/KEY: UNSURE
<222> LOCATION: (13)..(14)
<223> OTHER INFORMATION: Xaa = any residue
<221> NAME/KEY: UNSURE
<222> LOCATION: (19)
<223> OTHER INFORMATION: Xaa = any residue

```
<221> NAME/KEY: UNSURE
<222> LOCATION: (29)
<223> OTHER INFORMATION: Xaa = any residue

<400> SEQUENCE: 2

Ser Xaa His Glu Val Xaa Pro Ser Leu Xaa Gln Thr Xaa Xaa Glu Gly
 1               5                  10                  15

Ser Ile Xaa Gln Leu Tyr Ala Gly Pro Ile Ser Arg Xaa Asn
            20                  25                  30

<210> SEQ ID NO 3
<211> LENGTH: 26
<212> TYPE: PRT
<213> ORGANISM: Gallus gallus
<220> FEATURE:
<221> NAME/KEY: UNSURE
<222> LOCATION: (1)..(3)
<223> OTHER INFORMATION: Xaa = any residue
<221> NAME/KEY: UNSURE
<222> LOCATION: (7)
<223> OTHER INFORMATION: Xaa = any residue
<221> NAME/KEY: UNSURE
<222> LOCATION: (11)..(12)
<223> OTHER INFORMATION: Xaa = any residue
<221> NAME/KEY: UNSURE
<222> LOCATION: (14)..(17)
<223> OTHER INFORMATION: Xaa = any residue
<221> NAME/KEY: UNSURE
<222> LOCATION: (19)..(20)
<223> OTHER INFORMATION: Xaa = any residue
<221> NAME/KEY: UNSURE
<222> LOCATION: (22)..(25)
<223> OTHER INFORMATION: Xaa = any residue

<400> SEQUENCE: 3

Xaa Xaa Xaa His Glu Val Xaa Pro Ser Leu Xaa Xaa Thr Xaa Xaa Xaa
 1               5                  10                  15

Xaa Ser Xaa Xaa Gln Xaa Xaa Xaa Xaa Pro
            20                  25

<210> SEQ ID NO 4
<211> LENGTH: 31
<212> TYPE: PRT
<213> ORGANISM: Gallus gallus
<220> FEATURE:
<221> NAME/KEY: UNSURE
<222> LOCATION: (10)..(11)
<223> OTHER INFORMATION: Xaa = any residue
<221> NAME/KEY: UNSURE
<222> LOCATION: (14)
<223> OTHER INFORMATION: Xaa = any residue
<221> NAME/KEY: UNSURE
<222> LOCATION: (16)
<223> OTHER INFORMATION: Xaa = any residue
<221> NAME/KEY: UNSURE
<222> LOCATION: (18)
<223> OTHER INFORMATION: Xaa = any residue
<221> NAME/KEY: UNSURE
<222> LOCATION: (24)
<223> OTHER INFORMATION: Xaa = any residue
<221> NAME/KEY: UNSURE
<222> LOCATION: (26)
<223> OTHER INFORMATION: Xaa = any residue

<400> SEQUENCE: 4

Ala Val Ile Glu Asn Leu Lys Ala Arg Xaa Xaa Val Ser Xaa Asn Xaa
 1               5                  10                  15

Ile Xaa Thr Phe Asn Gln Val Xaa Phe Xaa Tyr Ser Met Pro Ala
            20                  25                  30
```

```
<210> SEQ ID NO 5
<211> LENGTH: 1850
<212> TYPE: PRT
<213> ORGANISM: Gallus gallus

<400> SEQUENCE: 5

Met Arg Gly Ile Ile Leu Ala Leu Val Leu Thr Leu Val Gly Ser Gln
 1               5                  10                  15

Lys Phe Asp Ile Asp Pro Gly Phe Asn Ser Arg Ser Tyr Leu Tyr
             20                  25                  30

Asn Tyr Glu Gly Ser Met Leu Asn Gly Leu Gln Asp Arg Ser Leu Gly
         35                  40                  45

Lys Ala Gly Val Arg Leu Ser Ser Lys Leu Glu Ile Ser Gly Leu Pro
 50                  55                  60

Glu Asn Ala Tyr Leu Leu Lys Val Arg Ser Pro Gln Val Glu Glu Tyr
 65                  70                  75                  80

Asn Gly Val Trp Pro Arg Asp Pro Phe Thr Arg Ser Ser Lys Ile Thr
                 85                  90                  95

Gln Val Ile Ser Ser Cys Phe Thr Arg Leu Phe Lys Phe Glu Tyr Ser
             100                 105                 110

Ser Gly Arg Ile Gly Asn Ile Tyr Ala Pro Glu Asp Cys Pro Asp Leu
         115                 120                 125

Cys Val Asn Ile Val Arg Gly Ile Leu Asn Met Phe Gln Met Thr Ile
130                 135                 140

Lys Lys Ser Gln Asn Val Tyr Glu Leu Gln Glu Ala Gly Ile Gly Gly
145                 150                 155                 160

Ile Cys His Ala Arg Tyr Val Ile Gln Glu Asp Arg Lys Asn Ser Arg
                165                 170                 175

Ile Tyr Val Thr Arg Thr Val Asp Leu Asn Asn Cys Gln Glu Lys Val
            180                 185                 190

Gln Lys Ser Ile Gly Met Ala Tyr Ile Tyr Pro Cys Pro Val Asp Val
        195                 200                 205

Met Lys Glu Arg Leu Thr Lys Gly Thr Thr Ala Phe Ser Tyr Lys Leu
210                 215                 220

Lys Gln Ser Asp Ser Gly Thr Leu Ile Thr Asp Val Ser Ser Arg Gln
225                 230                 235                 240

Val Tyr Gln Ile Ser Pro Phe Asn Glu Pro Thr Gly Val Ala Val Met
                245                 250                 255

Glu Ala Arg Gln Gln Leu Thr Leu Val Glu Val Arg Ser Glu Arg Gly
            260                 265                 270

Ser Ala Pro Asp Val Pro Met Gln Asn Tyr Gly Ser Leu Arg Tyr Arg
        275                 280                 285

Phe Pro Ala Val Leu Pro Gln Met Pro Leu Gln Leu Ile Lys Thr Lys
290                 295                 300

Asn Pro Glu Gln Arg Ile Val Glu Thr Leu Gln His Ile Val Leu Asn
305                 310                 315                 320

Asn Gln Gln Asp Phe His Asp Asp Val Ser Tyr Arg Phe Leu Glu Val
                325                 330                 335

Val Gln Leu Cys Arg Ile Ala Asn Ala Asp Asn Leu Glu Ser Ile Trp
            340                 345                 350

Arg Gln Val Ser Asp Lys Pro Arg Tyr Arg Arg Trp Leu Leu Ser Ala
        355                 360                 365

Val Ser Ala Ser Gly Thr Thr Glu Thr Leu Lys Phe Leu Lys Asn Arg
370                 375                 380
```

```
Ile Arg Asn Asp Asp Leu Asn Tyr Ile Gln Thr Leu Thr Val Ser
385                 390                 395                 400

Leu Thr Leu His Leu Leu Gln Ala Asp Glu His Thr Leu Pro Ile Ala
            405                 410                 415

Ala Asp Leu Met Thr Ser Ser Arg Ile Gln Lys Asn Pro Val Leu Gln
                420                 425                 430

Gln Val Ala Cys Leu Gly Tyr Ser Ser Val Val Asn Arg Tyr Cys Ser
            435                 440                 445

Gln Thr Ser Ala Cys Pro Lys Glu Ala Leu Gln Pro Ile His Asp Leu
        450                 455                 460

Ala Asp Glu Ala Ile Ser Arg Gly Arg Glu Asp Lys Met Lys Leu Ala
465                 470                 475                 480

Leu Lys Cys Ile Gly Asn Met Gly Glu Pro Ala Ser Leu Lys Arg Ile
                485                 490                 495

Leu Lys Phe Leu Pro Ile Ser Ser Ser Ala Ala Asp Ile Pro Val
            500                 505                 510

His Ile Gln Ile Asp Ala Ile Thr Ala Leu Lys Lys Ile Ala Trp Lys
        515                 520                 525

Asp Pro Lys Thr Val Gln Gly Tyr Leu Ile Gln Ile Leu Ala Asp Gln
530                 535                 540

Ser Leu Pro Pro Glu Val Arg Met Met Ala Cys Ala Val Ile Phe Glu
545                 550                 555                 560

Thr Arg Pro Ala Leu Ala Leu Ile Thr Thr Ile Ala Asn Val Ala Met
                565                 570                 575

Lys Glu Ser Asn Met Gln Val Ala Ser Phe Val Tyr Ser His Met Lys
                580                 585                 590

Ser Leu Ser Lys Ser Arg Leu Pro Phe Met Tyr Asn Ile Ser Ser Ala
            595                 600                 605

Cys Asn Ile Ala Leu Lys Leu Leu Ser Pro Lys Leu Asp Ser Met Ser
610                 615                 620

Tyr Arg Tyr Ser Lys Val Ile Arg Ala Asp Thr Tyr Phe Asp Asn Tyr
625                 630                 635                 640

Arg Val Gly Ala Thr Gly Glu Ile Phe Val Val Asn Ser Pro Arg Thr
                645                 650                 655

Met Phe Pro Ser Ala Ile Ile Ser Lys Leu Met Ala Asn Ser Ala Gly
                660                 665                 670

Ser Val Ala Asp Leu Val Glu Val Gly Ile Arg Val Glu Gly Leu Ala
            675                 680                 685

Asp Val Ile Met Lys Arg Asn Ile Pro Phe Ala Glu Tyr Pro Thr Tyr
        690                 695                 700

Lys Gln Ile Lys Glu Leu Gly Lys Ala Leu Gln Gly Trp Lys Glu Leu
705                 710                 715                 720

Pro Thr Glu Thr Pro Leu Val Ser Ala Tyr Leu Lys Ile Leu Gly Gln
                725                 730                 735

Glu Val Ala Phe Ile Asn Ile Asn Lys Glu Leu Leu Gln Gln Val Met
                740                 745                 750

Lys Thr Val Val Glu Pro Ala Asp Arg Asn Ala Ala Ile Lys Arg Ile
            755                 760                 765

Ala Asn Gln Ile Arg Asn Ser Ile Ala Gly Gln Trp Thr Gln Pro Val
        770                 775                 780

Trp Met Gly Glu Leu Arg Tyr Val Val Pro Ser Cys Leu Gly Leu Pro
785                 790                 795                 800

Leu Glu Tyr Gly Ser Tyr Thr Thr Ala Leu Ala Arg Ala Ala Val Ser
```

-continued

```
                    805                 810                 815
Val Glu Gly Lys Met Thr Pro Pro Leu Thr Gly Asp Phe Arg Leu Ser
                820                 825                 830
Gln Leu Leu Glu Ser Thr Met Gln Ile Arg Ser Asp Leu Lys Pro Ser
                835                 840                 845
Leu Tyr Val His Thr Val Ala Thr Met Gly Val Asn Thr Glu Tyr Phe
850                 855                 860
Gln His Ala Val Glu Ile Gln Gly Glu Val Gln Thr Arg Met Pro Met
865                 870                 875                 880
Lys Phe Asp Ala Lys Ile Asp Val Lys Leu Lys Asn Leu Lys Ile Glu
                885                 890                 895
Thr Asn Pro Cys Arg Glu Glu Thr Glu Ile Val Val Gly Arg His Lys
                900                 905                 910
Ala Phe Ala Val Ser Arg Asn Ile Gly Glu Leu Gly Val Glu Lys Arg
                915                 920                 925
Thr Ser Ile Leu Pro Glu Asp Ala Pro Leu Asp Val Thr Glu Glu Pro
            930                 935                 940
Phe Gln Thr Ser Glu Arg Ala Ser Arg Glu His Phe Ala Met Gln Gly
945                 950                 955                 960
Pro Asp Ser Met Pro Arg Lys Gln Ser His Ser Ser Arg Glu Asp Leu
                965                 970                 975
Arg Arg Ser Thr Gly Lys Arg Ala His Lys Arg Asp Ile Cys Leu Lys
                980                 985                 990
Met His His Ile Gly Cys Gln Leu Cys Phe Ser Arg Arg Ser Arg Asp
            995                 1000                1005
Ala Ser Phe Ile Gln Asn Thr Tyr Leu His Lys Leu Ile Gly Glu His
        1010                1015                1020
Glu Ala Lys Ile Val Leu Met Pro Val His Thr Asp Ala Asp Ile Asp
1025                1030                1035                1040
Lys Ile Gln Leu Glu Ile Gln Ala Gly Ser Arg Ala Ala Arg Ile
                1045                1050                1055
Ile Thr Glu Val Asn Pro Glu Ser Glu Glu Asp Glu Ser Ser Pro
            1060                1065                1070
Tyr Glu Asp Ile Gln Ala Lys Leu Lys Arg Ile Leu Gly Ile Asp Ser
        1075                1080                1085
Met Phe Lys Val Ala Asn Lys Thr Arg His Pro Lys Asn Arg Pro Ser
        1090                1095                1100
Lys Lys Gly Asn Thr Val Leu Ala Glu Phe Gly Thr Glu Pro Asp Ala
1105                1110                1115                1120
Lys Thr Ser Ser Ser Ser Ser Ala Ser Ser Thr Ala Thr Ser Ser
                1125                1130                1135
Ser Ser Ser Ser Ala Ser Ser Pro Asn Arg Lys Lys Pro Met Asp Glu
            1140                1145                1150
Glu Glu Asn Asp Gln Val Lys Gln Ala Arg Asn Lys Asp Ala Ser Ser
        1155                1160                1165
Ser Ser Arg Ser Ser Lys Ser Ser Asn Ser Ser Lys Arg Ser Ser Ser
    1170                1175                1180
Lys Ser Ser Asn Ser Ser Lys Arg Ser Ser Ser Ser Ser Ser
1185                1190                1195                1200
Ser Ser Ser Ser Arg Ser Ser Ser Ser Ser Ser Ser Ser Asn
            1205                1210                1215
Ser Lys Ser Ser Ser Ser Ser Lys Ser Ser Ser Ser Ser Arg
        1220                1225                1230
```

-continued

```
Ser Arg Ser Ser Ser Lys Ser Ser Ser Ser Ser Ser Ser Ser
        1235                1240                1245
Ser Ser Ser Ser Lys Ser Ser Ser Arg Ser Ser Ser Ser Ser
        1250                1255                1260
Lys Ser Ser His His Ser His Ser His His Ser Gly His Leu Asn
1265                1270                1275                1280
Gly Ser Ser Ser Ser Ser Ser Ser Arg Ser Val Ser His His Ser
        1285                1290                1295
His Glu His His Ser Gly His Leu Glu Asp Asp Ser Ser Ser Ser
        1300                1305                1310
Ser Ser Ser Val Leu Ser Lys Ile Trp Gly Arg His Glu Ile Tyr Gln
        1315                1320                1325
Tyr Arg Phe Arg Ser Ala His Arg Gln Glu Phe Pro Lys Arg Lys Leu
        1330                1335                1340
Pro Gly Asp Arg Ala Thr Ser Arg Tyr Ser Ser Thr Arg Ser Ser His
1345                1350                1355                1360
Asp Thr Ser Arg Ala Ala Ser Trp Pro Lys Phe Leu Gly Asp Ile Lys
        1365                1370                1375
Thr Pro Val Leu Ala Ala Phe Leu His Gly Ile Ser Asn Asn Lys Lys
        1380                1385                1390
Thr Gly Gly Leu Gln Leu Val Val Tyr Ala Asp Thr Asp Ser Val Arg
        1395                1400                1405
Pro Arg Val Gln Val Phe Val Thr Asn Leu Thr Asp Ser Ser Lys Trp
        1410                1415                1420
Lys Leu Cys Ala Asp Ala Ser Val Arg Asn Ala His Lys Ala Val Ala
1425                1430                1435                1440
Tyr Val Lys Trp Gly Trp Asp Cys Arg Asp Tyr Lys Val Ser Thr Glu
        1445                1450                1455
Leu Val Thr Gly Arg Phe Ala Gly His Pro Ala Ala Gln Val Lys Leu
        1460                1465                1470
Glu Trp Pro Lys Val Pro Ser Asn Val Arg Ser Val Val Glu Trp Phe
        1475                1480                1485
Tyr Glu Phe Val Pro Gly Ala Ala Phe Met Leu Gly Phe Ser Glu Arg
        1490                1495                1500
Met Asp Lys Asn Pro Ser Arg Gln Ala Arg Met Val Val Ala Leu Thr
1505                1510                1515                1520
Ser Pro Arg Thr Cys Asp Val Val Lys Leu Pro Asp Ile Ile Leu
        1525                1530                1535
Tyr Gln Lys Ala Val Arg Leu Pro Leu Ser Leu Pro Val Gly Pro Arg
        1540                1545                1550
Ile Pro Ala Ser Glu Leu Gln Pro Pro Ile Trp Asn Val Phe Ala Glu
        1555                1560                1565
Ala Pro Ser Ala Val Leu Glu Asn Leu Lys Ala Arg Cys Ser Val Ser
        1570                1575                1580
Tyr Asn Lys Ile Lys Thr Phe Asn Glu Val Lys Phe Asn Tyr Ser Met
1585                1590                1595                1600
Pro Ala Asn Cys Tyr His Ile Leu Val Gln Asp Cys Ser Ser Glu Leu
        1605                1610                1615
Lys Phe Leu Val Met Met Lys Ser Ala Gly Glu Ala Thr Asn Leu Lys
        1620                1625                1630
Ala Ile Asn Ile Lys Ile Gly Ser His Glu Ile Asp Met His Pro Val
        1635                1640                1645
```

```
-continued

Asn Gly Gln Val Lys Leu Leu Val Asp Gly Ala Glu Ser Pro Thr Ala
    1650                1655                1660

Asn Ile Ser Leu Ile Ser Ala Gly Ala Ser Leu Trp Ile His Asn Glu
1665                1670                1675                1680

Asn Gln Gly Phe Ala Leu Ala Ala Pro Gly His Gly Ile Asp Lys Leu
                1685                1690                1695

Tyr Phe Asp Gly Lys Thr Ile Thr Ile Gln Val Pro Leu Trp Met Ala
            1700                1705                1710

Gly Lys Thr Cys Gly Ile Cys Gly Lys Tyr Asp Ala Glu Cys Glu Gln
        1715                1720                1725

Glu Tyr Arg Met Pro Asn Gly Tyr Leu Ala Lys Asn Ala Val Ser Phe
    1730                1735                1740

Gly His Ser Trp Ile Leu Glu Glu Ala Pro Cys Arg Gly Ala Cys Lys
1745                1750                1755                1760

Leu His Arg Ser Phe Val Lys Leu Glu Lys Thr Val Gln Leu Ala Gly
                1765                1770                1775

Val Asp Ser Lys Cys Tyr Ser Thr Glu Pro Val Leu Arg Cys Ala Lys
            1780                1785                1790

Gly Cys Ser Ala Thr Lys Thr Thr Pro Val Thr Val Gly Phe His Cys
        1795                1800                1805

Leu Pro Ala Asp Ser Ala Asn Ser Leu Thr Asp Lys Gln Met Lys Tyr
    1810                1815                1820

Asp Gln Lys Ser Glu Asp Met Gln Asp Thr Val Asp Ala His Thr Thr
1825                1830                1835                1840

Cys Ser Cys Glu Asn Glu Glu Cys Ser Thr
                1845                1850

<210> SEQ ID NO 6
<211> LENGTH: 70
<212> TYPE: PRT
<213> ORGANISM: Gallus gallus
<220> FEATURE:
<221> NAME/KEY: UNSURE
<222> LOCATION: (54)
<223> OTHER INFORMATION: Xaa = any residue
<221> NAME/KEY: UNSURE
<222> LOCATION: (63)
<223> OTHER INFORMATION: Xaa = any residue

<400> SEQUENCE: 6

Ala Gly Ser Ser His Glu Val Val Pro Ser Leu Leu Gln Thr Leu Leu
1               5                   10                  15

Glu Gly Ser Ile Glu Gln Leu Tyr Ala Gly Pro Ile Ser Arg Tyr Asn
            20                  25                  30

Val Asp Glu Met Thr Ser Ala Ala Leu Ala Glu Leu Lys Lys Cys Ile
        35                  40                  45

Asp Glu Leu Pro Pro Xaa His Leu Lys Ala Leu Val Asn Leu Xaa Lys
    50                  55                  60

Gln Ile Arg Thr Glu Ala
65                  70
```